United States Patent
Berger et al.

(10) Patent No.: US 10,065,945 B2
(45) Date of Patent: Sep. 4, 2018

(54) ISOQUINOLINE DERIVATIVES AS MGAT2 INHIBITORS

(71) Applicant: Merck Sharp & Dohme Corp., Rahway, NJ (US)

(72) Inventors: Richard Berger, Harleysville, PA (US); Timothy A. Blizzard, Princeton, NJ (US); Brian T. Campbell, Burlington, NJ (US); Helen Y. Chen, Marlboro, NJ (US); John S. Debenham, Scotch Plains, NJ (US); Sunita V. Dewnani, Secaucus, NJ (US); Byron Dubois, New York, NY (US); Candido Gude, Staten Island, NY (US); Zack Zhiqiang Guo, Morganville, NJ (US); Bart Harper, New York, NY (US); Zhiyong Hu, Livingston, NJ (US); Songnian Lin, Holmdel, NJ (US); Ping Liu, Westfield, NJ (US); Ming Wang, Belle Mead, NJ (US); Feroze Ujjainwalla, Hoboken, NJ (US); Jiayi Xu, Marlboro, NJ (US); Libo Xu, Bridgewater, NJ (US); Rui Zhang, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 198 days.

(21) Appl. No.: 15/104,537

(22) PCT Filed: Jan. 20, 2015

(86) PCT No.: PCT/US2015/011939
§ 371 (c)(1),
(2) Date: Jun. 15, 2016

(87) PCT Pub. No.: WO2015/112465
PCT Pub. Date: Jul. 30, 2015

(65) Prior Publication Data
US 2018/0009796 A1    Jan. 11, 2018

Related U.S. Application Data

(60) Provisional application No. 61/931,005, filed on Jan. 24, 2014.

(51) Int. Cl.
C07D 413/14    (2006.01)
C07D 417/14    (2006.01)
C07D 413/12    (2006.01)
C07D 471/04    (2006.01)
C07D 401/12    (2006.01)

(52) U.S. Cl.
CPC ......... C07D 413/14 (2013.01); C07D 401/12 (2013.01); C07D 413/12 (2013.01); C07D 417/14 (2013.01); C07D 471/04 (2013.01)

(58) Field of Classification Search
CPC .. C07D 413/14; C07D 401/12; C07D 413/12; C07D 417/14; C07D 47/104
USPC ................................................... 514/210.18
See application file for complete search history.

(56) References Cited

U.S. PATENT DOCUMENTS

| 5,217,976 A | 6/1993 | Ratcliffe et al. |
| 8,232,282 B2 | 7/2012 | Nakamura et al. |
| 2009/0170885 A1 | 7/2009 | Vernier et al. |

FOREIGN PATENT DOCUMENTS

| EP | 2687507 A1 | 1/2014 |
| WO | WO199915526 A2 | 4/1999 |
| WO | WO2006122014 | 11/2006 |
| WO | WO2008038768 A1 | 4/2008 |
| WO | WO2009037542 A2 | 3/2009 |

OTHER PUBLICATIONS

Chemical Abstracts, STN Registry Database records for registry numbers: 1394628-66-0, 1394625-91-2, 1394618-42-8, 1394589-42-4, 1394530-35-8, 1394519-14-2, 1394519-03-9, 1394518-47-8, 1394498-21-5, 1394496-44-6, 1394434 44 6 and 1394394-80-9, all entered into the database on Sep. 18, 2012, 5 pp. (Year: 2012).*
Haslam; Primary Care Diabetes 2010, 4 , 105-112. (Year: 2010).*
Tsuchida; Lipids in Health and Disease 2012, 11, 75, 10 pages. (Year: 2012).*
Cao, J. et al., A Predominant Role of Acyl-CoA:monoacylglycerol Acyltransferase-2 in Dietary Fat Absorption Implicated by Tissue Distribution, Subcellular Localization, and Up-regulation by High Fat Diet, The Journal of Biological Chemistry, 2004, p. 18878-18886, vol. 279, No. 18, Issue of Apr. 30.
Cao, J. et al., Cloning and Functional Characterization of a Mouse Intestinal Acyl-CoA:Monoacylglycerol Acyltransferase, MGAT2, The Journal of Biological Chemistry, 2003, p. 13860-13866, vol. 278, No. 16, Issue of Apr. 18.
Cheng, D. et al., Identification of Acyl Coenzyme A:Monoacylglycerol Acyltransferase 3, an Intestinal Specific Enzyme Implicated in Dietary Fat Absorption, The Journal of Biological Chemistry, 2003, p. 13611-13614, vol. 278, No. 16, Issue of Apr. 18.

(Continued)

*Primary Examiner* — Daniel R Carcanague
(74) *Attorney, Agent, or Firm* — Janet E. Fair; Catherine D. Fitch

(57) ABSTRACT

The compounds of Formula I act as MGAT2 inhibitors and can be useful in preventing, treating or acting as a remedial agent for hyperlipidemia, diabetes mellitus and obesity.

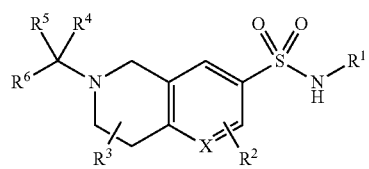

14 Claims, No Drawings

(56) References Cited

OTHER PUBLICATIONS

Coleman, R. A. et al., Hepatic Monoacylglycerol Acyltransferase, The Journal of Biological Chemistry, 1984, p. 8934-8938, vol. 259, No. 14, Issue of Jul. 25.

International Search Report for PCT/US2015/011939 dated Jun. 24, 2015, 10 pages.

Iyaku, R. et al., Journal of Clinical Therapeutics & Medicines, General Collection, 2005, p. 215-225, vol. 21, No. 2.

Luan, Y. et al., Pathogenesis of obesity by food restriction in OLETF rats-increased intestinal monoacylglycerol acyltransferase activities may be a crucial factor, Diabetes Research and Clinical Practice, 2002, p. 75-82, vol. 57.

PUBCHEM, Compound Summary for CID 70788599 - AGN-PC-0J2MV3, PubChem, 2013, p. 1-10.

Yen, C. L. E. et al., Identification of a gene encoding MGAT1, a monoacylglycerol acyltransferase, PNAS, 2002, p. 8512-8517, vol. 99, No. 13.

Yen, C. L. E. et al., MGAT2, a Monoacylglycerol Acyltransferase Expressed in the Small Intestine, The Journal of Biological Chemistry, 2003, p. 18532-18537, vol. 278, No. 20, Issue of May 16.

* cited by examiner

ISOQUINOLINE DERIVATIVES AS MGAT2 INHIBITORS

CROSS-REFERENCE TO RELATED APPLICATIONS

This application is a U.S. National Phase application under 35 U.S.C. § 371 of PCT Application No. PCT/US2015/011939, filed Jan. 20, 2015, which published as WO 2015/112465 A1 on Jul. 30, 2015, and claims priority under 35 U.S.C. § 365(b) from U.S. provisional patent application No. 61/931,005, filed Jan. 24, 2014.

TECHNICAL FIELD

The present invention is directed to isoquinoline derivative compounds. Specifically, the compounds act as monoacylglycerol acyltransferase type 2 (hereinafter also referred to as "MGAT2"), and can be useful in preventing, treating or acting as a remedial agent for hyperlipidemia, diabetes mellitus and obesity.

BACKGROUND

Obesity is a condition in which the background of lack of exercise, intake of excessive energy, ageing, etc., leads to energy imbalance in the body. The surplus energy is accumulated generally as neutral fat (triacylglycerol, TG) in adipose tissue, and body weight and fat mass are thus increased. In recent years, the concept of metabolic syndrome associated with obesity involving the accumulation of visceral fat, as an upstream risk factor including a plurality of risk factors of diabetes, lipidosis, hypertension, etc. has been established, and the diagnostic criteria and therapeutic guidelines for metabolic syndrome were formulated (Journal of Japan Society for the Study of Obesity, vol. 12, Extra Edition, 2006). Since metabolic syndrome results in an increase in the risks of arteriosclerosis, cardiovascular disorder and cerebrovascular disorder, treatment of obesity has been recognized to be important for preventing these diseases.

Although the need for treating obesity is recognized to be important, there are extremely-limited drug therapies for obesity that are currently available, and there is no drug that is sufficiently satisfactory in terms of drug efficacy or side effects. Thus, development of novel antiobestic drugs having more definite action and few side-effects is desired.

Not less than 90% of lipid present in food is TG. TG derived from food is decomposed into 2-monoacylglycerol (2-MG) and free fatty acid (FFA) by the cleavage of the ester linkages of aliphatic acids at the 1- and 3-positions by lipase in digestive juice, which is secreted from the pancreas and the stomach. The 2-MG and FFA as well as bile acid are micellized and absorbed into small intestinal epithelial cells. The absorbed 2-MG and FFA resynthesize TG in the small intestinal cells, and the resynthesized TG as lipoprotein referred to as chylomicron (CM) is released into the lymph and supplied to the whole body. The TG resynthesis in the small intestinal cells is through two pathways, 2-MG and α-glycerophosphoric acid pathways. Typically, 80% of TG is resynthesized in the 2-MG pathway and the remaining 20% in the 2-plycerophosphoric acid pathways. The TG generated in the 2-MG pathway is utilized for generation of CM in accelerated turnover, and the synthesized CM is secreted into the intestinal lymph and then into blood and is transferred into peripheral tissue (Journal of Clinical Therapeutics and Medicine, vol. 21, No. 2, p. 216, 2005).

Enzymes such as MGATs (acyl-CoA:monoacylglycerol acyltransferases) and DGATs (acyl-CoA:diacylglycerol acyltransferases) are involved specifically in synthesis of TG in a 2-MG pathway. MGATs catalyze a reaction of generation of diacylglycerol by binding between 2-MG generated by lipase and fatty acyl-CoA, whereas DGATs catalyze a reaction of generation of TG by binding between the diacylglycerol generated by the catalytic reaction of the MGATs and fatty acyl-CoA.

Although such MGATs have been suggested to be present in the liver or white adipose tissue (J. Biol. Chem, vol. 259, p. 8934, 1984), the cloning of MGAT1 gene, a member of the family of MGATs, has been achieved in recent years, where the gene was isolated, as molecules expressed highly in the kidney, stomach, and white fat and brown fat cells, from a mouse (Proc. Natl. Acad. Sci. USA., vol. 99, p. 8512, 2002). However, although the activity of MGATs was observed significantly in the small intestine, no MGAT1 was expressed in the small intestine, and different molecules belonging to the family of MGATs were thus believed to be present.

Afterward, MGAT2 was cloned through homology search based on the cDNA sequence of MGAT1 by Cao et al., to isolate full-length cDNA from a cDNA library from the mouse small intestine (J. Biol. Chem, vol. 278, p. 13611, 2003). In addition, MGAT3 has been reported to be present in human (J. Biol. Chem, vol. 278, p. 13611, 2003), whereas no MGAT3 has been reported in rodents. The mouse MGAT2 is a 38.6-kDa protein including 334 amino acids, has an N-terminal 40-amino acid signal peptide, includes at least one transmembrane domain, and is expressed strongly in a small intestinal epithelial cell (J. Biol. Chem, vol. 278, p. 13860, 2003). In addition, both human and mouse MGATs2 were reported to include 334 amino acids and have 81% homology in human and mouse amino acid sequences, through the cloning of the human and mouse MGATs2, by Yen et al. (J. Biol. Chem, vol. 278, p. 18532, 2003). The expression pattern of MGAT2 in the small intestine has been exhibited to be similar to that of the site of absorbed lipid (J. Biol. Chem, vol. 279, p. 18878, 2004). In addition, the expression or activity of MGAT2 in the small intestine has been indicated to increase in high-fat diet-induced obesity mice (J. Biol. Chem, vol. 279, p. 18878, 2004) and OLETF rats exhibiting obesity or hypertriglyceridemia (Diabetes Res. Clin. Pract, vol. 57, p. 75, 2002), suggesting that MGAT2 is important for absorbing lipid and is involved in obesity or hypertriglyceridemia.

From the results, an MGAT2 inhibitor is expected to be useful as an agent for treating or preventing obesity, or type 2 diabetes, lipidosis, hypertension, fatty liver, arterial sclerosis, cerebrovascular disorder, coronary artery disease, etc., associated with obesity, through suppressing absorption of lipid.

As a compound having an MGAT2 inhibitory action, for example, a compound represented by the following structure:

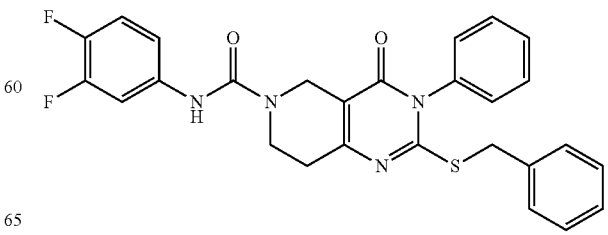

has been disclosed (e.g., see WO 2008/038768). A compound according to an embodiment of the present invention is different from the compound disclosed in WO 2008/038768, in that the compound disclosed in WO 2008/038768 has substituted phenylaminocarbonyl at the 6-position of the 3,4,5,6,7,8-hexahydro-4-oxopyrido[4,3-d]pyrimidine ring whereas the compound according to an embodiment of the present invention has substituted benzimidazolyl. Furthermore, in WO 2008/038768, the substituted phenylaminocarbonyl is not disclosed or suggested to be replaced with substituted benzimidazolyl.

SUMMARY

A compound of formula (I):

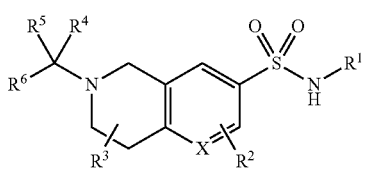

or pharmaceutically acceptable salts thereof, wherein X is —N— or —CH—;

$R^1$ is a nitrogen containing heterocycle, wherein the nitrogen containing heterocycle is substituted with one or two substituents independently selected from the group consisting of $C_1$-$C_6$alkyl, $C_2$-$C_6$alkene, halogen, halogen-substituted$C_1$-$C_6$alkyl, COO$C_1$-$C_6$alkyl, CONH$_2$, CONH$C_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NH$C_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine;

$R^2$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^3$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^4$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH or when combined with $R^5$ is an oxo group;

$R^5$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and —$C_1$-$C_6$alkylOH, or when combined with $R^4$ is an oxo group; and $R^6$ is selected from the group consisting of phenyl, a nitrogen containing heterocycle, wherein the phenyl or nitrogen containing heterocycle is unsubstituted or substituted with one, two or three substituents independently selected from the group consisting of $C_1$-$C_6$alkyl, $C_2$-$C_6$alkene, halogen, halogen-substituted$C_1$-$C_6$alkyl, —COO$C_1$-$C_6$alkyl, CONH$_2$, CONH$C_1$-$C_6$alkyl, CON($C_1$-$C_6$alkyl)$_2$, CONH-halogen-substituted$C_1$-$C_6$alkyl, $C_1$-$C_6$alkoxy, halogen-substituted$C_1$-$C_6$alkoxy, —NH$C_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, OH, —$C_1$-$C_6$alkylOH, —O$C_1$-$C_6$alkyl-O—$C_1$-$C_6$alkyl, S$C_1$-$C_6$alkyl, —S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

The compounds described herein are MGAT2 inhibitors, which are useful in the treatment of type 2 diabetes mellitus, obesity, lipidosis, hypertension, fatty liver, arteriosclerosis, cerebrovascular disorder, coronary artery disease and metabolic syndrome, particularly, obesity and diabetes.

DETAILED DESCRIPTION

Compounds

Described herein are compounds of formula (I):

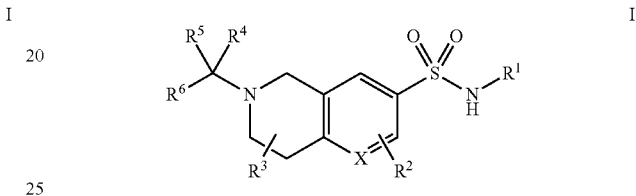

or pharmaceutically acceptable salts thereof, wherein X is —N— or —CH—;

$R^1$ is a nitrogen containing heterocycle, wherein the nitrogen containing heterocycle is substituted with one or two substituents independently selected from the group consisting of $C_1$-$C_6$alkyl, $C_2$-$C_6$alkene, halogen, halogen-substituted$C_1$-$C_6$alkyl, COO$C_1$-$C_6$alkyl, CONH$_2$, CONH$C_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NH$C_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine;

$R^2$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^3$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^4$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH, or when combined with $R^5$ is an oxo group;

$R^5$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and —$C_1$-$C_6$alkylOH, or when combined with $R^4$ is an oxo group; and $R^6$ is selected from the group consisting of phenyl, a nitrogen containing heterocycle, wherein the phenyl or nitrogen containing heterocycle is unsubstituted or substituted with one, two or three substituents independently selected from the group consisting of $C_1$-$C_6$alkyl, $C_2$-$C_6$alkene, halogen, halogen-substituted$C_1$-$C_6$alkyl, —COO$C_1$-$C_6$alkyl, CONH$_2$, CONH$C_1$-$C_6$alkyl, CON($C_1$-$C_6$alkyl)$_2$, CONH-halogen-substituted$C_1$-$C_6$alkyl, $C_1$-$C_6$alkoxy, halogen-substituted$C_1$-$C_6$alkoxy, —NH$C_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-

$C_6$alkyl-halogen-substituted$C_3$-$C_6$cycloalkyl, OH, —$C_1$-$C_6$alkylOH, —O$C_1$-$C_6$alkyl-O—$C_1$-$C_6$alkyl, S$C_1$-$C_6$alkyl, —S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

Described herein are compounds of Formula (I) wherein, X is —N— or —CH—. In certain embodiments, X is —N—. In other embodiments, X is —CH—.

Also, described herein are compounds of Formula (I), wherein $R^1$ is a nitrogen containing heterocycle. In certain embodiments of the compounds described herein, $R^1$ is a nitrogen containing heterocycle. Suitable, heterocycles include, but are not limited to, isoxazole, oxadiazole, pyrazine, pyridazine and pyridine. Nitrogen-containing heterocycles are heterocycles that contain at least one nitrogen. In certain embodiments of the compounds described herein, $R^1$ is selected from the group consisting of isoxazole, pyrazine, oxadiazole and pyridazine. In yet other embodiments, $R^1$ is isoxazole.

In certain embodiments of the compounds described herein, $R^1$ is substituted with one or two substituents independently selected from the group consisting of $C_1$-$C_6$alkyl, $C_2$-$C_6$alkene, halogen, halogen-substituted$C_1$-$C_6$alkyl, COO$C_1$-$C_6$alkyl, CON$H_2$, CONH$C_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NH$C_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, pyrazole, N-methyl pyrazole, pyrroline, CO-pyrrolidine, azetidine and CO-azetidine.

In certain embodiments, $R^1$ is substituted with one substituent. In certain embodiments, $R^1$ is substituted with more than one substituent. In other embodiments, $R^1$ is substituted with two substituents. In still other embodiments, $R^1$ is substituted with three substituents. In yet other embodiments, $R^1$ is substituted with four substituents.

$R^1$ can be substituted with substituents independently selected from the group consisting of $C_1$-$C_6$alkyl, $C_2$-$C_6$alkene, halogen, halogen-substituted$C_1$-$C_6$alkyl, COO$C_1$-$C_6$alkyl, CON$H_2$, CONH$C_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NH$C_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, pyrazole, N-methyl pyrazole, azetidine and CO-azetidine.

In certain embodiments, $R^1$ can be substituted with $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include, methyl, ethyl and tert-butyl.

In certain embodiments, $R^1$ can be substituted with $C_2$-$C_6$alkene. Suitable alkenes include, but are not limited to, ethenyl, propenyl, n-butenyl, 3-methylbut-2-enyl and n-pentenyl.

In certain embodiments, $R^1$ can be substituted with halogen. Suitable halogens include, but are not limited to, fluorine, chlorine, bromine, and iodine.

In certain embodiments, $R^1$ can be substituted with halogen-substituted$C_1$-$C_6$alkyl.

Suitable halogen-substituted alkyls include, but are not limited to, fluoromethyl, difluoromethyl, trifluoromethyl, 2-fluoroethyl, 1,2-difluoroethyl and 2,2-difluoroethyl.

In certain embodiments, $R^1$ can be substituted with COO$C_1$-$C_6$alkyl. Suitable alkoxy carbonyls include, but are not limited to, methoxycarbonyl, ethoxycarbonyl and butoxycarbonyl.

In certain embodiments, $R^1$ can be substituted with CON$H_2$.

In certain embodiments, $R^1$ can be substituted with CONH$C_1$-$C_6$alkyl. Suitable examples include, but are not limited to, methylcarbamoyl, ethylcarbamoyl, n-propylcarbamoyl, isopropylcarbamoyl, n-butylcarbamoyl, sec-butylcarbamoyl and tert-butylcarbamoyl.

In certain embodiments, $R^1$ can be substituted with CON($C_1$-$C_6$alkyl)$_2$. Suitable examples include, but are not limited to, dimethylcarbamoyl, diethylcarbamoyl, ethylmethylcarbamoyl, di(n-propyl)carbamoyl, methyl(n-propyl)carbamoyl, and diisopropylcarbamoyl.

In certain embodiments, $R^1$ can be substituted with CONHhalogen-substituted$C_1$-$C_6$alkyl. Suitable CONHhalogen-substituted$C_1$-$C_6$alkyl include, but are not limited to, the CONH$C_1$-$C_6$alkyl listed above, wherein the alkyl is substituted with one or more halogens.

In certain embodiments, $R^1$ can be substituted with $C_1$-$C_6$alkoxy. Suitable examples of alkoxys include, but are not limited to, methoxy, ethoxy, butoxy and propoxy.

In certain embodiments, $R^1$ can be substituted with halogen-substituted$C_1$-$C_6$alkoxy. Suitable examples of halogen-substituted alkoxys include, but are not limited to, trifluoromethoxy.

In certain embodiments, $R^1$ can be substituted with NH$C_1$-$C_6$alkyl. Suitable examples include, but are not limited to, methylamino, ethylamino, n-propylamino, isopropylamino, n-butylamino, sec-butylamino and tert-butylamino.

In certain embodiments, $R^1$ can be substituted with $C_3$-$C_6$cycloalkyl. Suitable cycloalkyls include, but are not limited to, cyclopropyl, cyclobutyl, cyclopentyl, cyclohexyl, cycloheptyl, tetrahydronaphthyl, decahydronaphthyl and indanyl.

In certain embodiments, $R^1$ can be substituted with halogen-substituted$C_3$-$C_6$cycloalkyl. Suitable halogen-substituted cycloalkyls include, but are not limited to, the cycloakyls listed above, wherein the cycloalkyl is substituted with one or more halogens.

In certain embodiments, $R^1$ can be substituted with —OH.

In certain embodiments, $R^1$ can be substituted with $C_1$-$C_6$alkylOH. Suitable examples of alkyl alcohols include, but are not limited to, methanol, propanol, butanol and t-butanol.

In certain embodiments, $R^1$ can be substituted with pyrrole.

In certain embodiments, $R^1$ can be substituted with phenyl.

In certain embodiments, $R^1$ can be substituted with halogen-substituted phenyl. Suitable halogen-substituted phenyls include, but are not limited to, fluorophenyl.

In certain embodiments, $R^1$ can be substituted with pyrazole.

In certain embodiments, $R^1$ can be substituted with N-methyl pyrazole.

In certain embodiments, $R^1$ can be substituted with pyrroline.

In certain embodiments, $R^1$ can be substituted with CO-pyrrolidine.

In certain embodiments, $R^1$ can be substituted with azetidine.

In certain embodiments, $R^1$ can be substituted with CO-azetidine.

Described herein are compounds of Formula (I) wherein, $R^2$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH. In certain embodiments, $R^2$ is hydrogen. In other embodiments, $R^2$ is halogen. Suitable halogens include, but are not limited to, fluorine, chlorine, bromine, and iodine.

In other embodiments, $R^2$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include, methyl, ethyl and tert-butyl. In other embodiments, $R^2$ is halogen-substituted$C_1$-$C_6$alkyl. Suitable halogen-substituted alkyls include, but are not limited to, fluoromethyl, difluoromethyl, trifluoromethyl, 2-fluoroethyl, 1,2-difluoroethyl and 2,2-difluoroethyl.

In other embodiments, $R^2$ is $C_1$-$C_6$alkoxy. Suitable examples of alkoxys include, but are not limited to, methoxy, ethoxy, butoxy and propoxy. In still other embodiments, $R^2$ is halogen-substituted$C_1$-$C_6$alkoxy. Suitable examples of halogen-substituted alkoxys include, but are not limited to, trifluoromethoxy.

In other embodiments, $R^2$ is —OH. In still other embodiments, $R^2$ is $C_1$-$C_6$alkylOH. Suitable examples of alkyl alcohols include, but are not limited to, methanol, propanol, butanol and t-butanol.

Described herein are compounds of Formula (I) wherein, $R^3$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH. In certain embodiments, $R^3$ is hydrogen. In other embodiments, $R^3$ is halogen. Suitable halogens include, but are not limited to, fluorine, chlorine, bromine, and iodine.

In other embodiments, $R^3$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include methyl, ethyl and tert-butyl. In other embodiments, $R^3$ is halogen-substituted$C_1$-$C_6$alkyl. Suitable halogen-substituted alkyls include, but are not limited to, fluoromethyl, difluoromethyl, trifluoromethyl, 2-fluoroethyl, 1,2-difluoroethyl and 2,2-difluoroethyl.

In other embodiments, $R^3$ is $C_1$-$C_6$alkoxy. Suitable examples of alkoxys include, but are not limited to, methoxy, ethoxy, butoxy and propoxy. In still other embodiments, $R^3$ is halogen-substituted$C_1$-$C_6$alkoxy. Suitable examples of halogen-substituted alkoxys include, but are not limited to, trifluoromethoxy.

In other embodiments, $R^3$ is —OH. In still other embodiments, $R^3$ is $C_1$-$C_6$alkylOH. Suitable examples of alkyl alcohols include, but are not limited to, methanol, propanol, butanol and t-butanol.

Described herein are compounds of Formula (I) wherein, $R^4$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH, or when combined with $R^5$ is an oxo group. In certain embodiments, $R^4$ is hydrogen. In other embodiments, $R^4$ is halogen. Suitable halogens include, but are not limited to, fluorine, chlorine, bromine, and iodine.

In other embodiments, $R^4$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include methyl, ethyl and tert-butyl. In other embodiments, $R^4$ is halogen-substituted$C_1$-$C_6$alkyl. Suitable halogen-substituted alkyls include, but are not limited to, fluoromethyl, difluoromethyl, trifluoromethyl, 2-fluoroethyl, 1,2-difluoroethyl and 2,2-difluoroethyl.

In other embodiments, $R^4$ is $C_1$-$C_6$alkoxy. Suitable examples of alkoxys include, but are not limited to, methoxy, ethoxy, butoxy and propoxy. In still other embodiments, $R^4$ is halogen-substituted$C_1$-$C_6$alkoxy. Suitable examples of halogen-substituted alkoxys include, but are not limited to, trifluoromethoxy.

In other embodiments, $R^4$ is —OH. In still other embodiments, $R^4$ is $C_1$-$C_6$alkylOH. Suitable examples of alkyl alcohols include, but are not limited to, methanol, propanol, butanol and t-butanol.

In certain embodiments of the compounds described herein, $R^4$ is hydrogen or $C_1$-$C_6$alkyl. In other embodiments of the compounds described herein, $R^4$ is hydrogen or methyl. In still other embodiments of the compounds described herein, $R^4$ is methyl.

In still other embodiments, $R^4$ is combined with $R^5$ to form an oxo group

Described herein are compounds of Formula (I) wherein, $R^5$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH. In certain embodiments, $R^5$ is hydrogen. In other embodiments, $R^5$ is halogen. Suitable halogens include, but are not limited to, fluorine, chlorine, bromine, and iodine.

In other embodiments, $R^5$ is $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include methyl, ethyl and tert-butyl. In other embodiments, $R^5$ is halogen-substituted$C_1$-$C_6$alkyl. Suitable halogen-substituted alkyls include, but are not limited to, fluoromethyl, difluoromethyl, trifluoromethyl, 2-fluoroethyl, 1,2-difluoroethyl and 2,2-difluoroethyl.

In other embodiments, $R^5$ is $C_1$-$C_6$alkoxy. Suitable examples of alkoxys include, but are not limited to, methoxy, ethoxy, butoxy and propoxy. In still other embodiments, $R^5$ is halogen-substituted$C_1$-$C_6$alkoxy. Suitable examples of halogen-substituted alkoxys include, but are not limited to, trifluoromethoxy.

In other embodiments, $R^5$ is —OH. In still other embodiments, $R^5$ is $C_1$-$C_6$alkylOH. Suitable examples of alkyl alcohols include, but are not limited to, methanol, propanol, butanol and t-butanol.

In still other embodiments, $R^5$ is combined with $R^4$ to form an oxo group

Described herein are compounds of Formula (I) wherein $R^6$ is selected from the group consisting of phenyl or a nitrogen containing heterocycle. In certain embodiments, $R^6$ is phenyl. In other embodiments, $R^6$ is a nitrogen containing heterocycle. Suitable heterocycles include, but are not limited to, thiazole, pyrimidine, pyridine and pyrazine. In still yet other embodiments, $R^6$ is selected from the group consisting of pyrimidine, pyridine, thiazole and pyrazine.

In certain embodiments of the compounds described herein, $R^6$ is unsubstituted.

In certain embodiments, $R^6$ is substituted with one substituent. In certain embodiments, $R^6$ is substituted with more than one substituent. In other embodiments, $R^6$ is substituted with two substituents. In still other embodiments, $R^6$ is substituted with three substituents. In yet other embodiments, substituted with one, two or three substituents.

In certain embodiments of the compounds described herein, $R^6$ can be substituted with $C_1$-$C_6$alkyl, $C_2$-$C_6$alkene, halogen, halogen-substituted$C_1$-$C_6$alkyl, —COO$C_1$-$C_6$alkyl, CONH$_2$, CONH$C_1$-$C_6$alkyl, CON($C_1$-$C_6$alkyl)$_2$, CONH-halogen-substituted$C_1$-$C_6$alkyl, $C_1$-$C_6$alkoxy, halogen-substituted$C_1$-$C_6$alkoxy, —NH$C_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, OH, —$C_1$-$C_6$alkylOH, —O$C_1$-$C_6$alkyl-O—$C_1$-$C_6$alkyl, S$C_1$-$C_6$alkyl, S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

In certain embodiments, $R^6$ can be substituted with $C_1$-$C_6$alkyl. Suitable alkyls include, but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl. More specific examples include, methyl, ethyl and tert-butyl.

In certain embodiments, $R^6$ can be substituted with $C_2$-$C_6$alkene. Suitable alkenes include, but are not limited to, ethenyl, propenyl, n-butenyl, 3-methylbut-2-enyl and n-pentenyl.

In certain embodiments, $R^6$ can be substituted with halogen. Suitable halogens include, but are not limited to, fluorine, chlorine, bromine, and iodine.

In certain embodiments, $R^6$ can be substituted with halogen-substituted$C_1$-$C_6$alkyl. Suitable halogen-substituted alkyls include, but are not limited to, fluoromethyl, difluoromethyl, trifluoromethyl, 2-fluoroethyl, 1,2-difluoroethyl and 2,2-difluoroethyl.

In certain embodiments, $R^6$ can be substituted with COO$C_1$-$C_6$alkyl. Suitable alkoxy carbonyls include, but are not limited to, methoxycarbonyl, ethoxycarbonyl and butoxycarbonyl.

In certain embodiments, $R^6$ can be substituted with CONH$_2$.

In certain embodiments, $R^6$ can be substituted with CONH$C_1$-$C_6$alkyl. Suitable examples include, but are not limited to, methylcarbamoyl, ethylcarbamoyl, n-propylcarbamoyl, isopropylcarbamoyl, n-butylcarbamoyl, sec-butylcarbamoyl and tert-butylcarbamoyl.

In certain embodiments, $R^6$ can be substituted with CON($C_1$-$C_6$alkyl)$_2$. Suitable examples include, but are not limited to, dimethylcarbamoyl, diethylcarbamoyl, ethylmethylcarbamoyl, di(n-propyl)carbamoyl, methyl(n-propyl)carbamoyl, and diisopropylcarbamoyl.

In certain embodiments, $R^6$ can be substituted with CONHhalogen-substituted$C_1$-$C_6$alkyl. Suitable CONHhalogen-substituted$C_1$-$C_6$alkyl include, but are not limited to, the CONH$C_1$-$C_6$alkyl listed above, wherein the alkyl is substituted with one or more halogens.

In certain embodiments, $R^6$ can be substituted with $C_1$-$C_6$alkoxy. Suitable examples of alkoxys include, but are not limited to, methoxy, ethoxy, butoxy and propoxy.

In certain embodiments, $R^6$ can be substituted with halogen-substituted$C_1$-$C_6$alkoxy. Suitable examples of halogen-substituted alkoxys include, but are not limited to, trifluoromethoxy.

In certain embodiments, $R^6$ can be substituted with NH$C_1$-$C_6$alkyl. Suitable examples include, but are not limited to, methylamino, ethylamino, n-propylamino, isopropylamino, n-butylamino, sec-butylamino and tert-butylamino.

In certain embodiments, $R^6$ can be substituted with $C_3$-$C_6$cycloalkyl. Suitable cycloalkyls include, but are not limited to, cyclopropyl, cyclobutyl, cyclopentyl, cyclohexyl, cycloheptyl, tetrahydronaphthyl, decahydronaphthyl and indanyl.

In certain embodiments, $R^6$ can be substituted with halogen-substituted$C_3$-$C_6$cycloalkyl. Suitable halogen-substituted cycloalkyls include, but are not limited to, the cycloakyls listed above, wherein the cycloalkyl is substituted with one or more halogens.

In certain embodiments, $R^6$ can be substituted with O—$C_1$-$C_6$alkyl-$C_3$-$C_6$cycloalkyl.

In certain embodiments, $R^6$ can be substituted with O—$C_1$-$C_6$alkyl-halogen-substituted$C_3$-$C_6$cycloalkyl.

In certain embodiments, $R^6$ can be substituted with —OH.

In certain embodiments, $R^6$ can be substituted with $C_1$-$C_6$alkylOH. Suitable examples of alkyl alcohols include, but are not limited to, methanol, propanol, butanol and t-butanol.

In certain embodiments, $R^6$ can be substituted with —O—$C_1$-$C_6$alkyl-O—$C_1$-$C_6$alkyl.

In certain embodiments, $R^6$ can be substituted with S$C_1$-$C_6$alkyl.

In certain embodiments, $R^6$ can be substituted with S-halogen-substituted$C_1$-$C_6$ alkyl.

In certain embodiments, $R^6$ can be substituted with pyrrole.

In certain embodiments, $R^6$ can be substituted with phenyl.

In certain embodiments, $R^6$ can be substituted with halogen-substituted phenyl. Suitable halogen-substituted phenyls include, but are not limited to, fluorophenyl.

In certain embodiments, $R^6$ can be substituted with pyrazole.

In certain embodiments, $R^6$ can be substituted with N-methyl pyrazole.

In certain embodiments, $R^6$ can be substituted with azetidine.

In certain embodiments, $R^1$ can be substituted with pyrroline.
In certain embodiments, $R^1$ can be substituted with CO-pyrrolidine.
In certain embodiments, $R^6$ can be substituted with CO-azetidine.
Examples of the compounds described herein include, but are not limited to the following and their pharmaceutically acceptable salts:
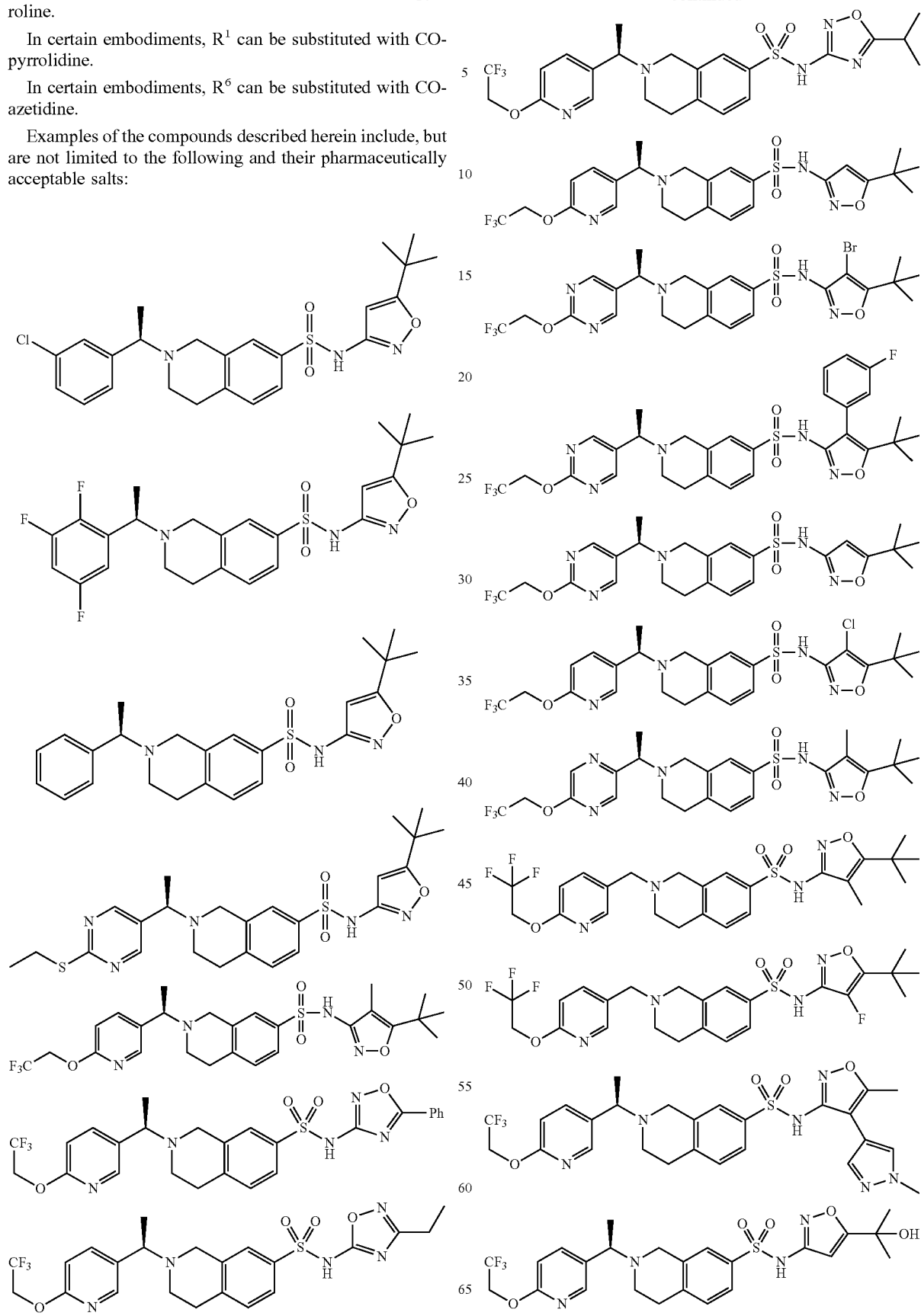

-continued

-continued
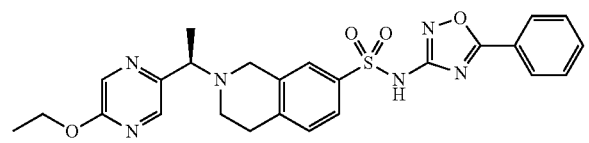
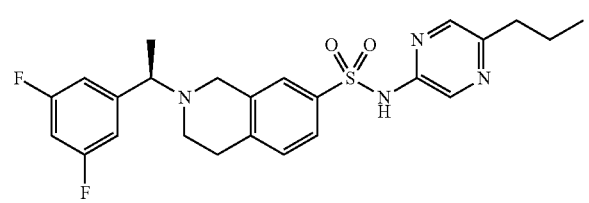
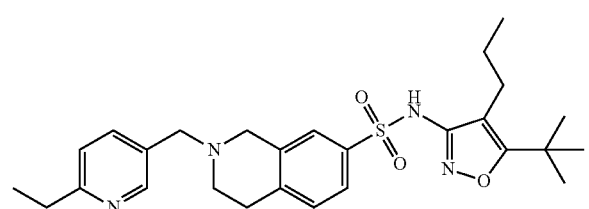
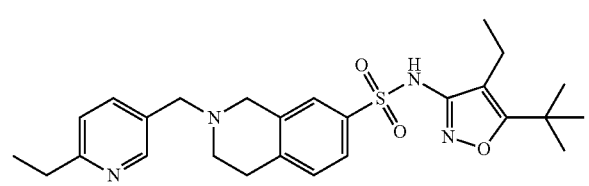
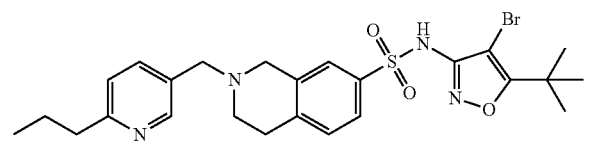
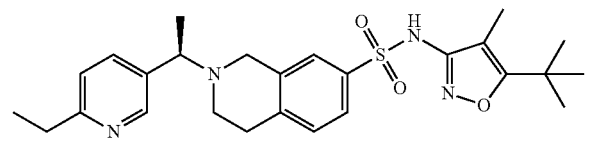
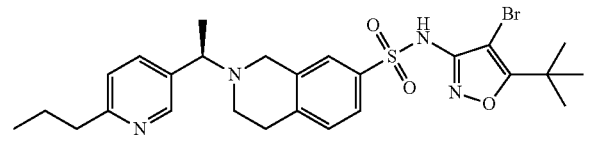
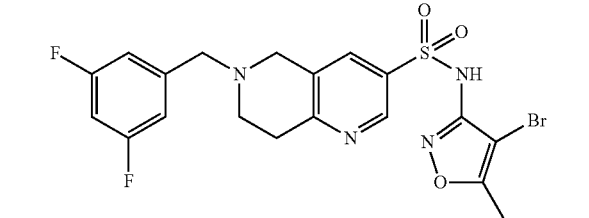
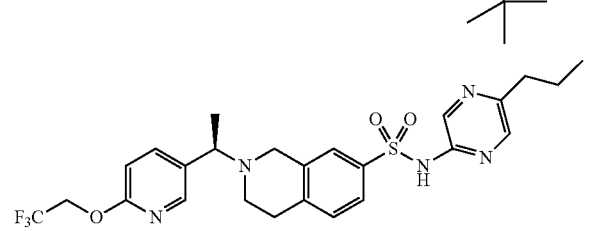
-continued
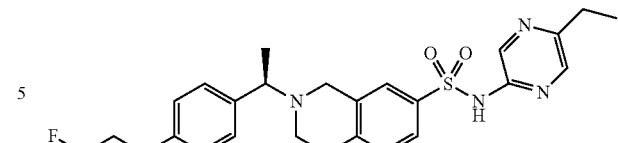
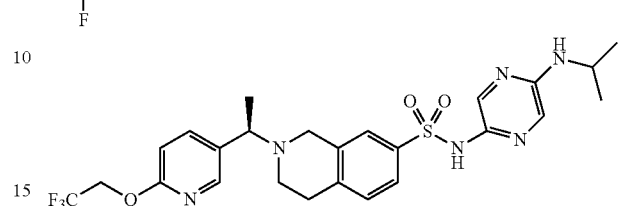
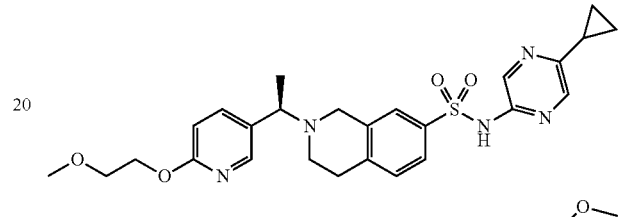
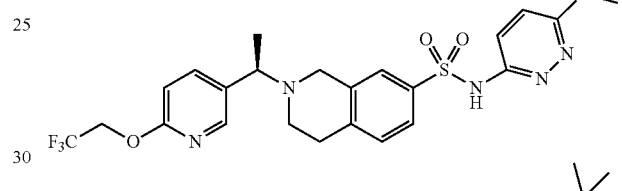
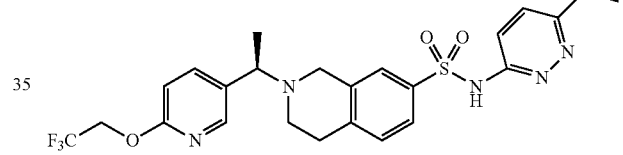
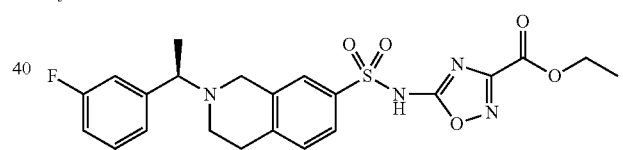
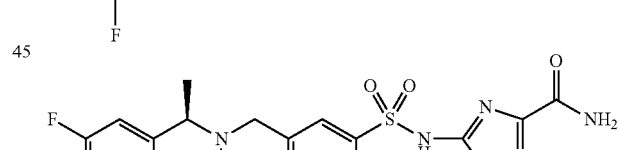
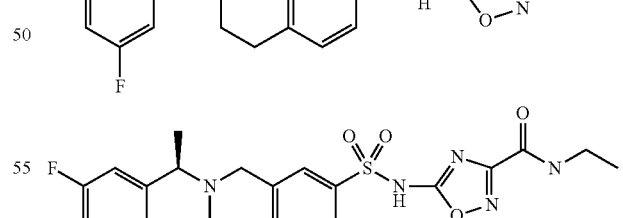
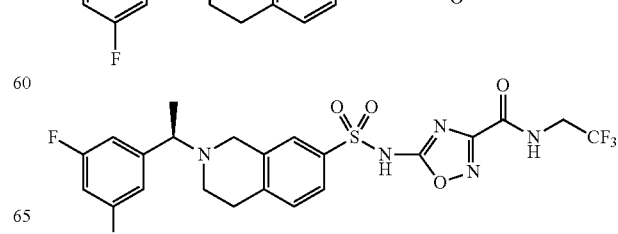

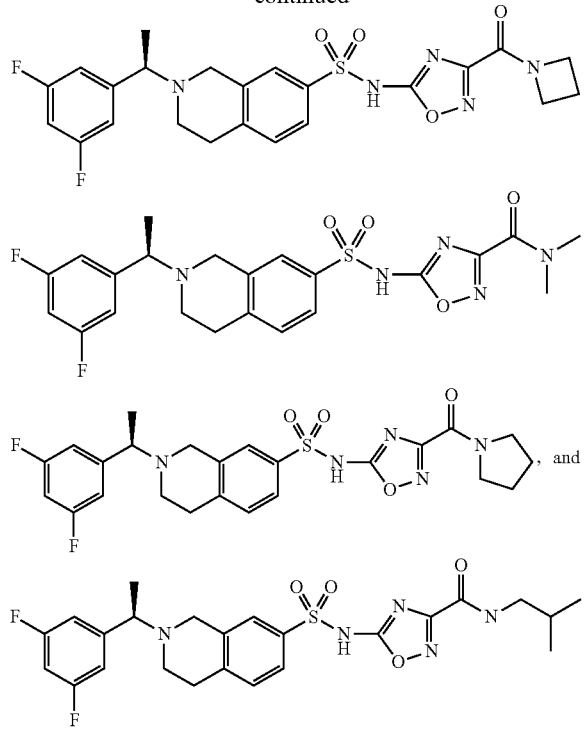

Definitions

The term "halogen" includes a fluorine atom, a chlorine atom, a bromine atom, and an iodine atom.

The term "—$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "—$C_1$-$C_6$alkoxy" refers to an alkyl group having 1 to 6 carbons linked to oxygen. Examples include methoxy, ethoxy, butoxy and propoxy.

The term "—$C_2$-$C_6$alkene" refers to as used herein, refers to an aliphatic hydrocarbon group containing at least one carbon-carbon double bond and may be straight or branched and contains from about 2 to about 6 carbon atoms. Non-limiting examples of alkenyl groups include ethenyl, propenyl, n-butenyl, 3-methylbut-2-enyl and n-pentenyl.

The term "halogen-substituted$C_1$-$C_6$ alkyl" refers to a $C_1$-$C_6$ alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

The term "halogen-substituted$C_1$-$C_6$alkoxy" refers to —O$C_1$-$C_6$alkyl as defined above, which is substituted with 1-3 halogen atoms which are identical or different, and specifically includes, for example, a trifluoromethoxy group.

The term "$C_1$-$C_6$alkylOH" refers to a $C_1$-$C_6$alkyl substituted with an alcohol (—OH). Examples include methanol, propanol, butanol and t-butanol.

The term "—COO$C_1$-$C_6$alkyl" refers to a —COOH group wherein the —OH is replaced with an alkoxy group as defined above. Examples include methoxycarbonyl, ethoxycarbonyl and butoxycarbonyl.

The term "—CONH$C_1$-$C_6$alkyl" refers to a group with one of the hydrogen atoms of carbamoyl (—CONH$_2$) being substituted with $C_{1-6}$ alkyl. Specific examples thereof include methylcarbamoyl, ethylcarbamoyl, n-propylcarbamoyl, isopropylcarbamoyl, n-butylcarbamoyl, sec-butylcarbamoyl, tert-butylcarbamoyl, and the like.

The term "—CON($C_1$-$C_6$alkyl)$_2$" refers to a group with the two carbamoyl hydrogen atoms each being independently substituted with a $C_{1-6}$ alkyl. Specific examples thereof include dimethylcarbamoyl, diethylcarbamoyl, ethylmethylcarbamoyl, di(n-propyl)carbamoyl, methyl(n-propyl)carbamoyl, diisopropylcarbamoyl, and the like.

The term "CONH-halogen-substituted-$C_1$-$C_6$alkyl" refers to a group with the two carbamoyl hydrogen atoms each being substituted with a halogen-substituted$C_{1-6}$ alkyl.

The term "NH$C_1$-$C_6$alkyl" refers to a group with one of the hydrogen atoms of amino (—NH$_2$) being substituted with a $C_{1-6}$ alkyl group. Specific examples thereof include methylamino, ethylamino, n-propylamino, isopropylamino, n-butylamino, sec-butylamino, tert-butylamino, and the like.

The term "$C_3$-$C_6$cycloalkyl" encompasses cycloalkyls having 3 to 8 carbons, forming one or more carbocyclic rings that are fused. "Cycloalkyl" also includes aromatic or "aryl" rings and non-aromatic rings as well as monocyclic, non-aromatic rings fused to an aryl group in which the point of attachment is on the non-aromatic portion. Examples of cycloalkyl include phenyl, naphthyl, cyclopropyl, cyclobutyl, cyclopentyl, cyclohexyl, cycloheptyl, tetrahydronaphthyl, decahydronaphthyl, indanyl and the like. Specific examples of "aryl" include phenyl, naphthyl, and the like.

The term "heterocycle" means mono- or bicyclic or bridged unsaturated, partially unsaturated and saturated rings containing at least one heteroatom selected from N, S and O, each of said ring having from 3 to 10 atoms in which the point of attachment may be carbon, N, S or O. Heterocycle includes heteroaromatic or "heteroaryl" rings and non-heteroaromatic rings as well as monocyclic, non-heteroaromatic rings fused to an heteroaryl group in which the point of attachment is on the non-aromatic portion. Examples thereof include pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzopyrazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl, pyrido[3,2-b]pyridyl, and the like. Examples also include tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, tetrahydropyran, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5- diazabicyclo[2.2.2]octyl, 2-azabicyclo[2.2.2]octyl, and 3-azabicyclo[3.2.2]nonyl, and azabicyclo[2.2.1]heptanyl.

The term "nitrogen-containing heterocycle" means mono- or bicyclic or bridged unsaturated, partially unsaturated and saturated rings containing at least one nitrogen, each of said ring having from 3 to 10 atoms in which the point of attachment may be carbon or nitrogen.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cos- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline Intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of the structural formulas described herein are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of the formulas described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula can be prepared without undue experimentation by conventional techniques well known to those skilled in the art or by processes analogous to those described in the Schemes and Examples herein using appropriate isotopically-enriched reagents and/or Intermediates.

Methods of Treatment

Also encompassed by the present invention are methods of treating MGAT2-related diseases. The compounds described herein are effective in preventing or treating various MGAT2-related diseases, such as metabolic diseases such as obesity, diabetes, hormone secretion disorder, hyperlipemia, gout, fatty liver, and the like; circulatory diseases such as angina pectoris, acute/congestive cardiac insufficiency, myocardial infarction, coronary arteriosclerosis, hypertension, nephropathy, electrolyte abnormality, and the like; central and peripheral nervous system diseases such as bulimia, affective disorder, depression, anxiety, epilepsy, delirium, dementia, schizophrenia, attention deficit/hyperactivity disorder, dysmnesia, somnipathy, cognitive impairment, dyskinesia, dysesthesia, dysosmia, morphine resistance, drug dependence, alcohol dependence, and the like; reproductive system diseases such as infertility, premature delivery, sexual dysfunction, and the like; and other conditions including digestive diseases, respiratory diseases, cancer, and chromatosis. The compound of the invention is especially useful as a preventive or a remedy for obesity, diabetes, fatty liver, bulimia, depression, or anxiety.

One aspect of the invention described herein provides a method for the treatment and control of obesity or metabolic syndrome, which comprises administering to a patient in need of such treatment a therapeutically effective amount of a compound having the formulas described herein or a pharmaceutically acceptable salt thereof. For example, the compounds described herein are useful for treating or preventing obesity by administering to a subject in need thereof a composition comprising a compound of Formula I.

Methods of treating or preventing obesity and conditions associated with obesity refer to the administration of the pharmaceutical formulations described herein to reduce or maintain the body weight of an obese subject or to reduce or maintain the body weight of an individual at risk of becoming obese. One outcome of treatment may be reducing the body weight of an obese subject relative to that subject's body weight immediately before the administration of the compounds or combinations of the present invention. Another outcome of treatment may be preventing body weight, regain of body weight previously lost as a result of diet, exercise, or pharmacotherapy and preventing weight gain from cessation of smoking. Another outcome of treatment may be decreasing the occurrence of and/or the severity of obesity-related diseases. Yet another outcome of treatment may be decreasing the risk of developing diabetes in an overweight or obese subject. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the pharmaceutical formulations described herein to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, type 2 diabetes, polycystic ovary disease, cardiovascular diseases, osteoarthritis, dermatological disorders, hypertension, insulin resistance, hypercholesterolemia, hypertriglyceridemia, and cholelithiasis.

Another aspect of the invention that is of interest relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound in accordance with the formulas described herein or a pharmaceutically acceptable salt thereof in an amount that is effective to treat type 2 diabetes.

Yet another aspect of the invention that is of interest relates to a method of treating non-insulin dependent diabetes mellitus in a mammalian patient in need of such treatment comprising administering to the patient a compound in accordance with the formulas described herein or a pharmaceutically acceptable salt thereof in an amount that is effective to treat non-insulin dependent diabetes mellitus.

The present invention is also directed to the use of a compound of structural Formula I or a pharmaceutically acceptable salt thereof in the manufacture of a medicament for use in treating various MGAT2-related diseases, such as metabolic diseases such as obesity, diabetes, hormone secretion disorder, hyperlipemia, gout, fatty liver, and the like; circulatory diseases such as angina pectoris, acute/congestive cardiac insufficiency, myocardial infarction, coronary arteriosclerosis, hypertension, nephropathy, electrolyte abnormality, and the like; central and peripheral nervous system diseases such as bulimia, affective disorder, depression, anxiety, epilepsy, delirium, dementia, schizophrenia, attention deficit/hyperactivity disorder, dysmnesia, somnipathy, cognitive impairment, dyskinesia, dysesthesia, dysosmia, morphine resistance, drug dependence, alcohol dependence, and the like; reproductive system diseases such as infertility, premature delivery, sexual dysfunction, and the like; and other conditions including digestive diseases, respiratory diseases, cancer, and chromatosis. The compounds described herein are especially useful as a preventive or a remedy for obesity, diabetes, fatty liver, bulimia, depression, or anxiety.

For example, the present invention is directed to the use of a compound of structural Formula I or a pharmaceutically acceptable salt thereof in the manufacture of a medicament for use in treating obesity, diabetes, hormone secretion disorder, hyperlipemia, gout and fatty liver.

Additionally, the present invention is directed to the use of a compound of structural Formula I or a pharmaceutically acceptable salt thereof in the manufacture of a medicament for use in treating diabetes.

Pharmaceutical Compositions

Compounds of the invention may be administered orally or parenterally. As formulated into a dosage form suitable for the administration route, the compound of the invention can be used as a pharmaceutical composition for the prevention, treatment, or remedy of the above diseases.

In clinical use of the compound of the invention, usually, the compound is formulated into various preparations together with pharmaceutically acceptable additives according to the dosage form, and may then be administered. By "pharmaceutically acceptable" it is meant the additive, carrier, diluent or excipient must be compatible with the other ingredients of the formulation and not deleterious to the recipient thereof. As such additives, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders, suppositories; and liquid preparations such as syrups, elixirs, injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9% by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. The dose is preferably from about 0.01 to about 25 mg/kg/day, more preferably from about 0.05 to about 10 mg/kg/day. For oral administration, the compositions are preferably provided in the form of tablets or capsules containing from 0.01 mg to 1,000 mg, preferably 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 and 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I or a pharmaceutically acceptable salt thereof. When a compound of Formula I is used contemporaneously with one or more other drugs, a pharmaceutical composition in unit dosage form containing such other drugs and the compound of Formula I or its pharmaceutically acceptable salt is preferred. However, the combination therapy may also include therapies in which the compound of Formula I or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I or a pharmaceutically acceptable salt thereof.

Examples of other active ingredients that may be administered in combination with a compound of Formula I or a pharmaceutically acceptable salt thereof and either administered separately or in the same pharmaceutical composition, include, but are not limited to:

(1) dipeptidyl peptidase-IV (DPP-4) inhibitors, such as, sitagliptin (disclosed in U.S. Pat. No. 6,699,871), vildagliptin, saxagliptin, alogliptin, denagliptin, carmegliptin, dutogliptin, melogliptin, linagliptin;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) insulin or insulin analogs, such as insulin lispro, insulin detemir, insulin glargine, insulin glulisine, and inhalable formulations of each thereof;

(4) leptin and leptin derivatives and agonists;

(5) amylin and amylin analogs, such as pramlintide;

(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof;

(12) antiobesity compounds such as topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and MK-0859;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin, canagliflozin, ertugliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR); and

(32) bromocriptine mesylate and rapid-release formulations thereof.

In another aspect of the invention, a pharmaceutical composition is disclosed which comprises one or more of the following agents:

(a) a compound of structural Formula I or a pharmaceutically acceptable salt thereof;

(b) one or more compounds selected from the group consisting of:

(1) dipeptidyl peptidase-IV (DPP-4) inhibitors;

(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(3) sulfonylurea and non-sulfonylurea insulin secretagogues, such as tolbutamide, glyburide, glipizide, glimepiride, mitiglinide, and meglitinides, such as nateglinide and repaglinide;

(4) α-glucosidase inhibitors (such as acarbose, voglibose and miglitol);

(5) glucagon receptor antagonists;

(6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(7) HDL-raising drugs, such as niacin or a salt thereof and extended-release versions thereof;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(11) glucokinase activators (GKAs), such as LY2599506;

(12) inhibitors of 11β-hydroxysteroid dehydrogenase type 1;

(13) inhibitors of cholesteryl ester transfer protein (CETP), such as torcetrapib and MK-0859;

(14) inhibitors of fructose 1,6-bisphosphatase;

(15) inhibitors of acetyl CoA carboxylase-1 or 2 (ACC1 or ACC2);

(16) AMP-activated Protein Kinase (AMPK) activators;

(17) agonists of the G-protein-coupled receptors: GPR-109, GPR-119, and GPR-40;

(18) SSTR3 antagonists;

(19) neuromedin U receptor agonists, including, but not limited to, neuromedin S (NMS);

(20) inhibitors of stearoyl-coenzyme A delta-9 desaturase (SCD);

(21) GPR-105 antagonists;

(22) inhibitors of glucose uptake, such as sodium-glucose transporter (SGLT) inhibitors and its various isoforms, such as SGLT-1; SGLT-2, such as dapagliflozin and remogliflozin; and SGLT-3;

(23) inhibitors of acyl coenzyme A:diacylglycerol acyltransferase 1 and 2 (DGAT-1 and DGAT-2);
(24) inhibitors of fatty acid synthase;
(25) inhibitors of acetyl-CoA carboxylase-1 and 2 (ACC-1 and ACC-2);
(26) inhibitors of acyl coenzyme A:monoacylglycerol acyltransferase 1 and 2 (MGAT-1 and MGAT-2);
(27) agonists of the TGR5 receptor (also known as GPBAR1, BG37, GPCR19, GPR131, and M-BAR); and
(28) bromocriptine mesylate and rapid-release formulations thereof; and
(c) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

EXAMPLES

The meanings of the abbreviations in Examples are shown below.
ACN=acetonitrile
ADH-RE=alcohol dehydrogenase from *Rhodococcus erythropolis*
i-Bu=isobutyl
n-Bu=n-butyl
t-Bu=tert-butyl
Boc=tert-butoxycarbonyl
CELITE=diatomaceous earth
DBPF=1,1'-bis(di$^t$butylphosphino)ferrocene
DCM=dichloromethane
DIBAL or DIBAL-H=diisobutylaluminium hydride
DIEA==DIPEA=N,N-Diisopropylethylamine
DMAP=4-Dimethylaminopyridine
DME=dimethoxyethane
DMF=N,N-Dimethylformamide
dba (or Pd$_2$(dba)$_3$=tris(dibenzylideneacetone)dipalladium (0)
Me=methyl
EDC=1-Ethyl-3-(3-dimethylaminopropyl)carbodiimide
Et=ethyl
EtOAc=ethyl acetate
GDH=glucose dehydrogenase
HOBt=hydroxybenzotriazole
$K_2CO_3$=potassium carbonate
LDH=lactic acid dehydrogenase
LHMDS=LiHMDS=lithium bis(trimethylsilyl)amide
MP-CNBH$_3$=MP cyanoborohydride (polymer supported reducing agent)
MgSO$_4$=magnesium sulfate
Ms=methanesulfonyl
MTBE=methyl tert-butyl ether
NAD=nicotinamide adenine dinucleotide
NADP=nicotinamide adenine dinucleotide phosphate
NaHCO$_3$=sodium bicarbonate
NH$_4$OH=Ammonium hydroxide
Ph=phenyl
i-Pr=isopropyl
n-Pr=n-propyl
Pd$_2$=
Sat.=saturated
SEMCl=2-(Trimethylsilyl) ethoxymethyl chloride
TBME=tert-butyl methyl ether
TEA=triethanolamine
TFA=trifluoroacetic acid
THF=tetrahydrofuran
TLC=thin layer chromatography
Xantphos=4,5-Bis(diphenylphosphino)-9,9-dimethylxanthene
CDCl3=heavy chloroform
CD3OD=heavy methanol
DMSO-d6=heavy dimethylsulfoxide The meanings of the abbreviations in the nuclear magnetic resonance spectra are shown below.
s=singlet
d=doublet
dd=double doublet
dt=double triplet
ddd=double double doublet
Sept=septet
t=triplet
m=multiplet
br=broad
brs=broad singlet
q=quartet
J=coupling constant
Hz=hertz Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a WATERS Micromass® ZQ™ with electrospray ionization in positive ion detection mode. High performance liquid chromatography (HPLC) was conducted on an AGILENT 1100 series HPLC on WATERS C18 XTERRA 3.5 µm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm). Concentration of solutions was carried out on a rotary evaporator under reduced pressure. Flash chromatography was performed using a BIOTAGE Flash Chromatography apparatus (Dyax Corp.) on silica gel (32-63 mM, 60 Å pore size) in pre-packed cartridges. $^1$H-NMR spectra were obtained on a 400 or 500 MHz VARIAN Spectrometer in CDCl$_3$ or CD$_3$OD or other solvents as indicated and chemical shifts are reported as δ using the solvent peak as reference and coupling constants are reported in hertz (Hz).

In general, compounds of Formula I were synthesized according to Scheme 1 or 2. In Scheme 1, tetrahydroisoquinoline 1 (T was Br or I) was converted to sulfide 2 where the amine was protected to provide 4 (P=protecting group). Alternatively, protection of the amine to give 3 was followed by sulfide formation, which also gave 4. Sulfide 4 was oxidized to give sulfonyl chloride 5, which reacted with amine 6 to provide sulfonamide 7. Deprotection followed by either reductive amination with aldehyde 9 or $S_{N2}$ type displacement with compound 10 (LG=leaving group) completed synthesis.

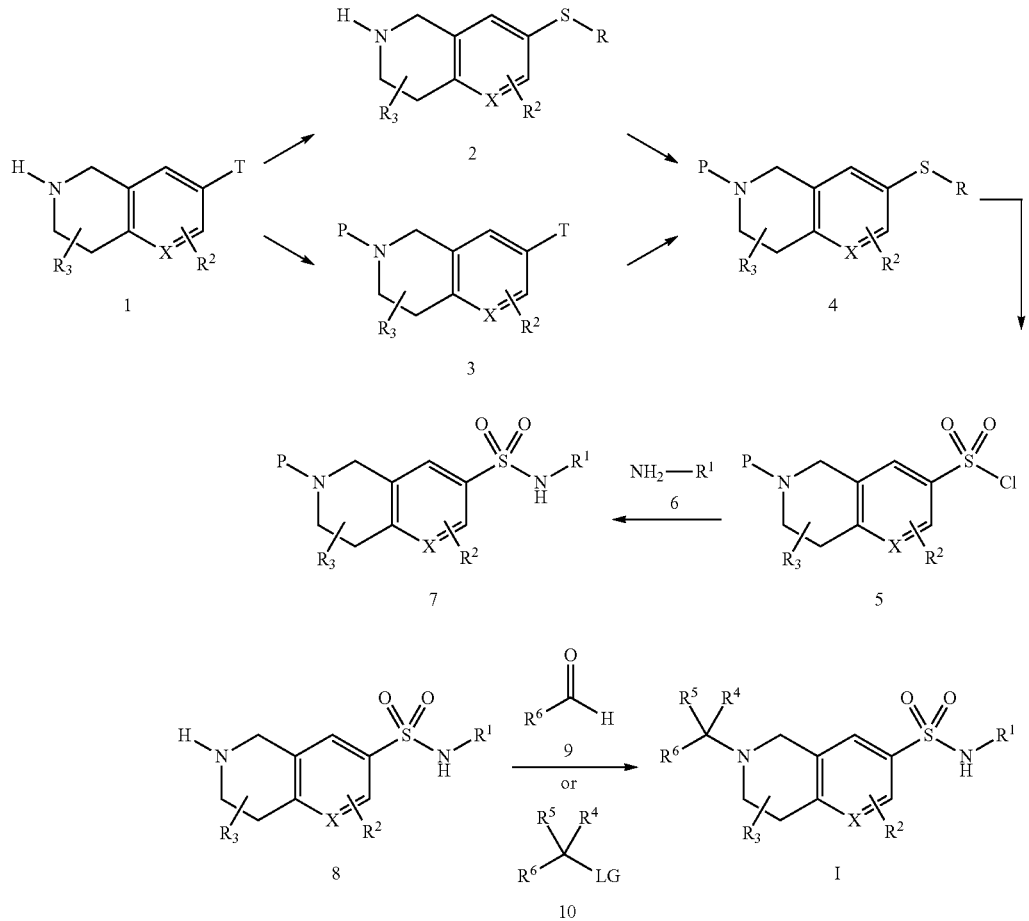

Scheme 1

In Scheme 2, double $S_{N2}$ type reaction between amine 11 and compound 12 where LG was a leaving group provided the cyclication product tetrahydroisoquinoline 13. Conversion of 13 to sulfide 14 and in turn to sulfonyl chloride 15 was followed by sulfonamide formation completed the synthesis of compounds of Formula I.

Scheme 2

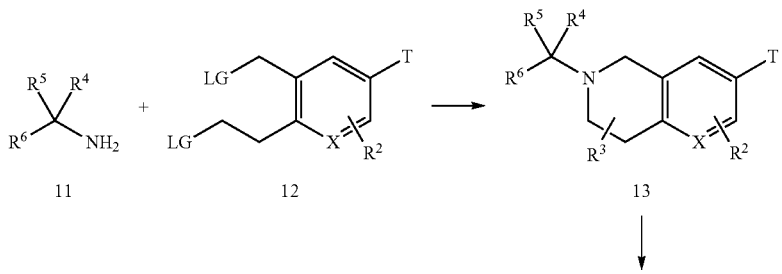

-continued

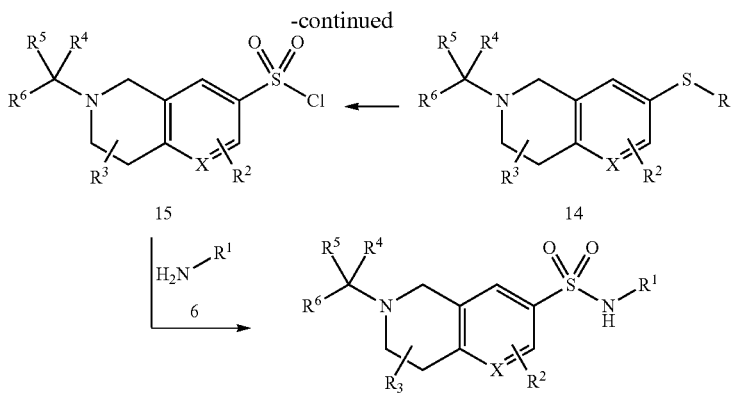

Intermediate 1

N-(5-(tert-Butyl)isoxazol-3-yl)-N-((2-(trimethylsilyl)ethoxy)methyl)-1,2,3,4-tetrahydroisoquinoline-7-sulfonamide

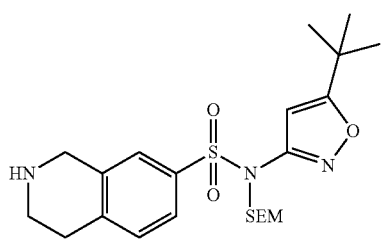

Step A: 1-(7-(benzylthio)-3,4-dihydroisoquinolin-2(1H)-yl)-2,2,2-trifluoroethanone

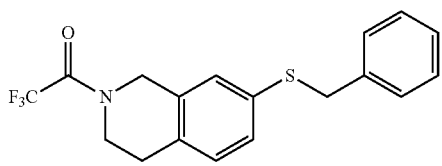 [SMILES: O=C(N1CCc2ccc(SCc3ccccc3)cc2C1)C(F)(F)F]

Benzyl mercaptan (5.63 ml, 47.6 mmol) was introduced to a solution of 1-(7-bromo-3,4-dihydroisoquinolin-2(1H)-yl)-2,2,2-trifluoroethanone (14.5 g, 47.2 mmol), DIEA (16.6, 95 mmol), Pd$_2$(dba)$_3$ (0.86 g, 0.94 mmol), and Xantphos (1.64 g, 2.83 mmol) in anhydrous 1,4-dioxane (200 ml) that had been degassed with N$_2$ for 10 min. The flask was fitted with a reflux condensor, evacuated and backfilled with N$_2$×2, and the mixture refluxed at 102° C. for 2 hrs. The reaction mixture was cooled to room temperature and filtered through a fritted funnel. The filtrate was concentrated under reduced pressure then taken up in EtOAc, washed with water, dried over MgSO$_4$, filtered, and concentrated under reduced pressure. The obtained crude material was purified by flash column (340 g, SNAP, 5~10% EtOAc in hexane) to afford the title compound as an orange oil. LC/MS (m/z): 352 (M+H)$^+$.

Step B: 2-(2,2,2-trifluoroacetyl)-1,2,3,4-tetrahydroisoquinoline-7-sulfonyl chloride

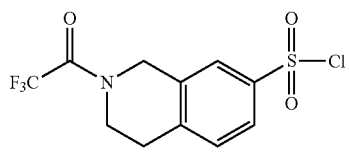 [SMILES: O=C(N1CCc2ccc(S(=O)(=O)Cl)cc2C1)C(F)(F)F]

Sulfuryl chloride (2 ml, 24.6 mmol) was added dropwise to a solution of 1-(7-(benzylthio)-3,4-dihydroisoquinolin-2(1H)-yl)-2,2,2-trifluoroethanone (2.27 g, 6.46 mmol), water (0.5 ml, 27.8 mmol), and acetic acid (1.5 ml, 26.2 mmol) in DCM (30 ml) that had been cooled to 0° C. in an ice bath and degassed with N$_2$ for 10 min. The ice bath was removed and the mixture stirred at room temperature for 4 hrs. The solution was quenched with saturated aqueous NaHCO$_3$ solution and the layers cut. The aqueous phase was extracted with DCM×3 and the combined organic layers dried over MgSO$_4$, filtered then concentrated under reduced pressure. The obtained crude material was purified by flash column (50 g, SNAP, 10~30% EtOAc in hexane) to afford the title compound as a white solid. LC/MS (m/z): 327 (M+H)$^+$.

Step C: N-(5-(tert-butyl)isoxazol-3-yl)-2-(2,2,2-trifluoroacetyl)-1,2,3,4-tetrahydroisoquinoline-7-sulfonamide

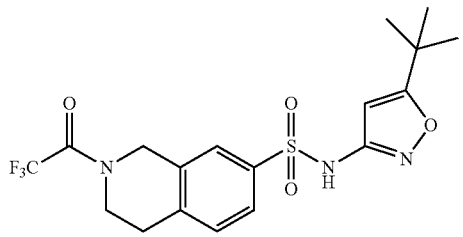 [SMILES: CC(C)(C)c1cc(NS(=O)(=O)c2ccc3c(c2)CN(C(=O)C(F)(F)F)CC3)no1]

3-amino-5-tert-butylisoxazole (1.05703 g, 7.54 mmol) was added to a solution of 2-(2,2,2-trifluoroacetyl)-1,2,3,4-tetrahydroisoquinoline-7-sulfonyl chloride (2.4702 g, 7.54 mmol) in anhydrous THF (20 ml) followed by pyridine (0.62 ml, 7.67 mmol). The reaction was stirred for 2 h, at which time, TLC (30% EtOAc/hexanes) showed a mixture of two products: minor one cospots with starting material, the major product was of a lower retardation factor (Rf). The reaction was partitioned between EtOAc and 2 N HCl. The organic layer was washed with brine, dried over MgSO₄, and concentrated in vacuo. The product was purified by ISCO COMBIFLASH chromatography (80 g silica gel, 60 mL/min., 254 nm, 0-100% EtOAc/hexane over 16 column volumes (CV). ¹H NMR (500 MHz, CDCl₃) δ 7.80-7.90 (bs, 1H), 7.30 (2d, 1H), 7.61-7.69 (2s, 1H), 7.70-7.74 (2d, 1H), 7.22-7.36 (m, 3H), 7.20 (d, 1H), 6.19 (s, 1H), 4.78-4.80 (2s, 2H), 3.82-3.93 (2m, 2H), 3.00 (m, 2H), 1.33 (2s, 9H).

Step D: N-(5-(tert-butyl)isoxazol-3-yl)-2-(2,2,2-trifluoroacetyl)-N-((2-(trimethylsilyl)ethoxy)methyl)-1,2,3,4-tetrahydroisoquinoline-7-sulfonamide

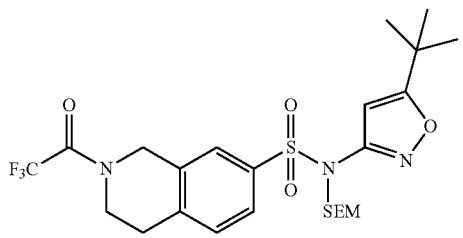 [SMILES: CC(C)(C)c1cc(N(COCC[Si](C)(C)C)S(=O)(=O)c2ccc3c(c2)CN(C(=O)C(F)(F)F)CC3)no1]

NaH (0.3875 g, 16.15 mmol) was added to a solution of N-(5-(tert-butyl)isoxazol-3-yl)-2-(2,2,2-trifluoroacetyl)-1,2,3,4-tetrahydroisoquinoline-7-sulfonamide (3.9904 g, 9.25 mmol) in anhydrous DMF (30 ml) at 0° C. under N₂. After the gas evolution ceased, SEMCl (1.8 ml, 10.15 mmol) was added dropwise to the reaction. The reaction was allowed to warm to ambient temperature after addition. After 22 h, the reaction was recooled to 0° C. and an additional 0.2671 g of sodium hydride was added followed by 1.0 mL of SEMCl to drive reaction to completion. The reaction was allowed to warm to ambient temperature and stirred for 3 h. Slight progression was observed by TLC (30% EtOAc/hexanes). The reaction was partitioned between EtOAc and water. The aqueous layer was back-extracted with EtOAc. The organic layers were combined, washed with brine, dried over MgSO₄, and concentrated in vacuo. The residue was purified by ISCO COMBIFLASH chromatography (120 g silica gel, 85 mL/min, 254 nM, 0% to 100% EtOAc/hexanes over 16 CV, desired product elutes at 30% EtOAc/hexanes) to give the desired product as a 2:1 mixture of rotamers. LC/MS (m/z): 562 (M+H)⁺

Step E: N-(5-(tert-butyl)isoxazol-3-yl)-N-((2-(trimethylsilyl)ethoxy)methyl)-1,2,3,4-tetrahydroisoquinoline-7-sulfonamide

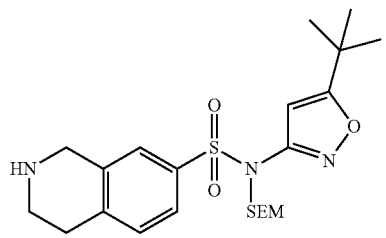 [SMILES: CC(C)(C)c1cc(N(COCC[Si](C)(C)C)S(=O)(=O)c2ccc3c(c2)CNCC3)no1]

Concentrated NH₄OH (5 mL) was added to a solution of N-(5-(tert-butyl)isoxazol-3-yl)-2-(2,2,2-trifluoroacetyl)-N-((2-(trimethylsilyl)ethoxy)methyl)-1,2,3,4-tetrahydroisoquinoline-7-sulfonamide (4.8165 g, 8.58 mmol) in MeOH (40 mL) at room temperature The reaction was capped and stirred for 15 h. LC/MS showed little starting material which was confirmed by TLC (30% EtOAc/hexanes). The reaction was concentrated in vacuo and the residue was purified by ISCO COMBIFLASH (40 g SUPELCO MCI GEL CHP20P, 40 mL/min, 210 nM, 0% to 100% MeOH/water over 29 minutes; desired product elutes at 100% MeOH). The desired fractions were collected and lyophilized overnight. ¹H NMR (500 MHz, CDCl₃) δ 7.68 (d, 1H), 7.59 (s, 1H), 7.21 (d, 1H), 6.21 (s, 1H), 4.08 (s, 2H), 3.67 (t, 2H), 3.20 (t, 2H), 2.90 (t, 2H), 1.35 (s, 9H), 0.96 (t, 2H), 0.00 (s, 9H). LC/MS (m/z): 466 (M+H)⁺

Intermediate 2

2-((6-(2,2,2-Trifluoroethoxy)pyridin-3-yl)methyl)-1,2,3,4-tetrahydroisoquinoline-7-sulfonyl Chloride

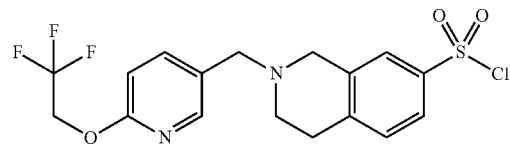 [SMILES: O=S(=O)(Cl)c1ccc2c(c1)CN(Cc1ccc(OCC(F)(F)F)nc1)CC2]

Step A:
7-(benzylthio)-1,2,3,4-tetrahydroisoquinoline

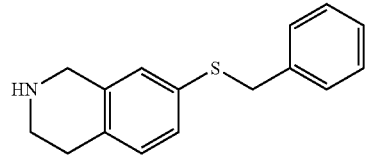 [SMILES: c1ccc(CSc2ccc3c(c2)CNCC3)cc1]

Benzyl mercaptan (7.67 ml, 64.8 mmol) was introduced to a solution of 7-bromo-1,2,3,4-tetrahydroisoquinoline (12.5 g, 58.9 mmol), DIEA (21.6 ml, 124 mmol), Pd₂(dba)₃ (0.27 g, 0.295 mmol), and Xantphos (0.682 g, 1.18 mmol) in anhydrous 1,4-dioxane (236 ml) that had been degassed with N₂ for 10 min. The flask was fitted with a reflux condensor, evacuated and backfilled with N₂×2, and the mixture refluxed at 110° C. for 2 hrs. The reaction mixture was cooled to room temperature and filtered through a fritted funnel. The filtrate was concentrated under reduced pressure then taken up in EtOAc, washed with water, dried over MgSO₄, filtered, and concentrated under reduced pressure to afford the crude title compound. LC/MS (m/z): 256 (M+H)⁺.

Step B: 7-(benzylthio)-2-((6-(2,2,2-trifluoroethoxy)pyridin-3-yl)methyl)-1,2,3,4-tetrahydroisoquinoline

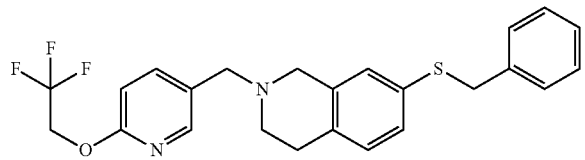 [SMILES: FC(F)(F)COc1ccc(CN2CCc3ccc(SCc4ccccc4)cc3C2)cn1]

Resin-bound tetra-alkylcyanoborohydride (9.03 g, 21.2 mmol) was added to a preformed mixture of 7-(benzylthio)-1,2,3,4-tetrahydroisoquinoline (4 g, 14.1 mmol), 6-(2,2,2-trifluoroethoxy)nicotinaldehyde (3.18 g, 15.5 mmol), and glacial acetic acid (3.23 ml, 56.4 mmol) in MeOH (35 ml). The reaction vessel was fitted with a reflux condenser and heated to 40° C. overnight. The reaction mixture was cooled to room temperature, filtered through a fritted funnel, then neutralized by the addition of saturated aqueous NaHCO$_3$ solution. The layers were cut and the aqueous phase extracted with EtOAc×3. The combined organic layers were dried over MgSO$_4$, filtered, and concentrated under reduced pressure. The residue was purified by medium pressure liquid chromatography "MPLC" (KP-Sil 100 g SNAP column, BIOTAGE system) eluting with 1% MeOH/DCM over 3 CV followed by a gradient of 6-9% MeOH/DCM over 8 CV to give the desired compound. LC/MS (m/z): 445 (M+H)$^+$.

Step C: 2-((6-(2,2,2-trifluoroethoxy)pyridin-3-yl)methyl)-1,2,3,4-tetrahydroisoquinoline-7-sulfonyl Chloride

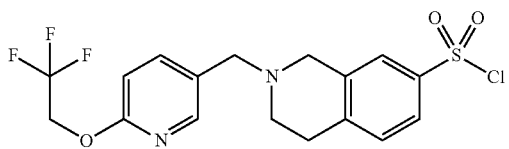 [SMILES: O=S(=O)(Cl)c1ccc2c(c1)CN(Cc1ccc(OCC(F)(F)F)nc1)CC2]

Sulfuryl chloride (3.73 ml, 45.9 mmol) was added dropwise to a solution of 7-(benzylthio)-2-((6-(2,2,2-trifluoroethoxy)pyridin-3-yl)methyl)-1,2,3,4-tetrahydroisoquinoline (5.1 g, 11.5 mmol), water (0.827 ml, 45.9 mmol), and acetic acid (2.63 ml, 45.9 mmol) in DCM (46 ml) that had been cooled to 0° C. in an ice bath and degassed with N$_2$ for 10 min. The ice bath was removed and the mixture stirred at room temperature for 4 hrs. The solution was quenched with saturated aqueous NaHCO$_3$ solution and the layers cut. The aqueous phase was extracted with DCM×3 and the combined organic layers dried over MgSO$_4$, filtered, then concentrated under reduced pressure to afford the crude title compound. LC/MS (m/z): 421 (M+H)$^+$.

Intermediate 3

(R)-2-(1-(6-(2,2,2-Trifluoroethoxy)pyridin-3-yl)ethyl)-1,2,3,4-tetrahydroisoquinoline-7-sulfonyl Chloride

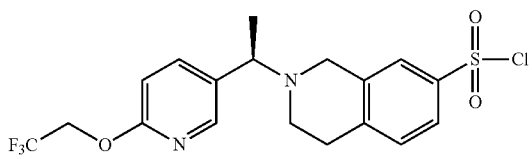 [SMILES: C[C@H](c1ccc(OCC(F)(F)F)nc1)N1CCc2ccc(S(=O)(=O)Cl)cc2C1]

Step A: (R)-7-bromo-2-(1-(6-(2,2,2-trifluoroethoxy)pyridin-3-yl)ethyl)-1,2,3,4-tetrahydroisoquinoline

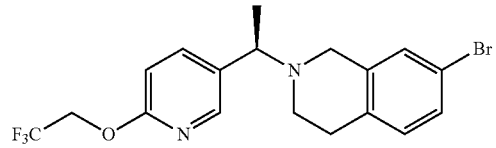 [SMILES: C[C@H](c1ccc(OCC(F)(F)F)nc1)N1CCc2ccc(Br)cc2C1]

(R)-1-(6-(2,2,2-trifluoroethoxy)pyridin-3-yl)ethanamine (10 g, 45.4 mmol) and 4-bromo-1-(2-bromoethyl)-2-(bromomethyl)benzene (16.2 g, 45.4 mmol) were dissolved in EtOH (100 mL) and K$_2$CO$_3$ (18.8 g, 136 mmol) was added. The mixture was heated at 86° C. for 3 h. The reaction was cooled to room temperature, filtered through a fritted funnel, washed with EtOAc. The filtrate was evaporated under reduced pressure. The obtained crude material was purified by flash column (340 g, SNAP, 5~20% EtOAc in hexanes) to afford the title compound. LC/MS (m/z): 416 (M+H)$^+$.

Step B: (R)-7-(benzylthio)-2-(1-(6-(2,2,2-trifluoroethoxy)pyridin-3-yl)ethyl)-1,2,3,4-tetrahydroisoquinoline

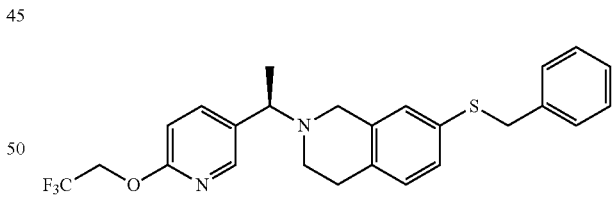

Benzyl mercaptan (2.99 ml, 25.3 mmol) was introduced to a solution of (R)-7-bromo-2-(1-(6-(2,2,2-trifluoroethoxy)pyridin-3-yl)ethyl)-1,2,3,4-tetrahydroisoquinoline (10.5 g, 25.3 mmol), DIEA (8.83 ml, 50.6 mmol), Pd$_2$(dba)$_3$ (0.58 g, 0.632 mmol), and Xantphos (1.02 g, 1.77 mmol) in anhydrous 1,4-dioxane (120 ml) that had been degassed with N$_2$ for 10 min. The flask was fitted with a reflux condensor, evacuated and backfilled with N$_2$×2, and the mixture refluxed at 105° C. for 3 hrs. The reaction was cooled to room temperature and filtered through a fritted funnel. The filtrate was concentrated under reduced pressure then taken up in EtOAc, washed with water, dried over MgSO$_4$, filtered, and concentrated under reduced pressure. The obtained crude material was purified by flash column (340 g, SNAP, 5~20% EtOAc in hexanes) to afford the title compound. LC/MS (m/z): 459 (M+H)+.

Step C: (R)-2-(1-(6-(2,2,2-trifluoroethoxy)pyridin-3-yl)ethyl)-1,2,3,4-tetrahydroisoquinoline-7-sulfonyl Chloride

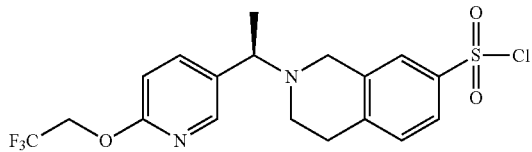 [SMILES: C[C@H](c1ccc(OCC(F)(F)F)nc1)N1CCc2ccc(S(=O)(=O)Cl)cc2C1]

Sulfuryl chloride (5.6 ml, 68.9 mmol) was added dropwise to a solution of (R)-7-(benzylthio)-2-(1-(6-(2,2,2-trifluoroethoxy)pyridin-3-yl)ethyl)-1,2,3,4-tetrahydroisoquinoline (7.9 g, 17.2 mmol), water (1.24 ml, 68.9 mmol), and acetic acid (3.95 ml, 68.9 mmol) in DCM (150 ml) that had been cooled to 0° C. in an ice bath and degassed with $N_2$ for 10 min. The ice bath was removed and the mixture stirred at room temperature for 4 hrs. The solution was quenched with saturated aqueous NaHCO$_3$ solution and the layers cut. The aqueous phase was extracted with DCM×3 and the combined organic layers dried over MgSO$_4$, filtered then concentrated under reduced pressure to afford the crude title compound. LC/MS (m/z): 435 (M+H)+.

Intermediate 4

(R)-2-(1-(5-(2,2,2-Trifluoroethoxy)pyrazin-2-yl)ethyl)-1,2,3,4-tetrahydroisoquinoline-7-sulfonyl Chloride

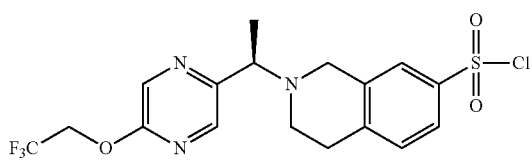

Step A:
5-chloro-N-methoxy-N-methylpyrazine-2-carboxamide

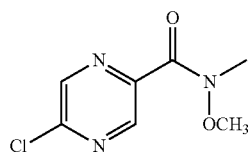

Catalytic (cat.) DMF (0.2 mL) was added to the mixture of 5-chloropyrazine-2-carboxylic acid (5 g, 31.5 mmol) in thionyl chloride (30 mL). The mixture was heated to reflux at 85° C. under $N_2$ for 3 h, then it was evaporated and dissolved in DCM (100 mL) followed by addition of N,O-dimethylhydroxylamine hydrochloride (4.61 g, 47.3 mmol). The mixture was cooled to 0° C. and stirred at this temperature for 5 min and triethylamine (13.2 mL, 95 mmol) was added dropwise. The reaction was warmed to room temperature and stirred overnight. The mixture was washed with saturated NaHCO$_3$, brine, dried over MgSO$_4$, evaporated. The crude material was purified by flash column (100 g SNAP, 25~50% EtOAc in hexanes) to afford the title compound. LC/MS (m/z): 202 (M+H)+.

Step B: 1-(5-chloropyrazin-2-yl)ethanone

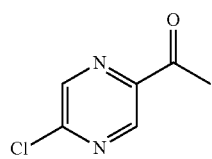

MeMgBr (3 M, 11.53 mL in hexanes) was added dropwise to a solution of 5-chloro-N-methoxy-N-methylpyrazine-2-carboxamide (5.81 g, 28.8 mmol) in THF (50 mL) at −10° C. The mixture was allowed to warm slowly to room temperature and stirred for 30 min. The reaction was quenched with sat. NH$_4$Cl, extracted with EtOAc. The organic phase was washed with brine, dried over MgSO$_4$, and evaporated. This crude material was purified by flash column (50 g SNAP, 10~20% EtOAc in hexanes) to afford the title compound. LC/MS (m/z): 157 (M+H)+.

Step C:
1-(5-(2,2,2-trifluoroethoxy)pyrazin-2-yl)ethanone

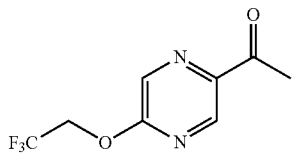

1-(5-Chloropyrazin-2-yl)ethanone (2.8 g, 17.9 mmol) was dissolved in DMF (30 mL) and CF$_3$CH$_2$OH was added followed by the addition of NaH (1.07 g, 26.8 mmol, 60% dispersion) at 0° C. The mixture was stirred at 0° C. for 10 min. The reaction was quenched with sat. NH$_4$Cl, extracted with EtOAc, dried over MgSO$_4$, and evaporated. The crude material was purified by flash column (50 g SNAP, 8~20% EtOAc in hexane) to afford the title compound. LC/MS (m/z): 221 (M+H)+.

Step D: (R)-1-(5-(2,2,2-trifluoroethoxy)pyrazin-2-yl)ethanamine

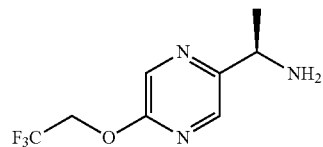

CDX-017 transaminase (1.25 g) (available from CODEXIS) and pyridoxal-phosphate "PLP" (150 mg) were added to the Buffer (0.2 M, 90 mL) and the mixture was stirred at 40° C. for 5 min. Then 1-(5-(2,2,2-trifluoroethoxy)pyrazin-2-yl)ethanone (1.25 g, 5.68 mmol) in DMSO (10 mL) was added followed by the addition of 10 mL of isopropylamine. The mixture was stirred at 40° C. overnight. The reaction mixture was extracted with EtOAc (3×), dried over MgSO₄, evaporated to afford the title compound. LC/MS (m/z): 222 (M+H)⁺.

Step E: (R)-7-bromo-2-(1-(5-(2,2,2-trifluoroethoxy) pyrazin-2-yl)ethyl)-1,2,3,4-tetrahydroisoquinoline

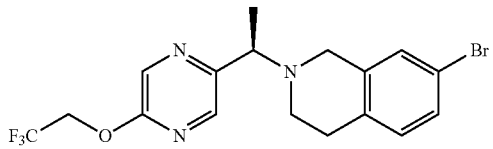

(R)-1-(5-(2,2,2-trifluoroethoxy)pyrazin-2-yl)ethanamine (1.2 g, 5.43 mmol) and 4-bromo-1-(2-bromoethyl)-2-(bromomethyl)benzene (1.94 g, 5.43 mmol) were dissolved in EtOH (20 mL) and K₂CO₃ (2.25 g, 16.3 mmol) was added. The mixture was heated at 86° C. for 2 h. The reaction was cooled to room temperature, filtered through a fritted funnel, and washed with EtOAc. The filtrate was evaporated under reduced pressure. The obtained crude material was purified by flash column (25 g, S-Nitroso-N-acetylpenicillamine, 6~20% EtOAc in hexane) to afford the title compound. LC/MS (m/z): 416 (M+H)⁺.

Step F: (R)-7-(benzylthio)-2-(1-(5-(2,2,2-trifluoroethoxy)pyrazin-2-yl)ethyl)-1,2,3,4-tetrahydroisoquinoline

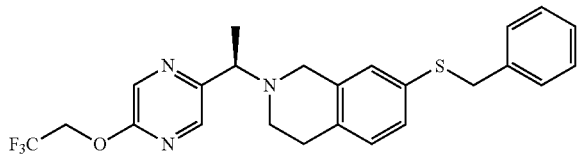

Benzyl mercaptan (0.5 ml, 4.2 mmol) was introduced to a solution of (R)-7-bromo-2-(1-(5-(2,2,2-trifluoroethoxy)pyrazin-2-yl)ethyl)-1,2,3,4-tetrahydroisoquinoline (1.75 g, 4.2 mmol), DIEA (1.47 ml, 8.41 mmol), Pd₂(dba)₃ (96 mg, 0.1 mmol), and Xantphos (170 mg, 0.29 mmol) in anhydrous 1,4-dioxane (20 ml) that had been degassed with N₂ for 10 min. The flask was fitted with a reflux condensor, evacuated and backfilled with N₂×2, and the mixture refluxed at 105° C. for 4 hrs. The reaction mixture was cooled to room temperature and filtered through a fritted funnel. The filtrate was concentrated under reduced pressure then taken up in EtOAc, washed with water, dried over MgSO₄, filtered, and concentrated under reduced pressure. The obtained crude material was purified by flash column (50 g, SNAP, 5~20% EtOAc in hexane) to afford the title compound. LC/MS (m/z): 460 (M+H)⁺.

Step G: (R)-2-(1-(5-(2,2,2-trifluoroethoxy)pyrazin-2-yl)ethyl)-1,2,3,4-tetrahydroisoquinoline-7-sulfonyl Chloride

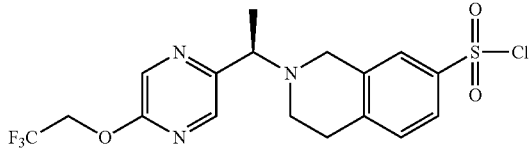 [SMILES: C[C@H](c1cnc(OCC(F)(F)F)cn1)N1CCc2ccc(S(=O)(=O)Cl)cc2C1]

Sulfuryl chloride (1.35 ml, 16.54 mmol) was added dropwise to a solution of (R)-7-(benzylthio)-2-(1-(5-(2,2,2-trifluoroethoxy)pyrazin-2-yl)ethyl)-1,2,3,4-tetrahydro-isoquinoline (1.9 g, 4.13 mmol), water (0.3 ml, 16.54 mmol), and acetic acid (0.95 ml, 16.54 mmol) in DCM (40 ml) at room temperature and degassed with N₂ for 10 min. The mixture was stirred at room temperature for 4 hrs. The solution was quenched with saturated aqueous NaHCO₃ solution and the layers cut. The aqueous phase was extracted with DCM×3 and the combined organic layers dried over MgSO₄, filtered then concentrated under reduced pressure to afford crude title compound. LC/MS (m/z): 436 (M+H)⁺.

Intermediate 5

(R)-2-(1-(3,5-difluorophenyl)ethyl)-1,2,3,4-tetrahydroisoquinoline-7-sulfonyl Chloride

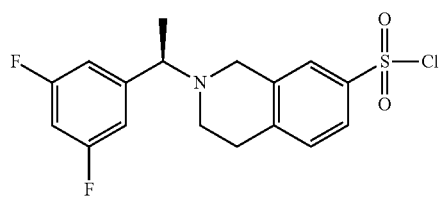 [SMILES: C[C@H](c1cc(F)cc(F)c1)N1CCc2ccc(S(=O)(=O)Cl)cc2C1]

Intermediate 5 was prepared starting with chiral amine, (R)-1-(3,5-difluoropheny)ethanamine, and following similar procedure as described for Intermediate 3. LC/MS (m/z): 372 (M+H)⁺.

Intermediate 6

(R)-2-(1-(5-(2,2,2-Trifluoroethoxy)pyrazin-2-yl)ethyl)-1,2,3,4-tetrahydroisoquinoline-7-sulfonyl Chloride

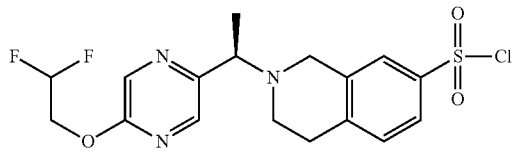 [SMILES: C[C@H](c1cnc(OCC(F)F)cn1)N1CCc2ccc(S(=O)(=O)Cl)cc2C1]

Intermediate 6 was prepared following the procedure described for Intermediate 4 but replacing trifluoroethanol with difluoroethanol in Step C. LC/MS (m/z): 418 (M+H)⁺.

Example 1

Preparation of (R)—N-(5-(tert-butyl)isoxazol-3-yl)-2-(1-(3-chlorophenyl)ethyl)-1,2,3,4-tetrahydroisoquinoline-7-sulfonamide

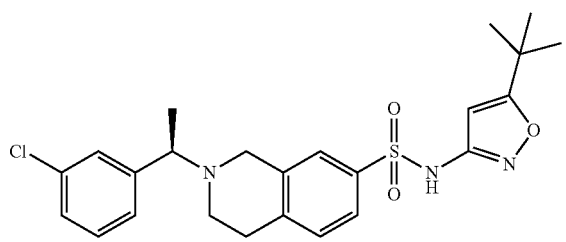 [SMILES: C[C@H](c1cccc(Cl)c1)N1CCc2ccc(S(=O)(=O)Nc3cc(C(C)(C)C)on3)cc2C1]

Step A: (S)-1-(3-chlorophenyl)ethanol

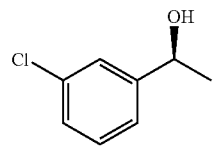

A stock solution of 9 g Glucose (25 g/L), 1.10 g ADH-RE (3 g/L), 360 mg NAD (1 g/L), 720 mg GDH (2 g/L), and 360 mg LDH (1 g/L) in 360 mL 0.1M phosphate buffer was prepared beforehand. 90 mL of the stock solution was quickly added to a solution of 1-(3-chlorophenyl)ethanone (1.0 g, 6.5 mmol) in 10 mL of DMSO, and stirred overnight at 30° C. The reaction showed >98% conversion and >99% e.e. by HPLC [ZORBAX Eclipse Plus C18 50×4.6 mm, 1.8 uM, 10% to 95% B (A=0.1% phosphoric acid, B=acetonitrile), 1.5 mL/min., 210 nM, 25 C, 8 min. run time]; therefore, 100 mL of MTBE was added followed by 2 mL of 5N NaOH. The reaction was agitated, centrifuged, and separated. The aqueous layer was re-extracted with 50 mL of MTBE followed by agitation, centrifuge, and separation. The MTBE layers were combined and washed with 50 mL of brine, dried with $Na_2SO_4$, filtered, and concentrated in vacuo. The residue was purified by ISCO COMBIFLASH chromatography (12 g silica gel, 30 mL/min, 254 nM, 0% to 100% EtOAc/hexane over 24 CV. The desired product elutes at 22% EtOAc/hexane).

Step B: (S)-1-(3-chlorophenyl)ethyl Methanesulfonate

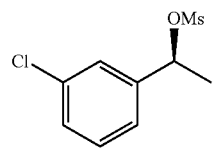

Triethylamine (0.254 ml, 1.821 mmol) was added to a solution of (S)-1-(3-chlorophenyl)ethanol (0.1426 g, 0.911 mmol) in $CH_2Cl_2$ (2 ml), followed by Ms-Cl (0.085 ml, 1.093 mmol) at 0° C. After the addition, the reaction was allowed to warm to ambient temperature. The resulting mixture was stirred for 45 minutes. $^1$H NMR of an aliquot showed complete conversion to the desired product. The reaction was partitioned between EtOAc and water/brine. The organic layer was collected, dried over $MgSO_4$, and concentrated in vacuo to give an oil which was used as is without further purification. $^1$H NMR (500 MHz, $CDCl_3$) δ (ppm): 7.28-7.43 (m, 4H), 5.73 (q, 1H), 2.82 (s, 3H), 1.77 (d, 3H).

Step C: (R)—N-(5-(tert-butyl)isoxazol-3-yl)-2-(1-(3-chlorophenyl)ethyl)-N-((2-(trimethylsilyl)ethoxy)methyl)-1,2,3,4-tetrahydroisoquinoline-7-sulfonamide

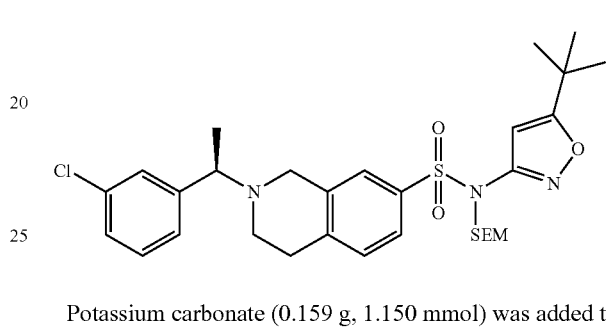

Potassium carbonate (0.159 g, 1.150 mmol) was added to a mixture of N-(5-(tert-butyl)isoxazol-3-yl)-N-((2-(trimethylsilyl)ethoxy)methyl)-1,2,3,4-tetrahydroisoquinoline-7-sulfonamide (Intermediate 1, 0.2177 g, 0.467 mmol) and (S)-1-(3-chlorophenyl)ethyl methanesulfonate (0.108 g, 0.46 mmol) in $CH_3CN$ (2 mL). The reaction was heated to 80° C. in a sealed microwave vial. The reaction was heated for a total of 17 h, being monitored by LC/MS. The reaction was concentrated in vacuo and partitioned between EtOAc and water. The organic layer was washed with brine, dried over sodium sulfate, and concentrated in vacuo. The residue was purified by ISCO COMBIFLASH chromatography (12 g silica gel, 30 mL/min, 254 nM, 0% to 100% EtOAc/hexane over 28 CV), the desired product eluting at 28% EtOAc/hexane. $^1$H NMR (500 MHz, $CDCl_3$) δ 7.63 (dd, 1H), 7.58 (s, 1H), 7.39 (s, 1H), 7.22-7.36 (m, 3H), 7.20 (d, 1H), 6.21 (s, 1H), 5.30 (s, 2H), 3.81 (d, 1H), 3.67 (t, 2H), 3.55-3.61 (m, 3H), 2.61-3.97 (m, 4H), 1.42 (d, 3H), 1.35 (s, 9H), 0.93 (t, 2H), 0.00 (s, 9H). LC/MS (m/z): 604 (M+H)$^+$ Step D: (R)—N-(5-(tert-butyl)isoxazol-3-yl)-2-(1-(3-chlorophenyl)ethyl)-1,2,3,4-tetrahydroisoquinoline-7-sulfonamide

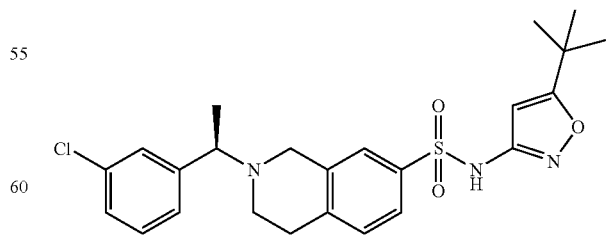

A solution of (R)—N-(5-(tert-butyl)isoxazol-3-yl)-2-(1-(3-chlorophenyl)ethyl)-N-((2-(trimethylsilyl)ethoxy)methyl)-1,2,3,4-tetrahydroisoquinoline-7-sulfonamide (0.1743 g, 0.288 mmol) and HCl (4 M in dioxane) (2 ml, 8.00 mmol) was heated to 70° C. for 1 h. LC/MS showed no starting material remaining. The reaction was concentrated in vacuo and the residue was purified by HPLC (30×100 mm WATERS SUNFIRE column; 5 micron; 35 mL/min.; 210 nM; 20% to 100% CH$_3$CN+0.05% TFA/water+0.05% TFA over 15 min.; the desired product elutes at 55% CH$_3$CN+ 0.05% TFA/water+0.05% TFA). The desired fractions were lyophilized overnight. $^1$H NMR (500 MHz, CD3CN) δ 8.69 (bs, 1H), 7.74 (dd, 1H), 7.68 (bs, 1H), 7.61 (s, 1H), 7.41-7.50 (m, 3H), 7.38 (d, 1H), 4.48 (m, 2H), 4.27 (m, 1H), 3.11-3.30 (bm, 4H), 1.78 (d, 3H), 1.23 (s, 9H). LC/MS (m/z): 474, 476 (M+H)$^+$. MGAT2 Human IC$_{50}$: 9 nM.

Example 2

Preparation of (R)—N-(5-(tert-butyl)isoxazol-3-yl)-2-(1-(2,3,5-trifluorophenyl)ethyl)-1,2,3,4-tetrahydroisoquinoline-7-sulfonamide

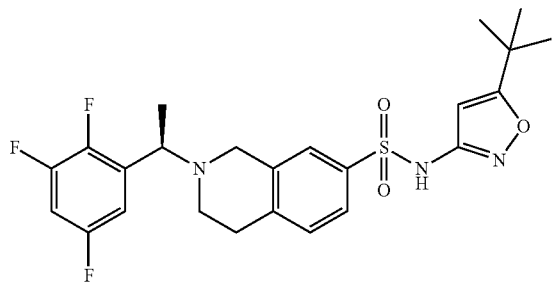 [SMILES: C[C@H](c1cc(F)cc(F)c1F)N1CCc2ccc(S(=O)(=O)Nc3cc(C(C)(C)C)on3)cc2C1]

Utilizing the procedure described in Example 1, Steps A-D, 1-(2,3,5-trifluorophenyl)ethanone (1.0 g) was elaborated to the final product, (R)—N-(5-(tert-butyl)isoxazol-3-yl)-2-(1-(2,3,5-trifluorophenyl)ethyl)-1,2,3,4-tetrahydroisoquinoline-7-sulfonamide.

Step A: (S)-1-(2,3,5-trifluorophenyl)ethanol.

Step B: (S)-1-(2,3,5-trifluorophenyl)ethyl methanesulfonate; $^1$H NMR (500 MHz, CDCl$_3$) δ (ppm): 6.91-7.00 (m, 2H), 5.99 (q, 1H), 2.99 (s, 3H), 1.71 (d, 3H).

Step C: (R)—N-(5-(tert-butyl)isoxazol-3-yl)-2-(1-(2,3,5-trifluorophenyl)ethyl)-N-((2-(trimethylsilyl)ethoxy)methyl)-1,2,3,4-tetrahydroisoquinoline-7-sulfonamide. $^1$H NMR (500 MHz, CDCl$_3$) δ (ppm): 7.81 (dd, 1H), 7.68 (s, 1H), 7.34 (d, 1H), 7.25 (m, 1H), 7.08 (m, 1H), 6.18 (s, 1H), 5.22 (s, 2H), 4.80 (q, 1H), 4.23-4.42 (m, 2H), 3.65 (t, 2H), 3.43 (m, 2H), 3.22 (m, 2H), 1.83 (d, 3H), 1.30 (s, 9H), 0.91 (t, 2H), 0.00 (s, 9H); MS m/z 624 (M+1)$^+$.

Step D: (R)—N-(5-(tert-butyl)isoxazol-3-yl)-2-(1-(2,3,5-trifluorophenyl)ethyl)-1,2,3,4-tetrahydroisoquinoline-7-sulfonamide. $^1$H NMR (500 MHz, CD3CN) δ (ppm): 8.68 (bs, 1H), 7.75 (dd, 1H), 7.69 (s, 1H), 7.39 (d, 1H), 7.36 (m, 1H), 7.23 (m, 1H), 6.06 (s, 1H), 7.79 (q, 1H), 4.20-4.40 (m, 2H), 3.18-3.45 (m, 4H), 1.77 (d, 3H), 1.24 (s, 9H); MS m/z 494 (M+H)$^+$. MGAT2 Human IC$_{50}$: 6 nM.

Example 3

Preparation of (R)—N-(5-(tert-butyl)isoxazol-3-yl)-2-(1-phenylethyl)-1,2,3,4-tetrahydroisoquinoline-7-sulfonamide

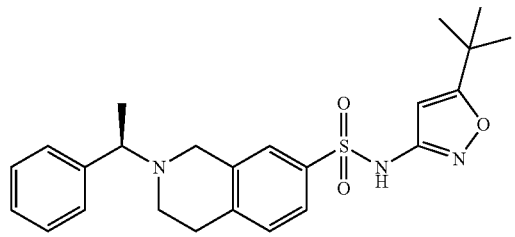 [SMILES: C[C@H](c1ccccc1)N1CCc2ccc(S(=O)(=O)Nc3cc(C(C)(C)C)on3)cc2C1]

Utilizing the procedure described in Example 1, Steps B-D, commercially available (S)-(−)-1-phenylethanol (1.0 g) was elaborated to the final product, (R)—N-(5-(tert-butyl)isoxazol-3-yl)-2-(1-phenylethyl)-1,2,3,4-tetrahydroisoquinoline-7-sulfonamide.

Step B: (S)-1-(phenyl)ethyl methanesulfonate; $^1$H NMR (500 MHz, CDCl$_3$) δ (ppm): 7.39-7.43 (m, 5H), 5.76 (q, 1H), 2.74 (s, 3H), 1.78 (d, 3H).

Step C: (R)—N-(5-(tert-butyl)isoxazol-3-yl)-2-(1-(phenyl)ethyl)-N-((2-(trimethylsilyl)ethoxy)methyl)-1,2,3,4-tetrahydroisoquinoline-7-sulfonamide. $^1$H NMR (500 MHz, CDCl$_3$) δ (ppm): 7.80 (d, 1H), 7.64 (bs, 1H), 7.40-7.50 (m, 5H), 7.32 (d, 1H), 6.16 (s, 1H), 5.22 (s, 2H), 4.45 (q, 1H), 4.20-4.40 (bm, 2H), 3.65 (t, 2H), 2.90-3.60 (bm, 4H), 1.84 (d, 3H), 1.32 (s, 9H), 0.93 (t, 2H), 0.00 (s, 9H); MS m/z 570 (M+1)$^+$.

Step D: (R)—N-(5-(tert-butyl)isoxazol-3-yl)-2-(1-(phenyl)ethyl)-1,2,3,4-tetrahydroisoquinoline-7-sulfonamide. $^1$H NMR (500 MHz, CD$_3$CN) δ (ppm): 7.60 (d, 1H), 7.53 (s, 1H), 7.34-7.40 (m, 5H), 7.27 (d, 1H), 6.07 (s, 1H), 3.50-3.84 (m, 3H), 2.59-2.95 (m, 4H), 1.95 (d, 3H), 1.23 (s, 9H); MS m/z 440 (M+H)$^+$. MGAT2 Human IC$_{50}$: 9 nM.

Example 4

Preparation of (R)—N-(5-(tert-butyl)isoxazol-3-yl)-2-(1-(2-(ethylthio)pyrimidin-5-yl)ethyl)-1,2,3,4-tetrahydroisoquinoline-7-sulfonamide

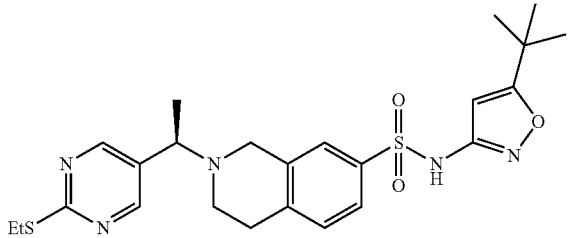

Step A: 1-(2-(ethylthio)pyrimidin-5-yl)ethanol

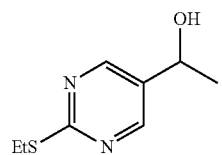

Methylmagnesium bromide (1.872 ml, 5.62 mmol) was added to a solution of 2-(ethylthio)-5-pyrimidine carboxyaldehyde (0.7872 g, 4.68 mmol) in THF (anhydrous) (8.0 ml), under nitrogen at ambient temperature. After 20 minutes, TLC (30% EtOAc/hexane) showed no starting material remaining. The reaction was partitioned between saturated NH$_4$Cl and EtOAc. The organic layer was collected, washed with brine, dried over MgSO$_4$, and concentrated in vacuo. The residue was purified by ISCO COMBIFLASH chromatography (24 g silica gel, 40 mL/min, 254 nM; the desired elutes at 51% EtOAc/hexane). $^1$H NMR (500 MHz, CDCl$_3$) δ (ppm): 8.56 (s, 2H), 4.90 (m, 1H), 3.18 (q, 2H), 1.57 (d, 3H), 1.40 (t, 3H). MGAT2 Human IC$_{50}$: 11 nM.

Utilizing the procedure described in Example 1, Steps B-D, 1-(2-(ethylthio)pyrimidin-5-yl)ethanol (0.786 g) was elaborated to the final product, (R)—N-(5-(tert-butyl)isoxazol-3-yl)-2-(1-(2-(ethylthio)pyrimidin-5-yl)ethyl)-1,2,3,4-tetrahydroisoquinoline-7-sulfonamide.

Step B: 1-(2-(ethylthio)pyrimidin-5-yl)ethyl methanesulfonate; $^1$H NMR (500 MHz, CDCl$_3$) δ (ppm): 8.59 (s, 2H), 5.74 (q, 1H), 3.19 (q, 2H), 2.98 (s, 3H), 1.78 (d, 3H), 1.40 (t, 3H).

Step C: N-(5-(tert-butyl)isoxazol-3-yl)-2-(1-(2-(ethylthio)pyrimidin-5-yl)ethyl)-N-((2-(trimethylsilyl)ethoxy)methyl)-1,2,3,4-tetrahydroisoquinoline-7-sulfonamide. $^1$H NMR (500 MHz, CDCl$_3$) δ (ppm): 8.69 (s, 2H), 7.81 (dd, 1H), 7.70 (s, 1H), 7.34 (d, 1H), 6.15 (s, 1H), 5.21 (s, 2H), 4.65 (q, 1H), 4.39 (m, 2H), 3.65 (t, 2H), 3.22-3.55 (m, 4H), 1.89 (d, 3H), 1.41 (t, 3H), 1.30 (s, 9H), 0.93 (t, 2H), 0.00 (s, 9H); MS m/z 632 (M$^+$+1).

Step D: racemic N-(5-(tert-butyl)isoxazol-3-yl)-2-(1-(2-(ethylthio)pyrimidin-5-yl)ethyl)-1,2,3,4-tetrahydroisoquinoline-7-sulfonamide. Chiral resolution using Chiral AD column (30×250 mm, 55% MeOH/CO2, 70 mL/min., 100 bar, 44 mg/mL in MeOH, 35° C., 254 nM) afforded the two enantiomers:

1) (S)—N-(5-(tert-butyl)isoxazol-3-yl)-2-(1-(2-(ethylthio)pyrimidin-5-yl)ethyl)-1,2,3,4-tetrahydroisoquinoline-7-sulfonamide: Faster moving isomer.

2) (R)—N-(5-(tert-butyl)isoxazol-3-yl)-2-(1-(2-(ethylthio)pyrimidin-5-yl)ethyl)-1,2,3,4-tetrahydroisoquinoline-7-sulfonamide: Slower moving isomer. $^1$H NMR (500 MHz, CD3CN) δ (ppm): 8.52 (s, 2H), 7.60 (dd, 1H), 7.55 (s, 1H), 7.25 (d, 1H), 6.07 (s, 1H), 3.63-3.79 (m, 3H), 3.10 (q, 2H), 2.70-2.91 (m, 4H), 1.43 (d, 3H), 1.33 (t, 3H); MS m/z 502 (M++1).

Example 5

Preparation (R)—N-(5-(tert-butyl)-4-methylisoxazol-3-yl)-2-(1-(6-(2,2,2-trifluoroethoxy)pyridin-3-yl)ethyl)-1,2,3,4-tetrahydroisoquinoline-7-sulfonamide

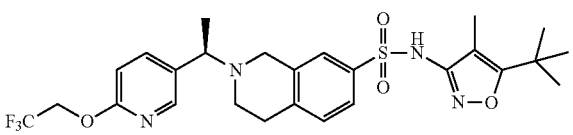

A solution of 1 M LiHMDS in THF (51.7 ml, 51.7 mmol) was added dropwise to a mixture of Intermediate 3 (7.5 g, 17.2 mmol) and 5-(tert-butyl)-4-methylisoxazol-3-amine (5.32 g, 34.5 mmol) in anhydrous THF (200 ml) that had been cooled to −78° C. and placed under a N$_2$ atmosphere. The acetone bath was removed and the solution aged at room temperature for 3 hrs. The reaction was quenched with saturated aqueous NH$_4$Cl solution and diluted with EtOAc. The two layers were separated and the aqueous phase extracted with EtOAc×2. The combined organic layers were dried over MgSO$_4$, filtered, and concentrated under reduced pressure. The resulting crude was purified by MPLC (KP-Sil 340 g SNAP column, BIOTAGE system) eluting with a gradient of 20-50% EtOAc/Hexane to afford the title compound. $^1$H NMR (500 MHz, CD$_3$Cl$_3$) δ 8.08 (s, 1H), 7.70 (m, 2H), 7.61 (s, 1H), 7.22 (d, 1H), 6.86 (d, 1H), 4.79 (q, 2H), 3.80 (m, 1H), 3.63 (m, 2H), 2.92 (t, 2H), 2.76 (m, 2H), 2.01 (s, 3H), 1.42 (d, 3H), 1.39 (s, 9H). LC/MS (m/z): 553 (M+H)$^+$. MGAT2 Human IC$_{50}$: 4.5 nM.

The Examples 6-8 in Table 1 were synthesized according to the methods described in Example 5 employing the appropriate reagents and solvents.

TABLE 1

| Example # | Chemical Structure | Observed Mass | MGAT2 Human IC$_{50}$ |
|---|---|---|---|
| 6 | 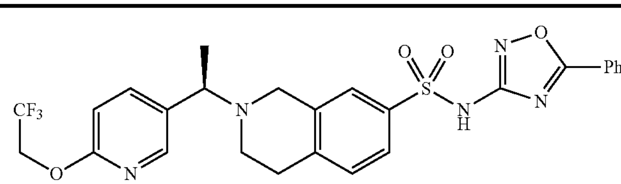 | 560 [M + H]$^+$ | 9.2 nM |

TABLE 1-continued

| Example # | Chemical Structure | Observed Mass | MGAT2 Human IC$_{50}$ |
|---|---|---|---|
| 7 | 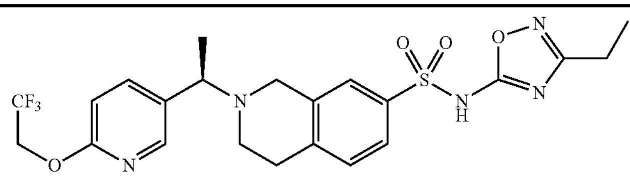 | 512 [M + H]$^+$ | 8.1 nM |
| 8 | 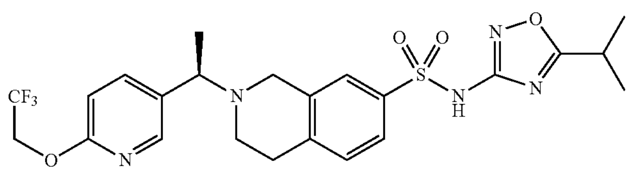 [SMILES: CC(C)c1nc(NS(=O)(=O)c2ccc3c(c2)CN([C@H](C)c2ccc(OCC(F)(F)F)nc2)CC3)no1] | 526 [M + H]$^+$ | 13 nM |

Example 9

Preparation of (R)—N-(5-(tert-butyl)isoxazol-3-yl)-2-(1-(6-(2,2,2-trifluoroethoxy)pyridin-3-yl)ethyl)-1,2,3,4-tetrahydroisoquinoline-7-sulfonamide

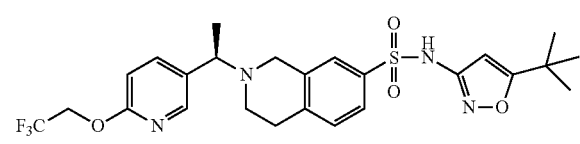

A solution of 1 M LiHMDS in THF (3.45 ml, 3.45 mmol) was added dropwise to a mixture of Intermediate 3 (500 mg, 1.15 mmol) and 5-(tert-butyl)isoxazol-3-amine (322 mg, 2.3 mmol) in anhydrous THF (20 ml) that had been cooled to −78° C. and placed under a N$_2$ atmosphere. The acetone bath was removed and the solution aged at room temperature for 3 hrs. The reaction was quenched with saturated aqueous NH$_4$Cl solution and diluted with EtOAc. The two layers were separated and the aqueous phase extracted with EtOAc×2. The combined organic layers were dried over MgSO$_4$, filtered, and concentrated under reduced pressure. The resulting crude was purified by MPLC (KP-Sil 10 g SNAP column, BIOTAGE system) eluting with a gradient of 15-40% EtOAc/Hexane to afford the title compound. $^1$H NMR (500 MHz, CD$_3$Cl$_3$) δ 8.08 (s, 1H), 7.70 (m, 1H), 7.61 (m, 1H), 7.55 (d, 1H), 7.22 (d, 1H), 6.86 (d, 1H), 6.20 (s, 1H), 4.80 (q, 2H), 3.80 (m, 1H), 3.63 (m, 2H), 2.92 (t, 2H), 2.76 (m, 2H), 1.42 (d, 3H), 1.35 (s, 9H). LC/MS (m/z): 539 (M+H)$^+$. MGAT2 Human IC$_{50}$: 11 nM.

Example 10

Preparation of (R)—N-(4-bromo-5-(tert-butyl)isoxazol-3-yl)-2-(1-(2-(2,2,2-trifluoroethoxy)pyrimidin-5-yl)ethyl)-1,2,3,4-tetrahydroisoquinoline-7-sulfonamide

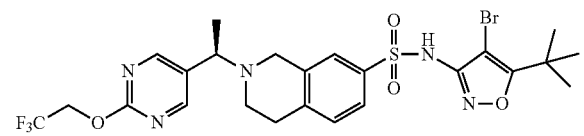

Step A: 1-(7-(benzylthio)-3,4-dihydroisoquinolin-2(1H)-yl)-2,2,2-trifluoroethanone

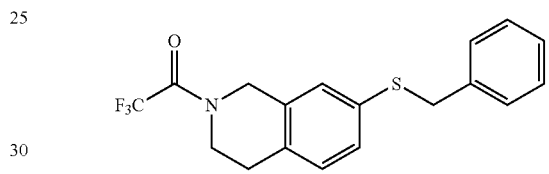

Benzyl mercaptan (5.63 ml, 47.6 mmol) was introduced to a solution of 1-(7-bromo-3,4-dihydroisoquinolin-2(1H)-yl)-2,2,2-trifluoroethanone (14.5 g, 47.2 mmol), DIEA (16.6, 95 mmol), Pd$_2$(dba)$_3$ (0.86 g, 0.94 mmol), and Xantphos (1.64 g, 2.83 mmol) in anhydrous 1,4-dioxane (200 ml) that had been degassed with N$_2$ for 10 min. The flask was fitted with a reflux condensor, evacuated and backfilled with N$_2$×2, and the mixture refluxed at 102° C. for 2 hrs. The reaction mixture was cooled to room temperature and filtered through a fritted funnel. The filtrate was concentrated under reduced pressure then taken up in EtOAc, washed with water, dried over MgSO$_4$, filtered, and concentrated under reduced pressure. The obtained crude material was purified by flash column (340 g, SNAP, 5~10% EtOAc in hexane) to afford the title compound. LC/MS (m/z): 352 (M+H)$^+$.

Step B: 2-(2,2,2-trifluoroacetyl)-1,2,3,4-tetrahydroisoquinoline-7-sulfonyl Chloride

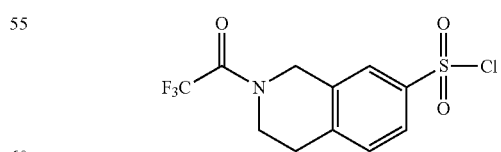

Sulfuryl chloride (2 ml, 24.6 mmol) was added dropwise to a solution of 1-(7-(benzylthio)-3,4-dihydroisoquinolin-2(1H)-yl)-2,2,2-trifluoroethanone (2.27 g, 6.46 mmol), water (0.5 ml, 27.8 mmol), and acetic acid (1.5 ml, 26.2 mmol) in DCM (30 ml) that had been cooled to 0° C. in an ice bath and degassed with N$_2$ for 10 min. The ice bath was removed and the mixture stirred at room temperature for 4 hrs. The solution was quenched with saturated aqueous NaHCO$_3$ solution and the layers cut. The aqueous phase was extracted with DCM×3 and the combined organic layers dried over MgSO$_4$, filtered, then concentrated under reduced pressure. The obtained crude material was purified by flash column (50 g, SNAP, 10~30% EtOAc in hexane) to afford the title compound. LC/MS (m/z): 327 (M+H)$^+$.

Step C: N-(4-bromo-5-(tert-butyl)isoxazol-3-yl)-2-(2,2,2-trifluoroacetyl)-1,2,3,4-tetrahydroisoquinoline-7-sulfonamide

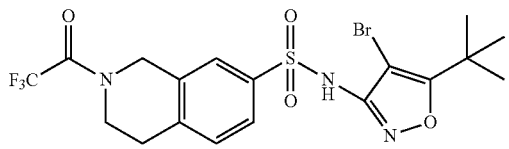 [SMILES: CC(C)(C)c1onc(NS(=O)(=O)c2ccc3c(c2)CN(C(=O)C(F)(F)F)CC3)c1Br]

A solution of 1 M LiHMDS in THF (9.11 ml, 9.11 mmol) was added dropwise to a mixture of 2-(2,2,2-trifluoroacetyl)-1,2,3,4-tetrahydroisoquinoline-7-sulfonyl chloride (1.865 g, 5.69 mmol) and 4-bromo-5-(tert-butyl)isoxazol-3-amine (1.37 g, 6.26 mmol) in anhydrous THF (20 ml) that had been cooled to −78° C. and placed under a N$_2$ atmosphere. The acetone bath was removed and the solution aged at room temperature for 3 hrs. The reaction was quenched with saturated aqueous NH$_4$Cl solution and diluted with EtOAc. The two layers were separated and the aqueous phase extracted with EtOAc×2. The combined organic layers were dried over MgSO$_4$, filtered, and concentrated under reduced pressure. The resulting crude was purified by MPLC (KP-Sil 50 g SNAP column, BIOTAGE system) eluting with a gradient of 10-40% EtOAc/Hexane to afford the title compound. LC/MS (m/z): 511 (M+H)$^+$.

Step D: N-(4-bromo-5-(tert-butyl)isoxazol-3-yl)-2-(2,2,2-trifluoroacetyl)-N-((2-(trimethylsilyl)ethoxy)methyl)-1,2,3,4-tetrahydroisoquinoline-7-sulfonamide

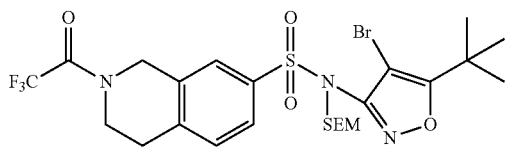 [SMILES: CC(C)(C)c1onc(N(COCC[Si](C)(C)C)S(=O)(=O)c2ccc3c(c2)CN(C(=O)C(F)(F)F)CC3)c1Br]

NaH (0.23 g, 60% dispersion, 5.7 mmol) was added to a solution of N-(4-bromo-5-(tert-butyl)isoxazol-3-yl)-2-(2,2,2-trifluoroacetyl)-1,2,3,4-tetrahydroisoquinoline-7-sulfonamide (1.94 g, 3.8 mmol) in anhydrous DMF (20 mL) at 0° C. under N$_2$. After gas evolution ceased, SEMCl (0.8 mL, 4.56 mmol) was added dropwise. The reaction was allowed to warm to room temperature and stirred overnight. The mixture was partitioned between EtOAc and ice/sat. NH$_4$Cl. The organic phase was washed with brine, dried over MgSO$_4$, and evaporated. The crude material was purified by flash column (25 g SNAP, 5~20% EtOAc in hexane) to afford the title compound.
LC/MS (m/z): 640 (M+H)$^+$.

Step E: N-(4-bromo-5-(tert-butyl)isoxazol-3-yl)-N-((2-(trimethylsilyl)ethoxy)methyl)-1,2,3,4-tetrahydroisoquinoline-7-sulfonamide

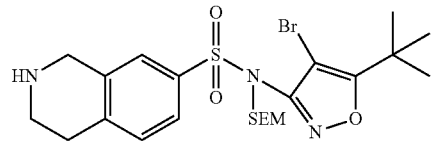 [SMILES: CC(C)(C)c1onc(N(COCC[Si](C)(C)C)S(=O)(=O)c2ccc3c(c2)CNCC3)c1Br]

Concentrated NH$_4$OH (2.5 mL) was added to a solution of N-(4-bromo-5-(tert-butyl)isoxazol-3-yl)-2-(2,2,2-trifluoroacetyl)-N-((2-(trimethylsilyl)ethoxy)methyl)-1,2,3,4-tetrahydroisoquinoline-7-sulfonamide (2.3 g, 3.59 mmol) in MeOH (20 mL) at room temperature. The reaction was stirred at room temperature overnight. The mixture was evaporated under reduced pressure and the resulting residue was dissolved in EtOAc, washed with water, dried over MgSO$_4$, and evaporated to afford the title compound. LC/MS (m/z): 544 (M+H)$^+$.

Step F: (S)-1-(2-chloropyrimidin-5-yl)ethanol

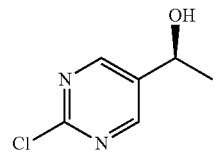

Ketoreductase (KRED) P3C3 (160 mg) (KRED Plate available from CODEXIS) and NADP (65 mg) was added to a 100 mL vial containing phosphate buffer (pH 7.0, 100 mM, 15 mL). The mixture was stirred until solids were dissolved. The solution was heated to 30° C. To this enzyme/buffer solution, a solution of 1-(2-chloropyrimidin-5-yl)ethanone (0.658 g, 4.2 mmol) in 2-propanol (7 mL) was added dropwise. The reaction was stirred at 30° C. overnight. The mixture was diluted with water, extracted with EtOAc. The organic phase was washed with brine and water, dried over MgSO$_4$, and evaporated to afford the title compound. LC/MS (m/z): 159 (M+H)$^+$.

Step G: (S)-1-(2-chloropyrimidin-5-yl)ethyl Methanesulfonate

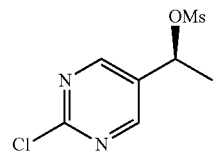

(S)-1-(2-chloropyrimidin-5-yl)ethanol (450 mg, 2.84 mmol) was dissolved in DCM (15 mL) and triethylamine (0.79 mL, 5.78 mmol) was added. The mixture was stirred at 0° C. for 5 min then methanesulfonyl chloride (0.287, 3.69 mmol) was added and stirred at 0° C. for 1 h. The mixture was diluted with DCM, washed with water, dried over MgSO$_4$, and evaporated to afford the title compound. LC/MS (m/z): 237 (M+H)$^+$.

Step H: (R)—N-(4-bromo-5-(tert-butyl)isoxazol-3-yl)-2-(1-(2-chloropyrimidin-5-yl)ethyl)-N-((2-(trimethylsilyl)ethoxy)methyl)-1,2,3,4-tetrahydroisoquinoline-7-sulfonamide

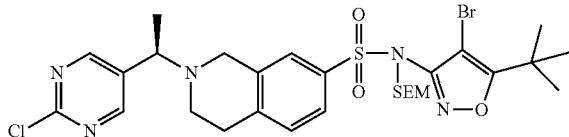 [SMILES: C[C@H](c1cnc(Cl)nc1)N1CCc2ccc(S(=O)(=O)N(COCC[Si](C)(C)C)c3noc(C(C)(C)C)c3Br)cc2C1]

(S)-1-(2-chloropyrimidin-5-yl)ethyl methanesulfonate (94 mg, 0.4 mmol) and N-(4-bromo-5-(tert-butyl)isoxazol-3-yl)-N-((2-(trimethylsilyl)ethoxy)methyl)-1,2,3,4-tetrahydroisoquinoline-7-sulfonamide (Step E, 180 mg, 0.33 mmol) were dissolved in DMF (4 mL) and LiOH (32 mg, 1.33 mmol) was added. The mixture was heated at 50° C. overnight. The reaction was quenched with saturated NH$_4$Cl and extracted with EtOAc. The EtOAc phase was washed with water, dried over MgSO$_4$, and evaporated. The crude oil was purified by flash column (10 g, SNAP, 15~40% EtOAc in hexane) to afford the title compound. LC/MS (m/z): 684 (M+H)$^+$.

Step I: (R)—N-(4-bromo-5-(tert-butyl)isoxazol-3-yl)-2-(1-(2-(2,2,2-trifluoroethoxy) pyrimidin-5-yl)ethyl)-N-((2-(trimethylsilyl)ethoxy)methyl)-1,2,3,4-tetrahydroisoquinoline-7-sulfonamide

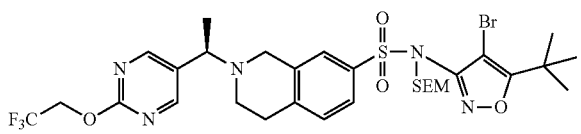 [SMILES: C[C@H](c1cnc(OCC(F)(F)F)nc1)N1CCc2ccc(S(=O)(=O)N(COCC[Si](C)(C)C)c3noc(C(C)(C)C)c3Br)cc2C1]

(R)—N-(4-bromo-5-(tert-butyl)isoxazol-3-yl)-2-(1-(2-chloropyrimidin-5-yl)ethyl)-N-((2-(trimethylsilyl)ethoxy)methyl)-1,2,3,4-tetrahydroisoquinoline-7-sulfonamide (80 mg, 0.117 mmol) was dissolved in CF$_3$CH$_2$OH (4 mL) and DMF (2 mL), and NaH (60%, 7 mg, 0.175 mmol) was added. The mixture was microwaved at 100° C. for 1 h. The reaction was cooled to room temperature, quenched with sat. NH$_4$Cl, extracted with EtOAc, dried and evaporated. The crude material was purified by preparative thin layer chromatography "PTLC" (40% EtOAc in hexane) to afford the title compound. LC/MS (m/z): 748 (M+H)$^+$.

Step J: (R)—N-(4-bromo-5-(tert-butyl)isoxazol-3-yl)-2-(1-(2-(2,2,2-trifluoroethoxy)pyrimidin-5-yl)ethyl)-1,2,3,4-tetrahydroisoquinoline-7-sulfonamide

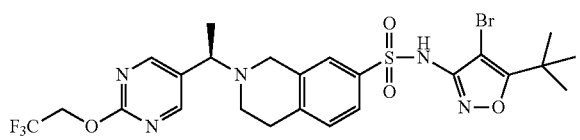

A solution of (R)—N-(4-bromo-5-(tert-butyl)isoxazol-3-yl)-2-(1-(2-(2,2,2-trifluoroethoxy) pyrimidin-5-yl)ethyl)-N-((2-(trimethylsilyl)ethoxy)methyl)-1,2,3,4-tetrahydroisoquinoline-7-sulfonamide (55 mg, 0.073 mmol) and 4 M HCl in dioxane (4 mL, 16 mmol) was stirred at 50° C. for 2 h. The mixture was partitioned between EtOAc and sat. NaHCO$_3$. The organic phase was separated, dried over MgSO$_4$, and evaporated. The crude material was purified by PTLC (50% EtOAc in hexane) to afford the title compound. $^1$H NMR (500 MHz, CD$_3$Cl$_3$) δ 8.70 (s, 2H), 7.60~7.70 (m, 2H), 7.22 (d, 1H), 4.95 (q, 2H), 3.90~4.0 (m, 2H), 3.60~3.80 (m, 3H), 2.80~2.95 (m, 4H), 1.59 (d, 3H), 1.39 (s, 9H). LC/MS (m/z): 618 (M+H)$^+$. MGAT2 Human IC$_{50}$: 17 nM.

Example 11

Preparation of (R)—N-(5-(tert-butyl)-4-(3-fluorophenyl)isoxazol-3-yl)-2-(1-(2-(2,2,2-trifluoroethoxy)pyrimidin-5-yl)ethyl)-1,2,3,4-tetrahydroisoquinoline-7-sulfonamide

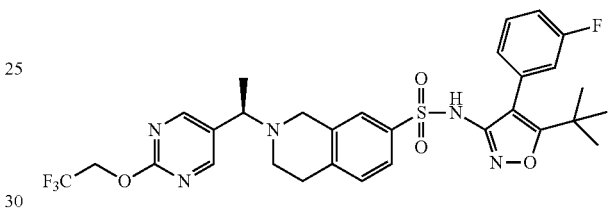

(R)—N-(4-bromo-5-(tert-butyl)isoxazol-3-yl)-2-(1-(2-(2,2,2-trifluoroethoxy)pyrimidin-5-yl)ethyl)-1,2,3,4-tetrahydroisoquinoline-7-sulfonamide (Example 10, 17 mg, 0.027 mmol), (3-fluorophenyl)boronic acid (7.7 mg, 0.055 mmol), 1,1'-bis(di-tert-butylphosphino)ferrocene palladium dichloride (1.8 mg, 2.75 µmol) and K$_3$PO$_4$ (50% wt solution, 0.3 mL) were dissolved in DMF in 2 mL-microwave vial. The mixture was degassed with N$_2$ 3 times, and microwaved at 90° C. for 1 h. The mixture was purified by HPLC (SUNFIRE prep. column, 80:20 CH$_3$CN:Water 0.1% TFA) and PTLC (50% EtOAc in hexane) to afford the target compound. $^1$H NMR (500 MHz, CD$_3$Cl$_3$) δ 8.70 (s, 2H), 7.60 (m, 1H), 7.58 (s, 1H), 7.40 (m, 1H), 7.22 (d, 1H), 7.15 (m, 1H), 6.90 (d, 1H), 6.78 (d, 1H), 4.95 (q, 2H), 3.80~3.90 (m, 2H), 3.71 (m, 1H), 2.80~2.95 (m, 4H), 1.59 (d, 3H), 1.19 (s, 9H). LC/MS (m/z): 634 (M+H)$^+$. MGAT2 Human IC$_{50}$: 20 nM.

Example 12

Preparation of (R)—N-(5-(tert-butyl)isoxazol-3-yl)-2-(1-(2-(2,2,2-trifluoroethoxy)pyrimidin-5-yl)ethyl)-1,2,3,4-tetrahydroisoquinoline-7-sulfonamide

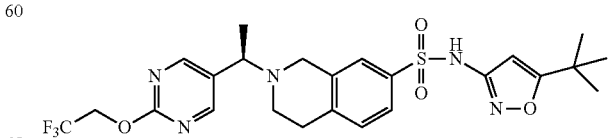

Step A: (R)-7-(benzylthio)-2-(1-(2-chloropyrimidin-5-yl)ethyl)-1,2,3,4-tetrahydroisoquinoline

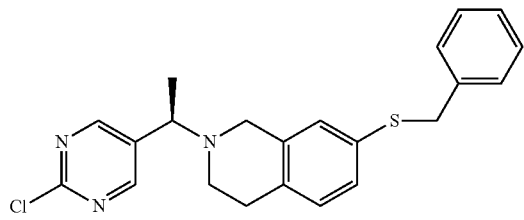 [SMILES: C[C@H](c1cnc(Cl)nc1)N1CCc2ccc(SCc3ccccc3)cc2C1]

(S)-1-(2-chloropyrimidin-5-yl)ethyl methanesulfonate (from Step G of Example 10, 1.3 g, 5.49 mmol) and 7-(benzylthio)-1,2,3,4-tetrahydroisoquinoline (Int. 2, Step A, 1.68 g, 6.59 mmol) were dissolved in DMF (30 mL), and $K_2CO_3$ (1.90 g, 13.7 mmol) was added. The mixture was stirred at room temperature overnight. The reaction was quenched with sat. $NH_4Cl$, and extracted with EtOAc. The organic phase was dried over $MgSO_4$, and evaporated. The crude material was purified by flash column (25 g SNAP, 5~20% EtOAc in hexane) to afford the title compound. LC/MS (m/z): 396 (M+H)$^+$.

Step B: (R)-7-(benzylthio)-2-(1-(2-(2,2,2-trifluoroethoxy)pyrimidin-5-yl)ethyl)-1,2,3,4-tetrahydroisoquinoline

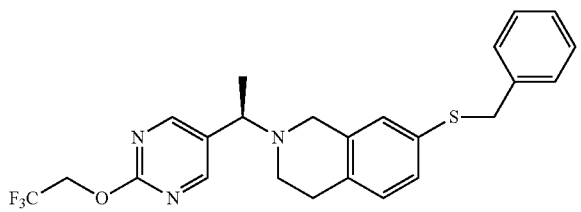 [SMILES: C[C@H](c1cnc(OCC(F)(F)F)nc1)N1CCc2ccc(SCc3ccccc3)cc2C1]

(R)-7-(benzylthio)-2-(1-(2-chloropyrimidin-5-yl)ethyl)-1,2,3,4-tetrahydroisoquinoline (0.94 g, 2.37 mmol) was dissolved in DMF (10 mL) and NaH (60%, 0.19 g, 4.75 mmol) and $CF_3CH_2OH$ (1 mL) were added at 0° C. The mixture was heated at 80° C. for 3 h. The mixture was cooled to room temperature, quenched with saturated $NH_4Cl$, and extracted with EtOAc. The organic phase was dried over $MgSO_4$, and evaporated under reduced pressure. The crude material was purified by flash column (10 g SNAP, 10~30% EtOAc in hexane) to afford the title compound. LC/MS (m/z): 460 (M+H)$^+$.

Step C: (R)-2-(1-(2-(2,2,2-trifluoroethoxy)pyrimidin-5-yl)ethyl)-1,2,3,4-tetrahydroisoquinoline-7-sulfonyl Chloride

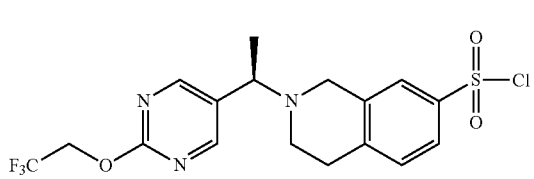 [SMILES: C[C@H](c1cnc(OCC(F)(F)F)nc1)N1CCc2ccc(S(=O)(=O)Cl)cc2C1]

Sulfuryl chloride (0.64 ml, 7.92 mmol) was added dropwise to a solution of (R)-7-(benzylthio)-2-(1-(2-(2,2,2-trifluoroethoxy)pyrimidin-5-yl)ethyl)-1,2,3,4-tetrahydroisoquinoline (0.91 g, 1.98 mmol), water (0.14 ml, 7.92 mmol), and acetic acid (0.45 ml, 7.92 mmol) in DCM (15 ml) that had been cooled to 0° C. in an ice bath and degassed with $N_2$ for 10 min. The ice bath was removed and the mixture stirred at room temperature for 4 hrs. The solution was quenched with saturated aqueous $NaHCO_3$ solution and the layers cut. The aqueous phase was extracted with DCM×3 and the combined organic layers dried over $MgSO_4$, filtered, then concentrated under reduced pressure to afford the title compound. LC/MS (m/z): 436 (M+H)$^+$.

Step D: (R)—N-(5-(tert-butyl)isoxazol-3-yl)-2-(1-(2-(2,2,2-trifluoroethoxy)pyrimidin-5-yl)ethyl)-1,2,3,4-tetrahydroisoquinoline-7-sulfonamide

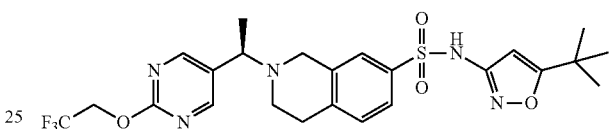

A solution of 1 M LiHMDS in THF (0.55 ml, 0.55 mmol) was added dropwise to a mixture of (R)-2-(1-(2-(2,2,2-trifluoroethoxy)pyrimidin-5-yl)ethyl)-1,2,3,4-tetrahydroisoquinoline-7-sulfonyl chloride (80 mg, 0.184 mmol) and 5-(tert-butyl)isoxazol-3-amine (51.5 mg, 0.367 mmol) in anhydrous THF (5 ml) that had been cooled to −78° C. and placed under a $N_2$ atmosphere. The acetone bath was removed and the solution aged at room temperature for 3 hrs. The reaction was quenched with saturated aqueous $NH_4Cl$ solution and diluted with EtOAc. The two layers were separated and the aqueous phase extracted with EtOAc×2. The combined organic layers were dried over $MgSO_4$, filtered, and concentrated under reduced pressure. The resulting crude was purified by MPLC (KP-Sil 10 g SNAP column, BIOTAGE system) eluting with a gradient of 20-50% EtOAc/Hexane to afford the target compound. $^1H$ NMR (500 MHz, $CD_3Cl_3$) δ 8.60 (s, 2H), 7.62 (d, 1H), 7.58 (s, 1H), 7.22 (m, 1H), 6.20 (s, 1H), 4.81 (q, 2H), 3.82 (m, 1H), 3.78 (m, 1H), 3.62 (m, 1H), 2.92 (m, 2H), 2.70~2.80 (m, 2H), 1.50 (s, 3H), 1.35 (s, 9H). LC/MS (m/z): 540 (M+H)$^+$. MGAT2 Human $IC_{50}$: 14 nM.

Example 13

Preparation of (R)—N-(5-(tert-butyl)-4-chloroisoxazol-3-yl)-2-(1-(6-(2,2,2-trifluoroethoxy)pyridin-3-yl)ethyl)-1,2,3,4-tetrahydroisoquinoline-7-sulfonamide

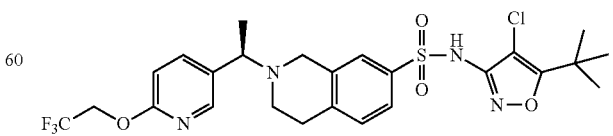

A solution of 1 M LiHMDS in THF (1.38 ml, 1.38 mmol) was added dropwise to a mixture of Intermediate 3 (200 mg, 0.46 mmol) and 5-(tert-butyl)-4-chloroisoxazol-3-amine (161 mg, 0.92 mmol) in anhydrous THF (10 ml) that had been cooled to −78° C. and placed under a N₂ atmosphere. The acetone bath was removed and the solution aged at room temperature for 3 hrs. The reaction was quenched with saturated aqueous NH₄Cl solution and diluted with EtOAc. The two layers were separated and the aqueous phase extracted with EtOAc×2. The combined organic layers were dried over MgSO₄, filtered, and concentrated under reduced pressure. The resulting crude was purified by MPLC (KP-Sil 10 g SNAP column, BIOTAGE system) eluting with a gradient of 20-50% EtOAc/Hexane to afford the target compound. ¹H NMR (500 MHz, CD₃Cl₃) δ 8.08 (s, 1H), 7.90 (m, 1H), 7.75 (m, 1H), 7.70 (d, 1H), 7.22 (d, 1H), 6.90 (d, 1H), 4.80 (q, 2H), 3.70 (m, 1H), 3.62 (m, 2H), 2.95 (m, 2H), 2.76 (m, 1H), 2.65 (m, 1H), 1.42 (d, 3H), 1.35 (s, 9H). LC/MS (m/z): 573 (M+H)⁺. MGAT2 Human IC₅₀: 16 nM.

Example 14

Preparation of (R)—N-(5-(tert-butyl)-4-methylisoxazol-3-yl)-2-(1-(5-(2,2,2-trifluoroethoxy)pyrazin-2-yl)ethyl)-1,2,3,4-tetrahydroisoquinoline-7-sulfonamide

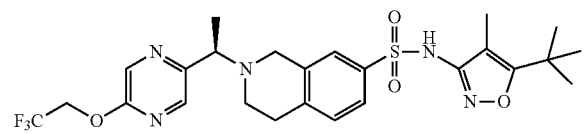

A solution of 1 M LiHMDS in THF (1.03 ml, 1.03 mmol) was added dropwise to a mixture of Intermediate 4 (150 mg, 0.344 mmol) and 5-(tert-butyl)-4-methylisoxazol-3-amine (106 mg, 0.7 mmol) in anhydrous THF (5 ml) that had been cooled to −78° C. and placed under a N₂ atmosphere. The acetone bath was removed and the solution aged at room temperature overnight. The reaction was quenched with saturated aqueous NH₄Cl solution and diluted with EtOAc. The two layers were separated and the aqueous phase extracted with EtOAc×2. The combined organic layers were dried over MgSO₄, filtered, and concentrated under reduced pressure. The resulting crude was purified by MPLC (KP-Sil 10 g SNAP column, BIOTAGE system) eluting with a gradient of 15-40% EtOAc/Hexane to afford the target compound. ¹H NMR (500 MHz, CD₃Cl₃) δ 8.38 (s, 1H), 8.20 (s, 1H), 7.70 (d, 1H), 7.60 (s, 1H), 7.22 (d, 1H), 4.80 (q, 2H), 3.85 (m, 2H), 3.70 (m, 1H), 2.95 (m, 2H), 2.80 (m, 2H), 2.00 (s, 3H), 1.55 (d, 3H), 1.38 (s, 9H). LC/MS (m/z): 554 (M+H)⁺. MGAT2 Human IC₅₀: 3.1 nM.

Example 15

Preparation of N-(5-(tert-butyl)-4-methylisoxazol-3-yl)-2-((6-(2,2,2-trifluoroethoxy)pyridin-3-yl)methyl)-1,2,3,4-tetrahydroisoquinoline-7-sulfonamide

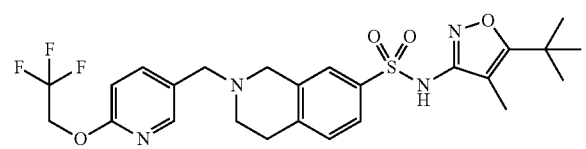 [SMILES: Cc1c(NS(=O)(=O)c2ccc3c(c2)CN(Cc2ccc(OCC(F)(F)F)nc2)CC3)noc1C(C)(C)C]

Step A: N-(4-bromo-5-(tert-butyl)isoxazol-3-yl)-2-((6-(2,2,2-trifluoroethoxy)pyridin-3-yl)methyl)-1,2,3,4-tetrahydroisoquinoline-7-sulfonamide

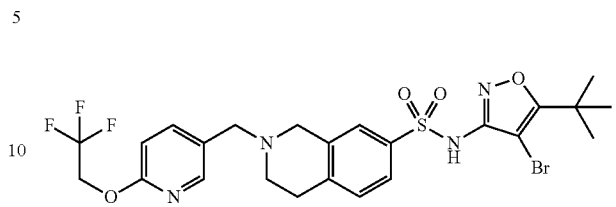

A solution of 1 M LiHMDS in THF (1.42 ml, 1.42 mmol) was added dropwise to a mixture of Intermediate 2 (213 mg, 0.507 mmol) and 4-bromo-5-(tert-butyl)isoxazol-3-amine (232 mg, 1.07 mmol) in anhydrous THF (1.69 ml) that had been cooled to −78° C. and placed under a N₂ atmosphere. The acetone bath was removed and the solution aged at room temperature for 3 hrs. The reaction was quenched with saturated aqueous NH₄Cl solution and diluted with EtOAc. The two layers were separated and the aqueous phase extracted with EtOAc×2. The combined organic layers were dried over MgSO₄, filtered, and concentrated under reduced pressure. The resulting crude was purified by MPLC (KP-Sil 10 g SNAP column, BIOTAGE system) eluting with a gradient of 4-9% MeOH/DCM over 11 CV to afford the target compound. LC/MS (m/z): 603 (M+H)⁺.

Step B: N-(5-(tert-butyl)-4-methylisoxazol-3-yl)-2-((6-(2,2,2-trifluoroethoxy)pyridin-3-yl)methyl)-1,2,3,4-tetrahydroisoquinoline-7-sulfonamide

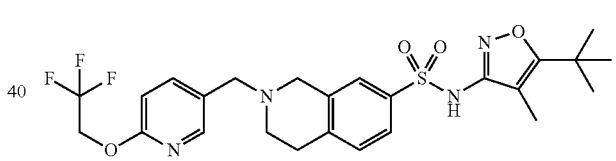

50% wt. aqueous K₃PO₄ solution (250 uL, 0.88 mmol) was added to a mixture of N-(4-bromo-5-(tert-butyl)isoxazol-3-yl)-2-((6-(2,2,2-trifluoroethoxy)pyridin-3-yl)methyl)-1,2,3,4-tetrahydroisoquinoline-7-sulfonamide (80 mg, 0.132 mmol), trimethylboroxine (37 uL, 0.264 mmol), and 1,1'-bis(di-tert-butylphosphino)ferrocene palladium dichloride (13 mg, 0.02 mmol) in DMF (2 ml). The reaction mixture was degassed with N₂ for 10 min then heated thermally at 90° C. for 40 min. The mixture was cooled and filtered through a syringe-driven filter unit, washing with ACN. The resulting solution was purified by reverse phase HPLC [SUNFIRE 18C, OBD column, 90-5% (0.1% TFA/H₂O)/(0.1% TFA/ACN) over 15 min]. The desired fractions were combined, neutralized with saturated aqueous NaHCO₃ solution, and extracted with EtOAc×3. The combined organic layers were dried over MgSO₄, filtered, and concentrated under reduced pressure to afford the title compound. ¹H NMR (500 MHz, CD₃Cl₃) δ 8.08 (s, 1H), 7.70 (d, 2H), 7.61 (s, 1H), 7.22 (d, 1H), 6.86 (d, 1H), 4.79 (q, 2H), 3.64 (s, 2H), 3.63 (s, 2H), 2.92 (t, 2H), 2.76 (t, 2H), 1.99 (s, 3H), 1.33 (s, 9H). LC/MS (m/z): 539 (M+H)⁺. MGAT2 Human IC₅₀: 11 nM.

Example 16

Preparation of N-(5-(tert-butyl)-4-fluoroisoxazol-3-yl)-2-((6-(2,2,2-trifluoroethoxy)pyridin-3-yl)methyl)-1,2,3,4-tetrahydroisoquinoline-7-sulfonamide

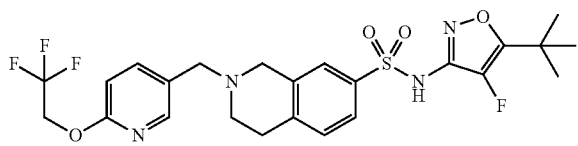 [SMILES: CC(C)(C)c1onc(NS(=O)(=O)c2ccc3c(c2)CN(Cc2ccc(OCC(F)(F)F)nc2)CC3)c1F]

Step A: 5-(tert-butyl)-4-fluoroisoxazol-3-amine

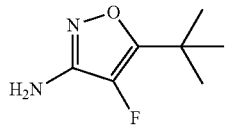

A solution of SELECTFLUOR (3.72 g, 10.5 mmol) and 5-(tert-butyl)isoxazol-3-amine (1.4 g, 10 mmol) in anhydrous ACN was heated at 120° C. in the microwave for 1 hr. The reaction mixture was cooled to room temperature, quenched by the addition of saturated aqueous NaHCO$_3$ solution, and diluted with EtOAc. The layers were separated and the aqueous phase extracted with EtOAc×2. The combined organic layers were dried over MgSO$_4$, filtered, and concentrated under reduced pressure. The residue was purified by MPLC (KP-Sil 100 g SNAP column, BIOTAGE system) eluting with a range of 0-10% EtOAc/Hex over 12 CV to afford the desired compound. LC/MS (m/z): 159 (M+H)$^+$.

Step B: N-(5-(tert-butyl)-4-fluoroisoxazol-3-yl)-2-((6-(2,2,2-trifluoroethoxy)pyridin-3-yl)methyl)-1,2,3,4-tetrahydroisoquinoline-7-sulfonamide

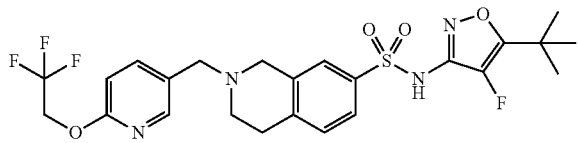 [SMILES: CC(C)(C)c1onc(NS(=O)(=O)c2ccc3c(c2)CN(Cc2ccc(OCC(F)(F)F)nc2)CC3)c1F]

A solution of 1 M LiHMDS in THF (1.33 ml, 1.33 mmol) was added dropwise to a solution of Intermediate 2 and 5-(tert-butyl)-4-fluoroisoxazol-3-amine (158 mg, 0.998 mmol) in anhydrous THF (1.58 ml) that had been cooled to −78° C. and placed under a N$_2$ atmosphere. The acetone bath was removed and the solution aged at room temperature for 3 hrs. The reaction was quenched with saturated aqueous NH$_4$Cl solution and diluted with EtOAc. The two layers were separated and the aqueous phase extracted with EtOAc×2. The combined organic layers were dried over MgSO$_4$, filtered, and concentrated under reduced pressure. The resulting crude was purified by reverse phase HPLC [SUNFIRE 18C, OBD column, 90-5% (0.1% TFA/H$_2$O)/(0.1% TFA/ACN) over 15 min]. The desired fractions were combined, neutralized with saturated aqueous NaHCO$_3$ solution, and extracted with EtOAc×3. The combined organic layers were dried over MgSO$_4$, filtered, and concentrated under reduced pressure to afford the title compound. $^1$H NMR (500 MHz, CD$_3$Cl$_3$) δ 8.11 (s, 1H), 7.78 (d, 1H), 7.74 (d, 1H), 7.67 (s, 1H), 7.23 (d, 1H), 6.88 (d, 1H), 4.79 (q, 2H), 3.76 (s, 2H), 3.72 (s, 2H), 2.97 (t, 2H), 2.81 (t, 2H), 1.33 (s, 9H). LC/MS (m/z): 543 (M+H)$^+$. MGAT2 Human IC$_{50}$: 16 nM.

Example 17

Preparation of (R)—N-(5-methyl-4-(1-methyl-1H-pyrazol-4-yl)isoxazol-3-yl)-2-(1-(6-(2,2,2-trifluoroethoxy)pyridin-3-yl)ethyl)-1,2,3,4-tetrahydroisoquinoline-7-sulfonamide

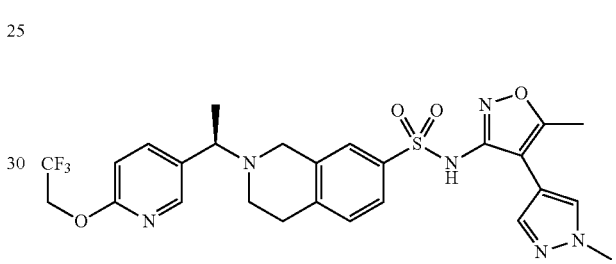

Step A: (R)—N-(4-bromo-5-methylisoxazol-3-yl)-2-(1-(6-(2,2,2-trifluoroethoxy)pyridin-3-yl)ethyl)-1,2,3,4-tetrahydroisoquinoline-7-sulfonamide

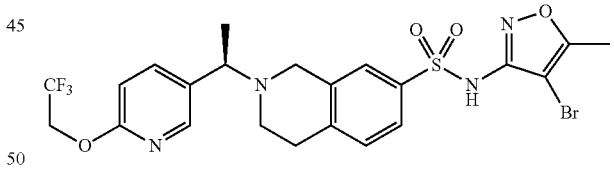

A solution of 1 M LiHMDS in THF (1.42 ml, 1.42 mmol) was added dropwise to a mixture of Intermediate 3 (600 mg, 1.10 mmol) and 4-bromo-5-methylisoxazol-3-amine (410 mg, 2.32 mmol) in anhydrous THF (3.7 ml) that had been cooled to −78° C. and placed under a N$_2$ atmosphere. The acetone bath was removed and the solution aged at room temperature for 3 hrs. The reaction was quenched with saturated aqueous NH$_4$Cl solution and diluted with EtOAc. The two layers were separated and the aqueous phase extracted with EtOAc×2. The combined organic layers were dried over MgSO$_4$, filtered, and concentrated under reduced pressure. The resulting crude was purified by MPLC (KP-Sil 25 g SNAP column, BIOTAGE system) eluting with a gradient of 1-9% MeOH/DCM over 12 CV to afford the target compound. LC/MS (m/z): 575 (M+H)$^+$.

Step B: (R)—N-(5-methyl-4-(1-methyl-1H-pyrazol-4-yl)isoxazol-3-yl)-2-(1-(6-(2,2,2-trifluoroethoxy)pyridin-3-yl)ethyl)-1,2,3,4-tetrahydroisoquinoline-7-sulfonamide

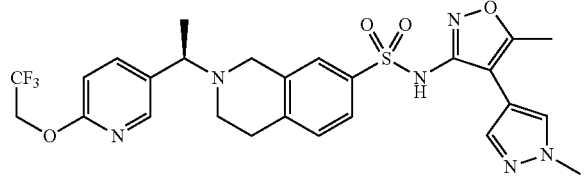 [SMILES: Cc1onc(NS(=O)(=O)c2ccc3c(c2)CN([C@H](C)c2ccc(OCC(F)(F)F)nc2)CC3)c1-c1cnn(C)c1]

50% wt. aqueous K₃PO₄ solution (500 uL, 1.76 mmol) was added to a mixture of (R)—N-(4-bromo-5-methylisoxazol-3-yl)-2-(1-(6-(2,2,2-trifluoroethoxy)pyridin-3-yl)ethyl)-1,2,3,4-tetrahydroisoquinoline-7-sulfonamide (200 mg, 0.348 mmol), 1-methyl-4-(4,4,5,5-tetramethyl-1,3,2-dioxaborolan-2-yl)-1H-pyrazole (152 mg, 0.73 mmol), and 1,1'-bis(di-tert-butylphosphino)ferrocene palladium dichloride (25 mg, 0.052 mmol) in DMF (2 mL). The reaction mixture was degassed with $N_2$ for 10 min then heated thermally at 90° C. for 40 min. The mixture was cooled and filtered through a syringe-driven filter unit, washing with ACN. The resulting solution was purified by reverse phase HPLC [SUNFIRE 18C, OBD column, 90-5% (0.1% TFA/$H_2O$)/(0.1% TFA/ACN) over 15 min]. The desired fractions were combined, neutralized with saturated aqueous NaHCO₃ solution, and extracted with EtOAc×3. The combined organic layers were dried over MgSO₄, filtered, and concentrated under reduced pressure to afford the title compound. ¹H NMR (500 MHz, CD₃Cl₃) δ 8.08 (s, 1H), 7.70 (d, 1H), 7.71-7.67 (m, 2H), 7.46 (s, 1H), 7.40 (s, 1H), 7.23 (d, 1H), 6.85 (d, 1H), 4.79 (q, 2H), 3.92 (s, 3H), 3.82 (d, 1H), 3.65-3.59 (m, 2H), 2.96-2.82 (m, 2H), 2.80-2.75 (m, 1H), 2.68-2.61 (m, 1H), 2.34 (s, 3H), 1.45 (d, 3H). LC/MS (m/z): 577 (M+H)⁺. MGAT2 Human IC₅₀: 24 nM.

Example 18

Preparation of (R)—N-(5-(2-hydroxypropan-2-yl)isoxazol-3-yl)-2-(1-(6-(2,2,2-trifluoroethoxy)pyridin-3-yl)ethyl)-1,2,3,4-tetrahydroisoquinoline-7-sulfonamide

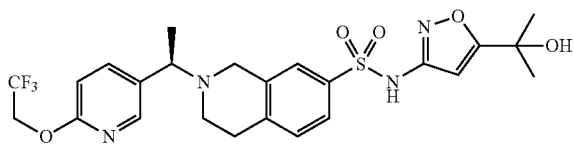 [SMILES: C[C@H](c1ccc(OCC(F)(F)F)nc1)N1CCc2ccc(S(=O)(=O)Nc3cc(C(C)(C)O)on3)cc2C1]

Step A: (R)-methyl 3-(2-(1-(6-(2,2,2-trifluoroethoxy)pyridin-3-yl)ethyl)-1,2,3,4-tetrahydroisoquinoline-7-sulfonamido)isoxazole-5-carboxylate

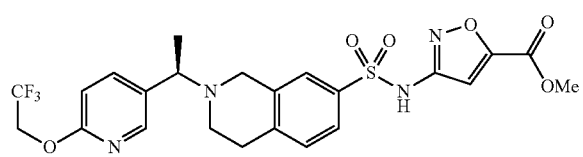 [SMILES: COC(=O)c1cc(NS(=O)(=O)c2ccc3c(c2)CN([C@H](C)c2ccc(OCC(F)(F)F)nc2)CC3)no1]

A solution of 1 M LiHMDS in THF (5.70 ml, 5.70 mmol) was added dropwise to a mixture of Intermediate 3 (1 g, 1.84 mmol) and methyl 3-aminoisoxazole-5-carboxylate (550 mg, 3.86 mmol) in anhydrous THF (6.1 ml) that had been cooled to −78° C. and placed under a $N_2$ atmosphere. The acetone bath was removed and the solution aged at room temperature for 3 hrs. The reaction was quenched with saturated aqueous NH₄Cl solution and diluted with EtOAc. The two layers were separated and the aqueous phase extracted with EtOAc×2. The combined organic layers were dried over MgSO₄, filtered, and concentrated under reduced pressure. The resulting crude was purified by MPLC (KP-Sil 25 g SNAP column, BIOTAGE system) eluting with a gradient of 2-9% MeOH/DCM over 20 CV to afford the target compound. LC/MS (m/z): 541 (M+H)⁺.

Step B: (R)—N-(5-(2-hydroxypropan-2-yl)isoxazol-3-yl)-2-(1-(6-(2,2,2-trifluoroethoxy)pyridin-3-yl)ethyl)-1,2,3,4-tetrahydroisoquinoline-7-sulfonamide

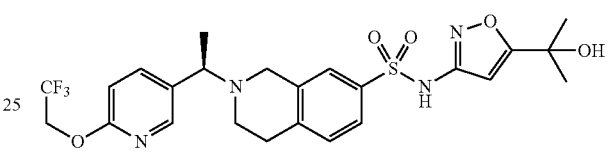

A solution of 3 M MeMgBr in THF (130 µl, 0.389 mmol) was added to a stirring solution of (R)-methyl-3-(2-(1-(6-(2,2,2-trifluoroethoxy)pyridin-3-yl)ethyl)-1,2,3,4-tetrahydroisoquinoline-7-sulfonamido)isoxazole-5-carboxylate (30 mg, 0.056 mmol) in THF (555 µL) that had been cooled to −78° C. and placed under a $N_2$ atmosphere. The reaction was allowed to slowly warm to room temperature overnight. The reaction was quenched with saturated aqueous NH₄Cl solution and diluted with EtOAc. The two layers were separated and the aqueous phase extracted with EtOAc×2. The combined organic layers were dried over MgSO₄, filtered, and concentrated under reduced pressure. The residue was loaded onto 1×2000 micron silica preparative TLC plate (uv 254 active) which was developed using 5% MeOH/DCM as the solvent system. The desired silica (Rf=0.4 @ 5% MeOH/DCM) was collected and extracted to afford the title compound. ¹H NMR (500 MHz, CD₃Cl₃) δ 8.07 (s, 1H), 7.72 (d, 1H), 7.59 (d, 1H), 7.51 (s, 1H), 7.19 (d, 1H), 6.88 (d, 1H), 6.33 (s, 1H), 4.79 (q, 2H), 3.80 (d, 1H), 3.68 (q, 1H), 3.61 (d, 1H), 2.98-2.79 (m, 3H), 2.76-2.64 (m, 1H), 1.57 (s, 6H), 1.47 (d, 3H). LC/MS (m/z): 541 (M+H)⁺. MGAT2 Human IC₅₀: 23 nM.

Example 19

Preparation of (R)—N-(5-(2-fluoropropan-2-yl)isoxazol-3-yl)-2-(1-(6-(2,2,2-trifluoroethoxy)pyridin-3-yl)ethyl)-1,2,3,4-tetrahydroisoquinoline-7-sulfonamide

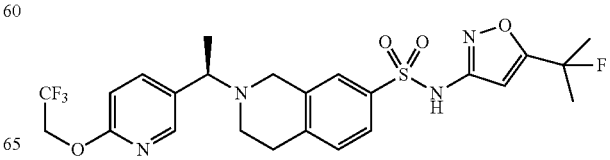

HF-Pyridine (400 µL, 4.44 mmol) was added to a stirring solution of (R)—N-(5-(2-hydroxypropan-2-yl)isoxazol-3-yl)-2-(1-(6-(2,2,2-trifluoroethoxy)pyridin-3-yl)ethyl)-1,2,3,4-tetrahydroisoquinoline-7-sulfonamide (compound of Example 18, 12 mg, 0.022 mmol) in anhydrous THF (222 µL) that had been placed under a $N_2$ atmosphere. This mixture was aged for 48 hrs then was diluted with EtOAc and neutralized by the slow addition of saturated aqueous $NaHCO_3$ solution. The two layers were separated and the aqueous phase extracted with EtOAc×3. The combined organic layers were dried over $MgSO_4$, filtered, and concentrated under reduced pressure. The residue was loaded onto 1×2000 micron silica preparative TLC plate (uv 254 active) which was developed using 5% MeOH/DCM as the solvent system. The desired silica (Rf=0.5 @ 5% MeOH/DCM) was collected and extracted to afford the title compound. $^1$H NMR (500 MHz, $CD_3Cl_3$) δ 8.09 (s, 1H), 7.71 (d, 1H), 7.59 (d, 1H), 7.52 (s, 1H), 7.22 (d, 1H), 6.88 (d, 1H), 6.49 (s, 1H), 4.79 (q, 2H), 3.81 (d, 1H), 3.67 (q, 1H), 3.60 (d, 1H), 2.98-2.84 (m, 2H), 2.82-2.75 (m, 1H), 2.72-2.63 (m, 1H), 1.76 (s, 3H), 1.71 (s, 3H), 1.49 (d, 3H). LC/MS (m/z): 543 (M+H)$^+$. MGAT2 Human $IC_{50}$: 18 nM.

Example 20

Preparation of N-(5-(tert-butyl)-4-methylisoxazol-3-yl)-2-((2-((2,2,2-trifluoroethyl)thio)pyrimidin-5-yl)methyl)-1,2,3,4-tetrahydroisoquinoline-7-sulfonamide

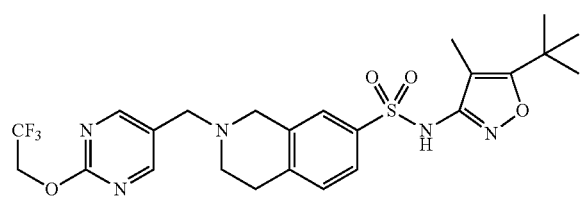 [SMILES: Cc1c(NS(=O)(=O)c2ccc3c(c2)CN(Cc2cnc(OCC(F)(F)F)nc2)CC3)noc1C(C)(C)C]

Step A: N-(5-(tert-butyl)-4-methylisoxazol-3-yl)-1,2,3,4-tetrahydroisoquinoline-7-sulfonamide

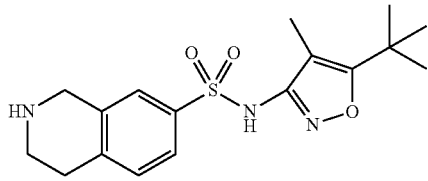 [SMILES: Cc1c(NS(=O)(=O)c2ccc3c(c2)CNCC3)noc1C(C)(C)C]

A solution of N-(4-bromo-5-(tert-butyl)isoxazol-3-yl)-2-(2,2,2-trifluoroacetyl)-1,2,3,4-tetrahydroisoquinoline-7-sulfonamide (Step C product of Example 10; 2 g, 3.92 mmol), 2,4,6-trimethyl-1,3,5,2,4,6-trioxatriborinane (50% wt in THF, 1.97 g, 7.84 mmol), 50% aqueous $K_3PO_4$ (6.66 g, 15.68 mmol), and Pd(DBPF)$Cl_2$ (128 mg, 0.196 mmol) in 12 mL of DMF was heated by microwave at 100° C. for 2 h. The reaction mixture was cooled to room temperature and filtered. The filtrate was purified directly by mass-directed reverse HPLC. The product containing fractions were collected and lyophilized to afford the product. LC/MS (m/z): 350 (M+H)$^+$.

Step B: N-(5-(tert-butyl)-4-methylisoxazol-3-yl)-2-((2-chloropyrimidin-5-yl)methyl)-1,2,3,4-tetrahydroisoquinoline-7-sulfonamide

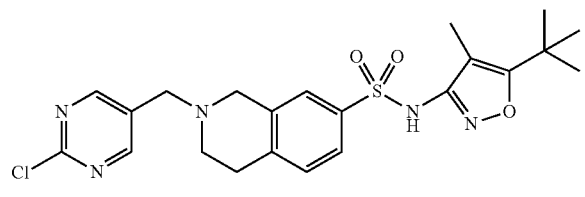 [SMILES: Cc1c(NS(=O)(=O)c2ccc3c(c2)CN(Cc2cnc(Cl)nc2)CC3)noc1C(C)(C)C]

Step A product (184 mg, 0.527 mmol) and 2-chloropyrimidine-5-carbaldehyde were dissolved in a mixture of 5 mL of THF and 1 mL of MeOH. AcOH 0.151 mL, 2.63 mmol) was added and the mixture was stirred at room temperature for 10 min. The resin-bound reducing agent MP-CN $BH_3$ (2.22 mmol/g; 0.972 mmol, 438 mg) was added. The reaction was stirred at room temperature overnight. The mixture was filtered to remove solid (resin and some starting material zwitterion). The filtrate was made basic with aq $NaHCO_3$, extracted with EtOAc. The organics were washed with brine, dried and concentrated. The residue was purified by silica column (3-5% MeOH in DCM; product Rf=0.3 @ 5% MeOH in DCM) to afford the product. LC/MS (m/z): 476 (M+H)$^+$.

Step C: N-(5-(tert-butyl)-4-methylisoxazol-3-yl)-2-((2-((2,2,2-trifluoroethyl)thio)pyrimidin-5-yl)methyl)-1,2,3,4-tetrahydroisoquinoline-7-sulfonamide

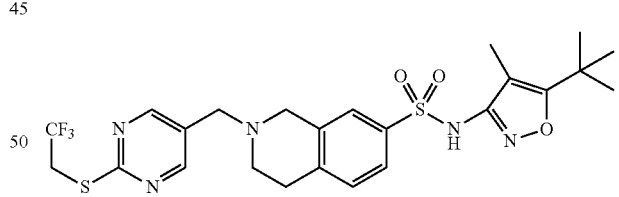

Step B product (20 mg, 0.042 mmol) and trifluoroethylthiol (14.6 mg, 0.126 mmol) were dissolved in 1 mL of DMF, to which was added NaH (60%, 5 mg, 0.126 mmol). The reaction was stirred at room temperature for 15 min. Then the mixture was extracted with EtOAc and the organics were washed with water (2×) and brine, dried and concentrated. The residue was purified by silica column (3-5% MeOH in DCM; product Rf=0.3 @ 5% MeOH in DCM) to afford the product. $^1$H NMR (500 MHz, $CDCl_3$) δ 8.64 (s, 2H), 7.78 (d, 1H), 7.68 (s, 1H), 7.22 (d, 1H), 4.22 (q, 2H), 3.83 (br s, 2H), 3.78 (br s, 2H), 3.03 (br s, 2H), 2.85 (br s, 2H), 2.01 (s, 3H), 1.38 (s, 9H). LC/MS (m/z): 556 (M+H)$^+$. MGAT2 Human $IC_{50}$: 5.8 nM.

Example 21

Preparation of (E)-N-(5-(tert-butyl)-4-(prop-1-en-1-yl)isoxazol-3-yl)-2-((2-(2,2,2-trifluoroethoxy)thiazol-5-yl)methyl)-1,2,3,4-tetrahydroisoquinoline-7-sulfonamide

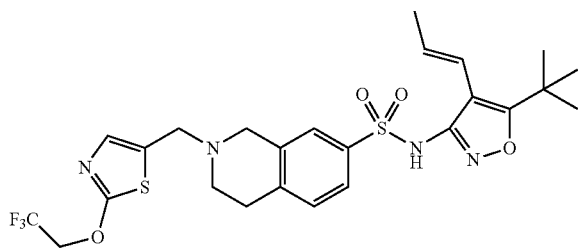 [SMILES: C/C=C/c1c(NS(=O)(=O)c2ccc3c(c2)CN(Cc2cnc(OCC(F)(F)F)s2)CC3)noc1C(C)(C)C]

Step A: (E)-N-(5-(tert-butyl)-4-(prop-1-en-1-yl)isoxazol-3-yl)-1,2,3,4-tetrahydroisoquinoline-7-sulfonamide

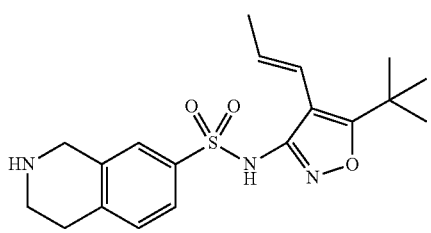 [SMILES: C/C=C/c1c(NS(=O)(=O)c2ccc3c(c2)CNCC3)noc1C(C)(C)C]

The title compound was prepared following the procedure described in Step A of Example 20 but using (E)-prop-1-en-1-ylboronic acid. LC/MS (m/z): 376 (M+H)$^+$.

Step B: Methyl 2-(2,2,2-trifluoroethoxy)thiazole-5-carboxylate

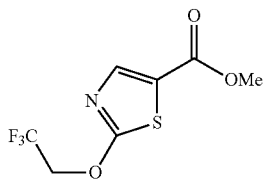 [SMILES: COC(=O)c1cnc(OCC(F)(F)F)s1]

The title compound was prepared following the procedure described in Step C of Example 20 but using commercially available methyl 2-chlorothiazole-5-carboxylate. LC/MS (m/z): 242 (M+H)$^+$.

Step C: N-methoxy-N-methyl-2-(2,2,2-trifluoroethoxy)thiazole-5-carboxamide

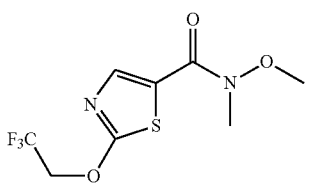 [SMILES: CON(C)C(=O)c1cnc(OCC(F)(F)F)s1]

Methyl 2-(2,2,2-trifluoroethoxy)thiazole-5-carboxylate (55 mg, 0.228 mmol) and Me(MeO)NH HCl (44.6 mg, 0.456 mmol) were slurried in THF and cooled to −20° C. under N$_2$. A solution of $^i$PrMgCl in Et2O (2 M, 0.456 mL, 0.912 mmol)) was added over 5 min maintaining the temperature below −5° C. The mixture was aged for 20 min at −10° C. and quenched with aqueous NH$_4$Cl. The mixture was extracted with EtOAc, and the organics were washed with water (2×) and brine, dried and concentrated. The crude Weinreb amide was used in the next step without further purification. LC/MS (m/z): 271 (M+H)$^+$.

Step D: 2-(2,2,2-trifluoroethoxy)thiazole-5-carbaldehyde

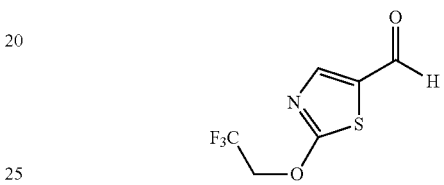

Weinreb amide from Step C (55 mg, 0.204 mmol) was dissolved in 1.5 mL of THF, and the solution was cooled to −78° C., to which DIBAL-H in hexanes (1 M, 0.305 mL, 0.305 mmol) was slowly added. After 10 min at −78 C, the reaction was quenched with aqueous Rochelle salt at −78° C. The mixture was warmed up to room temperature and extracted with EtOAc, and the organics were washed with water (2×) and brine, dried and concentrated. The aldehyde thus obtained was used in the next step without further purification. $^1$H NMR (500 MHz, CDCl$_3$) δ 9.86 (s, 1H), 7.84 (s, 1H), 4.93 (q, 2H).

Step E: (E)-N-(5-(tert-butyl)-4-(prop-1-en-1-yl)isoxazol-3-yl)-2-((2-(2,2,2-trifluoroethoxy)thiazol-5-yl)methyl)-1,2,3,4-tetrahydroisoquinoline-7-sulfonamide

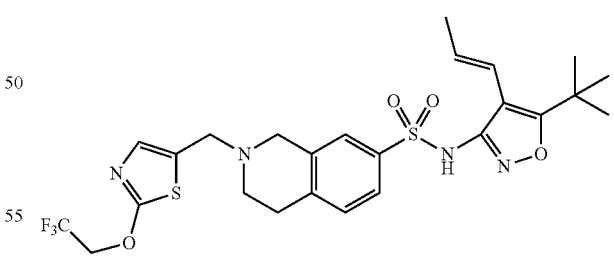

The reductive amination between amine from Step A and aldehyde from Step D was conducted following the procedure described in Step B of Example 20, which afforded the title compound. $^1$H NMR (500 MHz, CDCl$_3$) δ 7.88 (d, 1H), 7.79 (s, 1H), 7.28 (d, 1H), 7.04 (s, 1H), 6.08 (d, 1H), 5.82 (m, 1H), 4.82 (q, 2H), 3.83 (br s, 2H), 3.79 (br s, 2H), 3.02 (br s, 2H), 2.84 (br s, 2H), 1.88 (d, 3H), 1.33 (s, 9H). LC/MS (m/z): 571 (M+H)$^+$. MGAT2 Human IC$_{50}$: 3.9 nM.

Example 22

Preparation of 7-(N-(5-(tert-butyl)isoxazol-3-yl)sulfamoyl)-2-((R)-(1-(6-(2,2-difluoroethoxy)pyridin-3-yl)ethyl)-1,2,3,4-tetrahydroisoquinolin-2-ium 2,2,2-trifluoroacetate

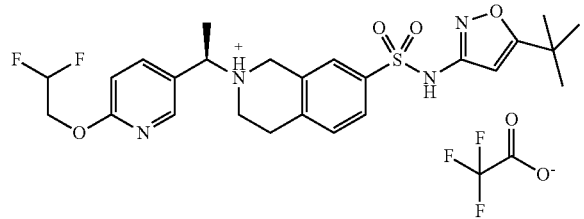

Step A:
1-(6-(2,2-difluoroethoxy)pyridin-3-yl)ethanone

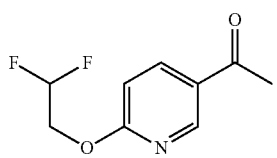

In a flame-dried 250 mL round bottom flask, 1-(6-chloro-3-pyridinyl)-1-ethanone (5 g, 28.9 mmol) was dissolved in anhydrous DMF (54.0 ml). 2,2-difluoroethanol (2.75 ml, 43.4 mmol) was added to the above mixture at 0° C., under $N_2$, followed with the addition of sodium hydride (1.735 g, 43.4 mmol) portionwise. The mixture was stirred at 0° C. for 10 min, then 1 h at room temperature. LC/MS showed the starting material was completely consumed. The mixture was quenched with saturated aqueous $NH_4Cl$ solution, and extracted with EtOAc. The organic layer was dried over $MgSO_4$, then filtered and the filtrate was concentrated with rotavap. The crude material was purified by ISCO flash column, 80 g column, 0-20% EtOAc/hexane to afford the title compound. $R_f$=0.20 (20% EtOAc/hex.) LC/MS (m/z): 202 (M+H)$^+$.

Step B: (R)-1-(6-(2,2-difluoroethoxy)pyridin-3-yl)ethanamine

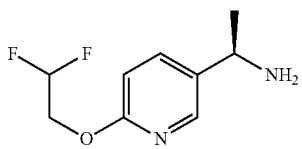

A 500 mL round bottom flask was charged with enzyme CDX-017 (4.2 g), PLP (520 mg), and phosphate buffer (0.2 M, pH 7.0, 187 mL). The mixture was stirred at 40° C. 1-(6-(2,2-Difluoroethoxy)pyridin-3-yl)ethanone (5.066 g, 25.2 mmol) was dissolved in DMSO (20.64 ml), which was added to the above reaction mixture, followed by addition of isopropylamine (20.06 ml, 234 mmol). It was stirred at 40° C. over night. LC/MS showed the conversion was complete. The mixture was extracted with EtOAc (3×), and the combined organic layers were dried over $MgSO_4$, and evaporated to afford the title compound. $^1H$ NMR showed about 8% starting material and the majority was the product.

Step C: (R)-7-bromo-2-(1-(6-(2,2-difluoroethoxy)pyridin-3-yl)ethyl)-1,2,3,4-tetrahydroisoquinoline

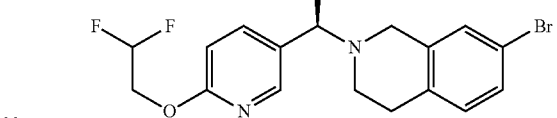

A 250 mL round bottom flask was charged with (R)-1-(6-(2,2-difluoroethoxy)pyridin-3-yl)ethanamine (5 g, 19.53 mmol), 4-bromo-1-(2-bromoethyl)-2-(bromomethyl)benzene (6.97 g, 19.53 mmol), potassium carbonate (8.10 g, 58.6 mmol) and EtOH (43.0 ml). It was heated at 90° C., under $N_2$, for about 2 h. The reaction mixture was filtered, and the filtrate was concentrated under reduced pressure. The crude material was purified by ISCO flash column (125 g column; eluting with 0-20% EtOAc/hex) to afford the title compound, containing 90% pure product, and 10% 1-(6-(2,2-difluoroethoxy)pyridin-3-yl)ethanone, the precursor of the amine. $R_f$=0.23 (20% EtOAc/hex.) LC/MS (m/z): 397 (M+H)$^+$.

Step D: (R)-7-(benzylthio)-2-(1-(6-(2,2-difluoroethoxy)pyridin-3-yl)ethyl)-1,2,3,4-tetrahydroisoquinoline

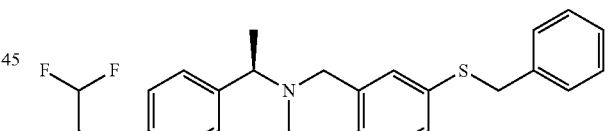

DIPEA (5.54 ml, 31.7 mmol) was added to a solution of (R)-7-bromo-2-(1-(6-(2,2-difluoroethoxy)pyridin-3-yl)ethyl)-1,2,3,4-tetrahydroisoquinoline (7.0 g, 15.86 mmol) in 1,4-Dioxane (70.8 ml). The mixture was evacuated and backfilled with $N_2$ (3×). tris(dibenzylidene-acetone)dipalladium(0) (0.363 g, 0.396 mmol), 4,5-bis(diphenylphosphino)-9,9-dimethylxanthene (0.642 g, 1.110 mmol) and benzyl mercaptan (1.876 ml, 15.86 mmol) were added subsequently and the mixture was degassed 2 times. The mixture was heated to reflux for 2 h. LC/MS showed the starting material was consumed. The reaction mixture was filtered, and the filtrate was concentrated under reduced pressure. The crude material was purified by ISCO (120 g column; 0-20% EtOAc/hex) to afford the title compound (7.217 g, 100% yield, 97% pure). Rf=0.20 (20% EtOAc/hex). LC/MS (m/z): 441 (M+H)$^+$.

Step E: (R)-2-(1-(6-(2,2-difluoroethoxy)pyridin-3-yl)ethyl)-1,2,3,4-tetrahydroisoquinoline-7-sulfonyl Chloride

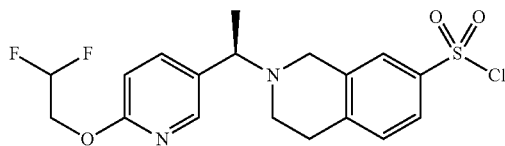 [SMILES: C[C@H](c1ccc(OCC(F)F)nc1)N1CCc2ccc(S(=O)(=O)Cl)cc2C1]

Acetic acid (1.559 ml, 27.2 mmol), water (0.491 ml, 27.2 mmol) and sulfuryl chloride (2.215 ml, 27.2 mmol) were added to a solution of (R)-7-(benzylthio)-2-(1-(6-(2,2-difluoroethoxy)pyridin-3-yl)ethyl)-1,2,3,4-tetrahydroisoquinoline (3 g, 6.81 mmol) in CH$_2$Cl$_2$ (58.2 ml) at room temperature under N$_2$. The mixture was stirred at room temperature overnight. The reaction mixture was partitioned between CH$_2$Cl$_2$ and saturated aqueous NaHCO$_3$ solution. The organic phase was separated, dried over MgSO$_4$, and concentrated to afford the title compound, which was used for the next step without further purification.

Step F: 7-(N-(5-(tert-butyl)isoxazol-3-yl)sulfamoyl)-2-((R)-(1-(6-(2,2-difluoroethoxy)pyridin-3-yl)ethyl)-1,2,3,4-tetrahydroisoquinolin-2-ium 2,2,2-trifluoroacetate

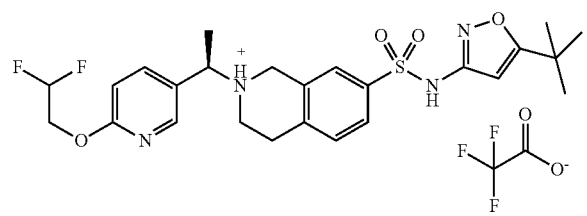

3-amino-5-tert-butylisoxazole (59.2 mg, 0.422 mmol) and anhydrous THF (2111 µl) were added, under N$_2$, to a 40 mL vial containing (R)-2-(1-(6-(2,2-difluoroethoxy)pyridin-3-yl)ethyl)-1,2,3,4-tetrahydroisoquinoline-7-sulfonyl chloride (100 mg, 0.211 mmol). It was cooled to −78° C. Lithium bis(trimethylsilyl)amide (633 µl, 0.633 mmol) (1M in THF) was added to the above solution dropwise, and it was stirred at −78° C. for 5 min then warmed up slowly to room temperature, and stirred at room temperature for 1 h. The reaction was quenched with saturated aqueous NH$_4$Cl (5 mL). The two layers were separated. The aqueous layer was extracted with EtOAc (20 mL×2). The combined organic layers were dried over MgSO$_4$, filtered and concentrated. The residue was purified with ISCO, 24 g column, 0-50% EtOAc/hex. The residue was dissolved in ACN, and purified with Gilson SunFire™ Prep C18 OBD™ 30×100 mm Column, Part No. 186002572, WATERS, 25-60% ACN/H$_2$O with 0.1% TFA, 10 min. run, monitored at 220 nm, collected at 7-9 min and lyophilized to afford the title compound $^1$H NMR (500 MHz, CDCl$_3$) δ 8.18 (s, 1H), 7.84 (d, 1H), 7.74 (d, 1H), 7.65 (s, 1H), 7.31 (d, 1H), 6.96 (d, 1H), 6.12 (m, 2H), 4.56 (m, 3H), 4.35 (br, 1H), 3.24 (br, 4H), 1.84 (d, 3H), 1.30 (s, 9H). LC/MS (m/z): 521 (M+H)$^+$. MGAT2 Human IC$_{50}$: 6.4 nM.

Example 23

Preparation of (R)-5-cyclopropyl-3-(2-(1-(6-(2,2-difluoroethoxy)pyridin-3-yl)ethyl)-1,2,3,4-tetrahydroisoquinoline-7-sulfonamido)-1,2,4-oxadiazol-2-ium 2,2,2-trifluoroacetate

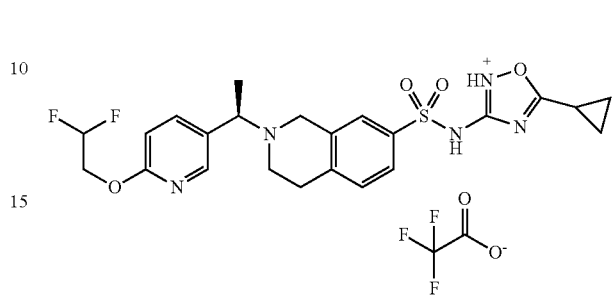

Under N$_2$, to a 100 mL round bottom flask containing (R)-2-(1-(6-(2,2-difluoroethoxy)pyridin-3-yl)ethyl)-1,2,3,4-tetrahydroisoquinoline-7-sulfonyl chloride from Example 22, Step E (500 mg, 0.540 mmol), 5-cyclopropyl-1,2,4-oxadiazol-3-amine, (88 mg, 0.702 mmol) and anhydrous THF (5.4 ml) was added. It was cooled to −78° C. Lithium bis(trimethylsilyl)amide (1.079 ml, 1.079 mmol) (1M in THF) was added to the above solution dropwise, and it was stirred at −78° C. for 5 min then warmed up slowly to room temperature and stirred for 1 h. The reaction was quenched with saturated aqueous NH$_4$Cl solution (5 mL). The two layers were separated. The aqueous layer was extracted with EtOAc (20 mL×2). The combined organic layers were dried over MgSO$_4$, filtered and concentrated under reduced pressure. The residue was purified with ISCO, 40 g column, 0-7% MeOH/CH$_2$Cl$_2$. The residue was dissolved in ACN, and purified with Gilson SunFire™ Prep C18 OBD™ 30×100 mm Column, Part No. 186002572, WATERS, 25-50% ACN/H$_2$O with 0.1% TFA, 10 min. run, monitored at 220 nm, collected at 5-8 min and lyophilized to afford the title compound. $^1$H NMR (500 MHz, CDCl$_3$) δ 8.14 (s, 1H), 7.68 (d, 1H), 7.68 (d, 1H), 7.61 (s, 1H), 7.35 (d, 1H), 6.96 (d, 1H), 6.14 (tt, 1H), 4.58 (m, 2H), 4.51 (t, 1H), 4.30 (br, 2H), 3.35 (br, 2H), 3.26 (br, 2H), 2.11 (m, 1H), 1.87 (d, 3H), 1.20 (m, 4H). LC/MS (m/z): 506 (M+H)$^+$. MGAT2 Human IC$_{50}$: 8.2 nM.

Example 24

Preparation of (R)-5-cyclopropyl-3-(2-(1-(5-(2,2-difluoroethoxy)pyrazin-2-yl)ethyl)-1,2,3,4-tetrahydroisoquinoline-7-sulfonamido)-1,2,4-oxadiazol-2-ium 2,2,2-trifluoroacetate

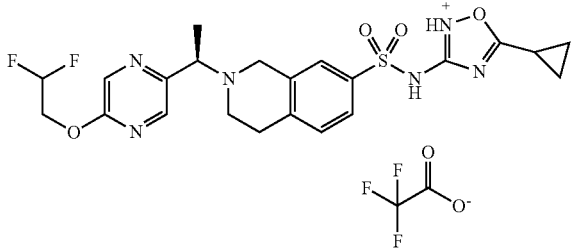 [SMILES: C[C@H](c1cnc(OCC(F)F)cn1)N1CCc2ccc(S(=O)(=O)Nc3noc(C4CC4)n3)cc2C1 ; O=C([O-])C(F)(F)F]

5-cyclopropyl-1,2,4-oxadiazol-3-amine (37.8 mg, 0.302 mmol) and dry THF (2326 µl) were added under N₂, to a 40 mL vial containing Intermediate 6 (120 mg, 0.233 mmol). It was cooled to −78° C. Lithium bis(trimethylsilyl)amide (465 µl, 0.465 mmol) (1M in THF) was added to the above solution dropwise, and it was stirred at −78° C. for 5 min, then warmed up slowly to room temperature and stirred for 1 h. The reaction was quenched with saturated aqueous NH₄Cl (5 mL). The two layers were separated. The aqueous layer was extracted with EtOAc (20 mL×2). The combined organic layers was dried over MgSO₄, filtered and concentrated under reduced pressure. The residue was purified with prep. TLC plate (5% MeOH/CH₂Cl₂). Then it was dissolved in ACN, and purified with Gilson SunFire™ Prep C18 OBD™ 30×100 mm Column, Part No. 186002572, WATERS, 25-60% ACN/H₂O with 0.1% TFA, 10 min. run, monitored at 220 nm, collected at 6-7 min. and lyophilized to afford the title compound. ¹H NMR (600 MHz, CDCl₃) δ 8.34 (s, 1H), 8.27 (s, 1H), 7.93 (d, 1H), 7.81 (s, 1H), 7.31 (d, 1H), 6.12 (tt, 1H), 4.99 (q, 1H), 4.69 (d, 1H), 4.57 (t, 2H), 4.44 (br, 1H), 3.59 (br, 1H), 3.28 (br, 2H), 3.20 (br, 1H), 2.15 (m, 1H), 1.81 (d, 3H), 1.18 (m, 4H). LC/MS (m/z): 507 (M+H)⁺. MGAT2 Human IC₅₀: 19.7 nM.

Example 25

Preparation of 7-(N-(5-(tert-butyl)-4-methylisoxazol-3-yl)sulfamoyl)-2-((R)-1-(5-(2,2-difluoroethoxy)pyrazin-2-yl)ethyl)-1,2,3,4-tetrahydroisoquinolin-2-ium 2,2,2-trifluoroacetate

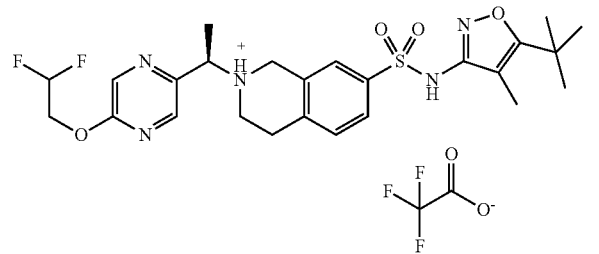

3-amino-4-methyl-5-tert-butylisoxazole (71.7 mg, 0.465 mmol) and dry THF (3877 µl) were added under N₂ to a 40 mL vial containing Intermediate 6 (200 mg, 0.388 mmol). It was cooled to −78° C. Lithium bis(trimethylsilyl)amide (775 µl, 0.775 mmol) (1M in THF) was added to the above solution dropwise, and it was stirred at −78° C. for 5 min. then warmed up slowly to room temperature, and stirred for 1 h. The reaction was quenched with saturated aqueous NH₄Cl (5 mL). The two layers were separated. The aqueous layer was extracted with EtOAc (20 mL×2). The combined organic layers were dried over MgSO₄, filtered and concentrated under reduced pressure. The residue was purified with prep. TLC plate (50% EtOAc/hex.). A second purification was needed. The product containing fractions were dissolved in ACN, and purified with Gilson SunFire™ Prep C18 OBD™ 30×100 mm Column, Part No. 186002572, WATERS, 25-50% ACN/H₂O with 0.1% TFA, 10 min. run, monitored at 220 nm, collected at 8-10 min. and lyophilized to afford the title compound. ¹H NMR (600 MHz, CDCl₃) δ 8.34 (s, 1H), 8.27 (s, 1H), 7.83 (d, 1H), 7.76 (s, 1H), 7.30 (d, 1H), 6.94 (br, 1H), 6.12 (tt, 1H), 4.96 (q, 1H), 4.69 (d, 1H), 4.58 (m, 2H), 4.46 (br, 1H), 3.62 (br, 1H), 3.27 (br, 2H), 3.20 (br, 2H), 1.96 (s, 3H), 1.82 (d, 3H), 1.33 (s, 9H). LC/MS (m/z): 536 (M+H)⁺. MGAT2 Human IC₅₀: 4.6 nM.

Example 26

Preparation of (R)-5-cyclopropyl-3-(2-(1-(6-((3,3-difluorocyclobutyl)methoxy)pyridin-3-yl)ethyl)-1,2,3,4-tetrahydroisoquinoline-7-sulfonamido)-1,2,4-oxadiazol-2-ium 2,2,2-trifluoroacetate

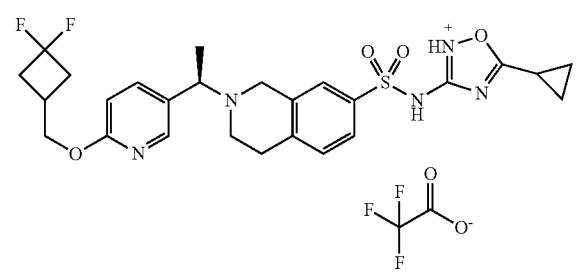 [SMILES: C[C@H](c1ccc(OCC2CC(F)(F)C2)nc1)N1CCc2ccc(S(=O)(=O)Nc3noc(C4CC4)n3)cc2C1 ; O=C([O-])C(F)(F)F]

Step A: 1-(6-((3,3-difluorocyclobutyl)methoxy)pyridin-3-yl)ethanone

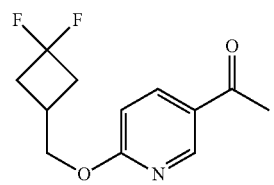

In a flame-dried 250 mL round bottom flask, 1-(6-chloro-3-pyridinyl)-1-ethanone (3 g, 17.35 mmol) was dissolved in anhydrous DMF (32.4 ml). (3,3-Difluorocyclobutyl)methanol (3.18 g, 26.0 mmol) was added to the above mixture at 0° C., under N₂, followed with the addition of sodium hydride (1.041 g, 26.0 mmol) portionwise. The mixture was stirred at 0° C. for 10 min. then 1 h at room temperature. LC/MS showed the starting material was completely consumed. The reaction was quenched with saturated aqueous NH₄Cl, extracted with EtOAc, dried over MgSO₄, and concentrated. The crude material was purified with ISCO flash column, 80 g column, 0-30% EtOAc/hex. to afford the title compound. R_f=0.34 (30% EtOAc/hex.) LC/MS (m/z): 242 (M+H)⁺.

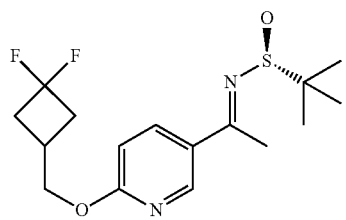

Step B

A 250 mL round bottle was flame dried. It was charged with 1-(6-((3,3-difluorocyclobutyl)methoxy)pyridin-3-yl)

ethanone (3 g, 12.44 mmol), (R)-(+)-2-methyl-2-propane-sulfinamide (1.959 g, 16.17 mmol) and THF (56.3 ml). Titanium(IV) ethoxide (5.16 ml, 24.87 mmol) was added to the solution under nitrogen. The reaction was heated at 60° C. for 3 h then cooled to room temperature. The mixture was concentrated under reduced pressure and purified with ISCO, 80 g column, dry load, 0-30% EtOAc/hexane to afford the title compound. $R_f$=0.29 (50% EtOAc/hex.) LC/MS (m/z): 345 (M+H)⁺.

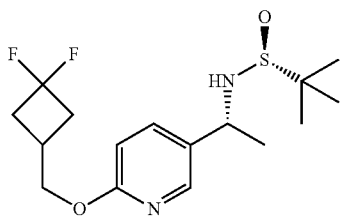

Step C

The material from Step B (2.5714 g, 7.47 mmol) was dissolved in 98:2 THF/H₂O (18.6 mL) and cooled to −50° C. Titanium(IV) ethoxide (0.310 ml, 1.493 mmol) and sodium borohydride (0.847 g, 22.40 mmol) were then added to the mixture, and the resulting solution was warmed to room temperature over a 3 h period. The LC/MS showed no more starting material. The solvent was removed in vacuo, and the resulting residue was stirred with CH₂Cl₂. The mixture was filtered through CELITE, and the filtrate was concentrated to furnish product which was purified with ISCO, 40 g column, 0-8% MeOH/CH₂Cl₂, to afford the title compound. $R_f$=0.08 (50% EtOAc/hex.) LC/MS (m/z): 347 (M+H)⁺.

Step D: (R)-1-(6-((3,3-difluorocyclobutyl)methoxy)pyridin-3-yl)ethanamine

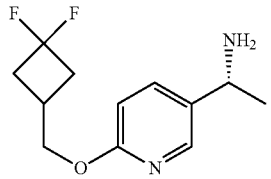

The material from Step C (1.856 g, 5.36 mmol) was treated with 4M HCl in dioxane (13.89 mL) and stirred at room temperature over night. LC/MS showed the reaction was complete. Solvents were removed in vacuo to afford the title compound. LC/MS (m/z): 243 (M+H)⁺.

Step E: (R)-7-bromo-2-(1-(6-((3,3-difluorocyclobutyl)methoxy)pyridin-3-yl)ethyl)-1,2,3,4-tetrahydroisoquinoline

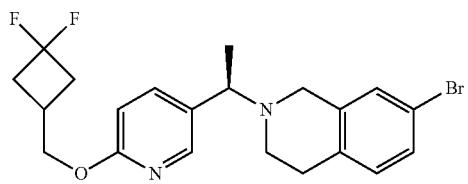 [SMILES: C[C@H](c1ccc(OCC2CC(F)(F)C2)nc1)N1CCc2ccc(Br)cc2C1]

DIPEA (4.66 ml, 26.7 mmol) was added to a suspension of (R)-1-(6-((3,3-difluorocyclobutyl)methoxy)pyridin-3-yl)ethanamine (2.2121 g, 5.33 mmol) in EtOH (35.6 ml), at room temperature and it turned clear. 4-bromo-1-(2-bromo-ethyl)-2-(bromomethyl)benzene (1.904 g, 5.33 mmol) was added to this solution in one portion and stirred at 80° C. for 3 h. It was cooled to room temperature, and concentrated under reduced pressure. The residue was participated between ethyl acetate and water. The organic layer was washed with brine, dried over sodium sulfate, filtrated and concentrated. The residue was purified with ISCO flash column, 125 g column, 0-20% EtOAc/hexane to afford the title compound. $R_f$=0.31 (30% EtOAc/hex.) LC/MS (m/z): 437 (M+H)⁺.

Step F: (R)-7-(benzylthio)-2-(1-(6-((3,3-difluorocyclobutyl)methoxy)pyridin-3-yl)ethyl)-1,2,3,4-tetrahydroisoquinoline

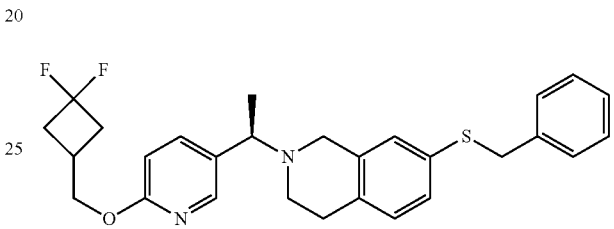

DIPEA (0.996 ml, 5.70 mmol) was added to a solution of (R)-7-bromo-2-(1-(6-((3,3-difluorocyclobutyl)methoxy)pyridin-3-yl)ethyl)-1,2,3,4-tetrahydroisoquinoline (1.2471 g, 2.85 mmol) in 1,4-Dioxane (12.73 ml). The mixture was evacuated and backfilled with N₂ (3×). Tris(dibenzylideneacetone)dipalladium(0) (0.065 g, 0.071 mmol), 4,5-bis(diphenylpophino)-9,9-dimethylxanthene (0.116 g, 0.200 mmol) and benzyl mercaptan (0.337 ml, 2.85 mmol) were added subsequently and the mixture was degassed 2×. The mixture was heated to reflux for 2 h. LC/MS showed the starting material was consumed. The mixture was filtered, washed with EtOAc, and concentrated. The crude material was purified with ISCO, 80 g column, (0-20% EtOAc/hex.) to afford the title compound. $R_f$=0.39 (30% EtOAc/hex.) LC/MS (m/z): 481 (M+H)⁺.

Step G: (R)-2-(1-(6-((3,3-difluorocyclobutyl)methoxy)pyridin-3-yl)ethyl)-1,2,3,4-tetrahydroisoquinoline-7-sulfonyl Chloride

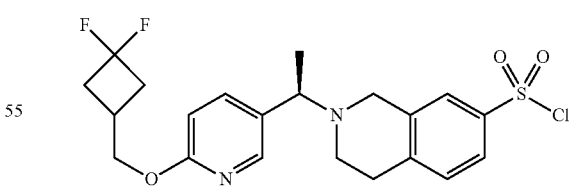

Acetic acid (0.588 ml, 10.27 mmol), water (0.185 ml, 10.27 mmol) and sulfuryl chloride (0.835 ml, 10.27 mmol) were added to a solution of (R)-7-(benzylthio)-2-(1-(6-((3,3-difluorocyclobutyl)methoxy)pyridin-3-yl)ethyl)-1,2,3,4-tetrahydroisoquinoline (1.23 g, 2.57 mmol) in CH₂Cl₂ (21.94 ml) at room temperature under N₂. It was stirred at room temperature over night. Then additional sulfuryl chloride (0.835 ml, 10.27 mmol) was added to the reaction mixture and it was stirred for 2 hours. The mixture was partitioned between CH₂Cl₂ and saturated NaHCO₃. The organic phase was separated, dried over MgSO₄, and concentrated to afford the title compound, which was used for the next step without further purification. LC/MS (m/z): 457 (M+H)⁺.

Step H: (R)-5-cyclopropyl-3-(2-(1-(6-((3,3-difluoro-cyclobutyl)methoxy)pyridin-3-yl)ethyl)-1,2,3,4-tetrahydroisoquinoline-7-sulfonamido)-1,2,4-oxadiazol-2-ium 2,2,2-trifluoroacetate

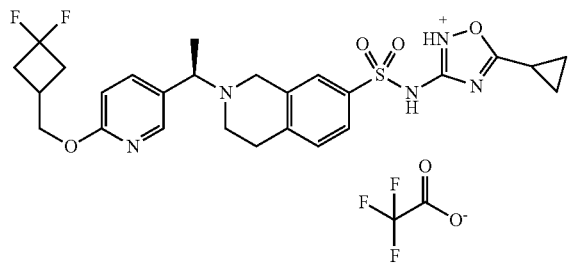 [SMILES: C[C@H](c1ccc(OCC2CC(F)(F)C2)nc1)N1CCc2ccc(S(=O)(=O)Nc3noc(C4CC4)n3)cc2C1 ; O=C([O-])C(F)(F)F]

5-cyclopropyl-1,2,4-oxadiazole-3-amine (53.4 mg, 0.427 mmol) and dry THF (3283 µl) were added under N₂, to a 40 mL vial containing (R)-2-(1-(6-((3,3-difluorocyclobutyl)methoxy)-pyridin-3-yl)ethyl)-1,2,3,4-tetrahydroisoquinoline-7-sulfonyl chloride (150 mg, 0.328 mmol) and 1,2,4-oxadiazol-3-amine. It was cooled to −78° C. Lithium bis(trimethylsilyl)amide (657 µl, 0.657 mmol) (1M in THF) was added to the above solution dropwise, and it was stirred at −78° C. for 5 min, then warmed up slowly to room temperature and stirred for 1 h. The reaction was quenched with saturated NH₄Cl (5 mL). The two layers were separated. The aqueous layer was extracted with EtOAc (20 mL×2). The combined organic layers were dried over MgSO₄, filtered and concentrated. The residue was purified with ISCO, 12 g column, 0-7% MeOH/CH₂Cl₂. R$_f$=0.17 (5% MeOH/CH₂Cl₂). The residue was dissolved in ACN, and purified with Gilson SunFire™ Prep C18 OBD™ 30×100 mm Column, Part No. 186002572, WATERS, 25-50% ACN/H₂O with 0.1% TFA, 10 min. run, monitored at 220 nm, collected at 7-9 min. and lyophilized to afford the title compound. ¹H NMR (500 MHz, CDCl₃) δ 8.15 (s, 1H), 7.96 (d, 2H), 7.82 (m, 2H), 7.34 (d, 1H), 6.86 (d, 1H), 4.54 (q, 1H), 4.36 (d, 2H), 3.24 (br, 4H), 2.71 (m, 2H), 2.64 (m, 1H), 2.44 (m, 2H), 2.14 (m, 1H), 1.86 (m, 3H), 1.19 (m, 4H). LC/MS (m/z): 546 (M+H)⁺. MGAT2 Human IC$_{50}$: 20.0 nM.

Example 27

Preparation of N-(5-(tert-butyl)-4-methylisoxazol-3-yl)-2-(6-(2,2,2-trifluoroethoxy)nicotinoyl)-1,2,3,4-tetrahydroisoquinoline-7-sulfonamide

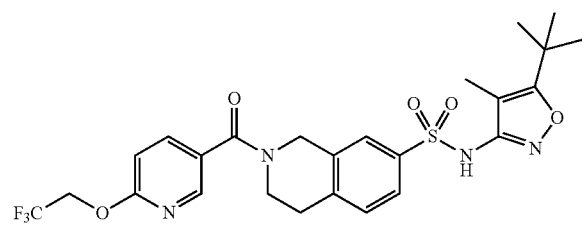 [SMILES: Cc1c(NS(=O)(=O)c2ccc3c(c2)CN(C(=O)c2ccc(OCC(F)(F)F)nc2)CC3)noc1C(C)(C)C]

Step A: N-(5-(tert-butyl)-4-methylisoxazol-3-yl)-1,2,3,4-tetrahydroisoquinoline-7-sulfonamide

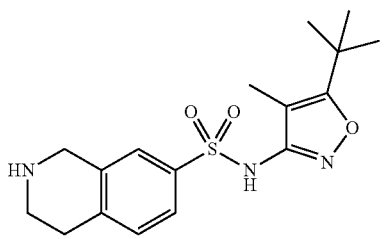 [SMILES: Cc1c(NS(=O)(=O)c2ccc3c(c2)CNCC3)noc1C(C)(C)C]

1,1'-bis(di-tert-butylphosphino)ferrocenepalladium dichloride (0.128 g, 0.196 mmol) and aqueous potassium phosphate tribasic (3.33 g, 7.84 mmol) were added to a mixture of N-(4-bromo-5-(tert-butyl)isoxazol-3-yl)-2-(2,2,2-trifluoroacetyl)-1,2,3,4-tetrahydroisoquinoline-7-sulfonamide (from Example 10 Step C, 1 g, 1.96 mmol) and trimethylboroxine (1.096 ml, 3.92 mmol) in DMF (10 ml) under nitrogen. The mixture was heated 100° C. in a microwave for 1 h, then was partitioned between EtOAc and water, and the aqueous phase was concentrated to dryness. The crude residue was extracted with absolute EtOH three times and was concentrated to yield N-(5-(tert-butyl)-4-methylisoxazol-3-yl)-1,2,3,4-tetrahydroisoquinoline-7-sulfonamide, which was used without further purification. LCMS (m/z): 350.1 (M+H)⁺.

Step B: N-(5-(tert-butyl)-4-methylisoxazol-3-yl)-2-(6-chloronicotinoyl)-1,2,3,4-tetrahydroisoquinoline-7-sulfonamide

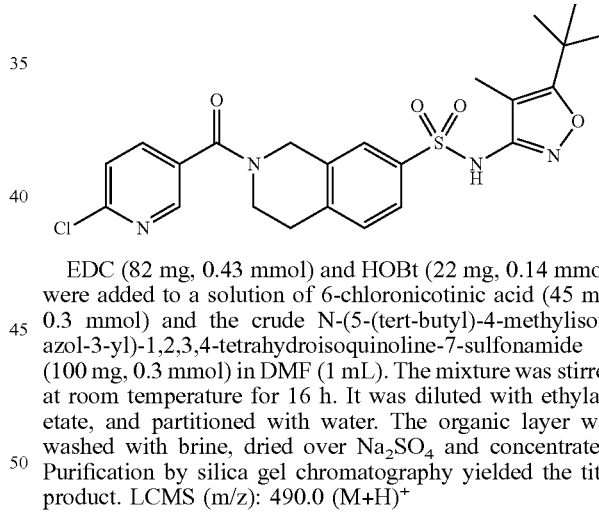

EDC (82 mg, 0.43 mmol) and HOBt (22 mg, 0.14 mmol) were added to a solution of 6-chloronicotinic acid (45 mg, 0.3 mmol) and the crude N-(5-(tert-butyl)-4-methylisoxazol-3-yl)-1,2,3,4-tetrahydroisoquinoline-7-sulfonamide (100 mg, 0.3 mmol) in DMF (1 mL). The mixture was stirred at room temperature for 16 h. It was diluted with ethylacetate, and partitioned with water. The organic layer was washed with brine, dried over Na₂SO₄ and concentrated. Purification by silica gel chromatography yielded the title product. LCMS (m/z): 490.0 (M+H)⁺

Step C: N-(5-(tert-butyl)-4-methylisoxazol-3-yl)-2-(6-(2,2,2-trifluoroethoxy)nicotinoyl)-1,2,3,4-tetrahydroisoquinoline-7-sulfonamide

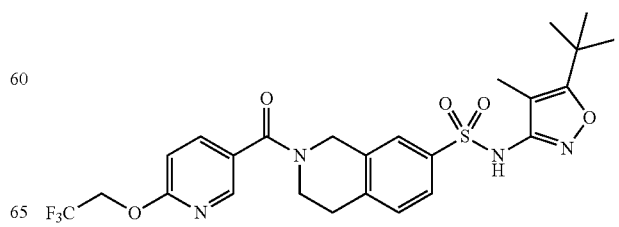

Cesium carbonate (25.9 mg, 0.079 mmol) was added to a mixture of N-(5-(tert-butyl)-4-methylisoxazol-3-yl)-2-(6-chloronicotinoyl)-1,2,3,4-tetrahydroisoquinoline-7-sulfonamide (37 mg, 0.053 mmol) and 2,2,2-trifluoroethanol (7.74 µl, 0.106 mmol) in DMSO (1 ml). The mixture was heated to 100° C. for 60 minutes, then left at room temperature overnight. The reaction mixture was partitioned between EtOAc and water, and the aqueous layer was acidified with 1N NaHSO₄ to pH 5, and extracted with EtOAc. Organic layer was washed with brine, dried over Na₂SO₄ and concentrated. The crude residue was purified by reversed phase HPLC. Appropriate fractions were combined and lyophilized. $^1$H NMR (499 MHz, CHCl₃-d): δ 8.31 (d, 1H), 7.79 (m, 3H), 7.32 (d, 1H), 6.95 (d, 1H), 4.82 (m, 4H), 3.80 (m, 2H), 3.01 (s, 2H), 2.03 (s, 3H), 1.34 (s, 9H). LCMS (m/z): 553.1 (M+H)⁺. MGAT2 Human IC₅₀: 41 nM.

Example 28

Preparation of 7-(N-(5-(tert-butyl)-4-methylisoxazol-3-yl)sulfamoyl)-2-((R)-1-(6-((3,3-difluorocyclobutyl)methoxy)pyridin-3-yl)ethyl)-1,2,3,4-tetrahydroisoquinolin-2-ium 2,2,2-trifluoroacetate

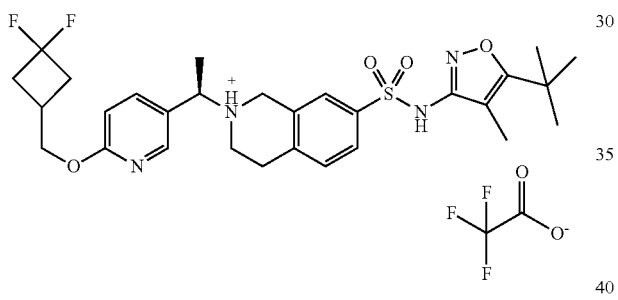

Isoxazole amine (43.9 mg, 0.285 mmol) and dry THF (2189 µl) were added under N₂ to a 40 mL vial containing (R)-2-(1-(6-((3,3-difluorocyclobutyl)methoxy)pyridin-3-yl)ethyl)-1,2,3,4-tetrahydroisoquinoline-7-sulfonyl chloride from Example 26, step G (100 mg, 0.219 mmol). It was cooled to −78° C. Lithium bis(trimethylsilyl)amide (438 µl, 0.438 mmol) (1M in THF) was added to the above solution dropwise, and it was stirred at −78° C. for 5 min, then warmed up slowly to room temperature and stirred for 1 h. The reaction was quenched with saturated NH₄Cl (4 mL). Two layers were separated. The aqueous layer was extracted with EtOAc (20 mL×2). The combined organic layers were dried over MgSO₄, filtered and concentrated. The residue was purified with ISCO, 12 g column, 0-50% EtOAc/hex. A second purification was needed. The product containing fraction was re-dissolved in ACN, and purified with Gilson SunFire™ Prep C18 OBD™ 30×100 mm Column, Part No. 186002572, WATERS, 25-50% ACN/H₂O with 0.1% TFA, 10 min. run, monitored at 220 nm, and collected at 8-10 min. Lyophilization afforded the title compound. $^1$H NMR (600 MHz, CDCl₃) δ 8.19 (s, 1H), 7.84 (t, 2H), 7.74 (s, 1H), 7.32 (d, 1H), 6.91 (d, 1H), 4.54 (q, 1H), 4.36 (d, 2H), 3.23 (br, 3H), 2.73 (m, 2H), 2.65 (m, 1H), 2.44 (m, 2H), 1.96 (s, 3H), 1.84 (d, 3H), 1.33 (s, 9H). LC/MS (m/z): 575 (M+H)⁺. MGAT2 Human IC₅₀: 8.5 nM.

Example 29

Preparation of 7-(N-(5-(tert-butyl)-4-methylisoxazol-3-yl)sulfamoyl)-2-((R)-1-(4-(2,2,2-trifluoroethoxy)phenyl)ethyl)-1,2,3,4-tetrahydroisoquinolin-2-ium 2,2,2-trifluoroacetate

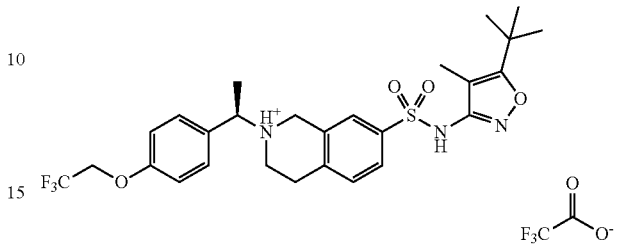

Following the same procedure as described in Example 25, the title compound was prepared from (R)-2-(1-(4-(2,2,2-trifluoroethoxy)phenyl)ethyl)-1,2,3,4-tetrahydroisoquinoline-7-sulfonyl chloride and 5-(tert-butyl)-4-methylisoxazol-3-amine. $^1$H NMR (400 MHz, d₆-DMSO) δ 7.75 (m, 2H), 7.53 (d, 2H), 7.46 (d, 1H), 7.17 (d, 2H), 4.80 (q, 2H), 4.62 (m, 1H), 4.38 (m, 1H), 3.50 (m, 1H), 3.18 (m, 2H), 3.10 (m, 2H), 1.90 (s, 3H), 1.70 (d, 3H), 1.25 (s, 9H). LC/MS (m/z): 552.2 (M+H)⁺. MGAT2 Human IC₅₀: 9.5 nM.

Example 30

Preparation of N-(5-(tert-butyl)-4-methylisoxazol-3-yl)-2-(6-(2-methoxyethoxy)nicotinoyl)-1,2,3,4-tetrahydroisoquinoline-7-sulfonamide

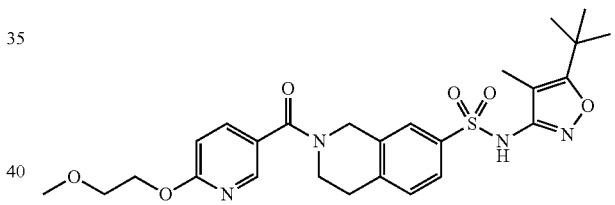

Following the same procedure as described in Step C of Example 27, the title compound was prepared from N-(5-(tert-butyl)-4-methylisoxazol-3-yl)-2-(6-chloronicotinoyl)-1,2,3,4-tetrahydroisoquinoline-7-sulfonamide (Example 27, step B) and 2-methoxyethanol. $^1$H NMR (499 MHz, CHCl₃-d): 8.30 (s, 1H), 7.72-7.78 (m, 2H), 7.31 (m, 2H), 6.87 (d, 1H), 4.90 (br, 2H), 4.54 (t, 2H), 3.77 (t, 2H), 3.45 (s, 3H), 2.99 (s, 2H), 2.02 (s, 3H), 1.60 (m, 2H), 1.26 (s, 9H). LCMS (m/z): 529.15 (M+H)⁺. MGAT2 Human IC₅₀: 31 nM.

Example 31

7-(N-(5-(tert-butyl)isoxazol-3-yl)sulfamoyl)-2-((R)-1-(6-(2-methoxyethoxy)pyridin-3-yl)ethyl)-1,2,3,4-tetrahydroisoquinolin-2-ium 2,2,2-trifluoroacetate

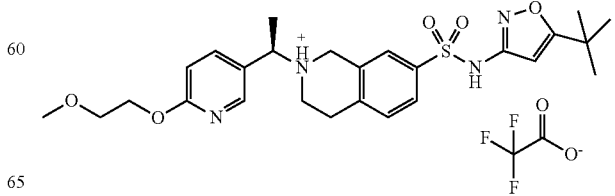

Step A:
1-(6-(2-methoxyethoxy)pyridin-3-yl)ethanone

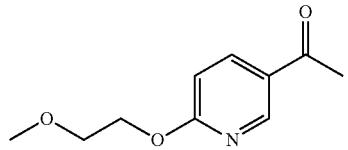

In a flame-dried 250 mL round bottom flask, 1-(6-chloro-3-pyridinyl)-1-ethanone (3 g, 17.35 mmol) was dissolved in anhydrous DMF (32.4 ml). 2-methoxyethanol (2.053 ml, 26.0 mmol) was added to the above mixture at 0° C., under $N_2$, followed with the addition of sodium hydride (1.041 g, 26.0 mmol) portionwise. The mixture was stirred at 0° C. for 10 min. then at room temperature for 1 h. LC/MS showed the starting material was completely consumed. The mixture was quenched with sat. $NH_4Cl$, extracted with EtOAc, dried over $MgSO_4$, and concentrated under reduced pressure. The crude material was purified with ISCO flash column, 40 g column, EtOAc/hexane to afford the title compound. $R_f$=0.39 (50% EtOAc/hex.) LC/MS (m/z): 196 (M+H)$^+$.

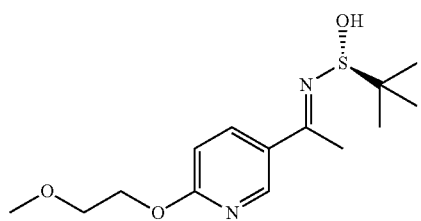

Step B

In a 250 mL round bottom flask containing 1-(6-(2-methoxyethoxy)pyridin-3-yl)ethanone (2.4838 g, 12.72 mmol) and (S)-(−)-2-methyl-2-propanesulfinamide (2.005 g, 16.54 mmol) was charged with THF (57.6 ml). Titanium (IV) ethoxide (5.28 ml, 25.4 mmol) was added under nitrogen. The mixture was heated at 60° C. for 2 h. LC/MS showed about 40% conversion. 1.0 g of (S)-(−)-2-methyl-2-propanesulfinamide was added to the reaction mixture and it was heated at 60° C. for another hour. Then 3 mL of Ti(OEt)$_4$ were added to the mixture and it was heated 60° C. for 1 hour. The reaction was cooled to room temperature and concentrated under reduced pressure. The residue was purified with ISCO, 80 g column, dry load, 0-50% EtOAc/hexane to afford the title compound. $R_f$=0.13 (50% EtOAc/hex.) LC/MS (m/z): 299 (M+H)$^+$.

Step C

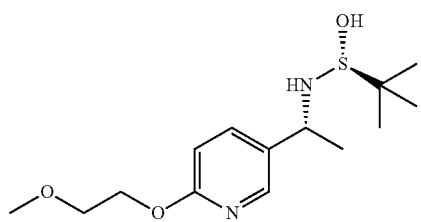

Lithium tri-sec-butylboroydride (12.86 ml, 12.86 mmol) was added dropwise to a solution of the material of Step B (2.34 g, 7.84 mmol) in THF (25.7 ml) and cooled to 0° C. It was warmed to room temperature with stirring over a period of 15 min. TLC and LC/MS showed the completion of the reaction. The mixture was concentrated and purified with ISCO, 80 g column, dry load, 0-4% MeOH/CH$_2$Cl$_2$. The product-containing fractions were purified again with prep. TLC plate (5% MeOH/CH$_2$Cl$_2$) to afford the title compound. $R_f$=0.32 (5% MeOH/CH$_2$Cl$_2$) LC/MS (m/z): 301 (M+H)$^+$.

Step D: (R)-1-(6-(2-methoxyethoxy)pyridin-3-yl)ethanamine

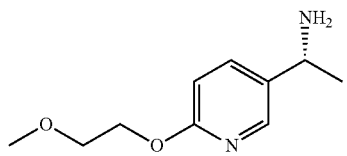

The material of Step C (2.08 g, 6.92 mmol) was treated with 4M HCl in dioxane (17.95 mL) and stirred at room temperature. Solvents were removed in vacuo to afford the title compound. $R_f$=0.13 (1% NEt$_3$ in 10% MeOH/CH$_2$Cl$_2$) LC/MS (m/z): 197 (M+H)$^+$.

Step E: (R)-7-bromo-2-(1-(6-(2-methoxyethoxy)pyridin-3-yl)ethyl)-1,2,3,4-tetrahydroisoquinoline

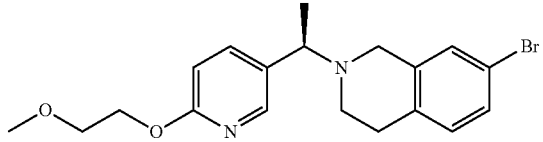 [SMILES: COCCOc1ccc([C@@H](C)N2CCc3ccc(Br)cc3C2)cn1]

To a suspension of (R)-1-(6-(2-methoxyethoxy)pyridin-3-yl)ethanamine (1.54 g, 6.64 mmol) in EtOH (44.2 ml), DIPEA (5.80 ml, 33.2 mmol) was added at room temperature and it turned clear. To the solution, 4-bromo-1-(2-bromoethyl)-2-(bromomethyl)benzene (2.369 g, 6.64 mmol) was added in one portion and stirred at 80° C. for 3 h. The reaction was cooled to room temperature, and concentrated under reduced pressure. The residue was partitioned between ethyl acetate and water. The organic layer was washed with brine, dried over sodium sulfate, filtered and concentrated. The residue was purified with ISCO flash column, 125 g column, 0-30% EtOAc/hexane to afford the title compound. $R_f$=0.12 (30% EtOAc/hex.) LC/MS (m/z): 391 (M+H)$^+$.

Step F: (R)-7-(benzylthio)-2-(1-(6-(2-methoxyethoxy)pyridin-3-yl)ethyl)-1,2,3,4-tetrahydroisoquinoline

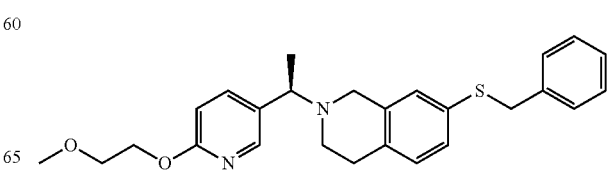

DIPEA (1.651 ml, 9.46 mmol) was added to a solution of (R)-7-bromo-2-(1-(6-(2-methoxyethoxy)pyridin-3-yl)ethyl)-1,2,3,4-tetrahydroisoquinoline (1.85 g, 4.73 mmol) in 1,4-Dioxane (21.11 ml). The mixture was evacuated and backfilled with N₂ (3×). tris(dibenzylideneacetone)dipalladium(0) (0.108 g, 0.118 mmol), 4,5-bis(diphenylphosphino)-9,9-dimethylxanthene (0.191 g, 0.331 mmol) and benzyl mercatane (0.559 ml, 4.73 mmol) were added subsequently and the mixture was degassed twice. The mixture was heated to reflux for 1.5 h. LC/MS showed the starting material was consumed. The mixture was filtered, washed with EtOAc, and concentrated under reduced pressure. The crude material was purified with ISCO, 40 g column, (0-20%-30% EtOAc/hex.) to afford the title compound. LC/MS (m/z): 435 (M+H)⁺.

Step G: (R)-2-(1-(6-(2-methoxyethoxy)pyridin-3-yl)ethyl)-1,2,3,4-tetrahydroisoquinoline-7-sulfonyl Chloride

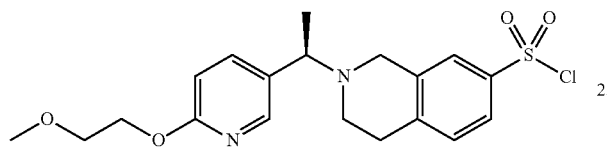

Acetic acid (0.527 ml, 9.20 mmol), water (0.166 ml, 9.20 mmol) and sulfuryl chloride (0.748 ml, 9.20 mmol) were added to a solution of (R)-7-(benzylthio)-2-(1-(6-(2-methoxyethoxy)pyridin-3-yl)ethyl)-1,2,3,4-tetrahydroisoquinoline (1 g, 2.301 mmol) in CH₂Cl₂ (19.67 ml) at room temperature under N₂. It was stirred at room temperature for 4 h. Then additional sulfuryl chloride (0.748 ml, 9.20 mmol) was added to the reaction mixture and it was stirred at room temperature over night. The mixture was partitioned between CH₂Cl₂ and saturated NaHCO₃. The organic phase was separated, dried over MgSO₄, and concentrated to afford the title compound. The crude material was used for the next step without further purification. LC/MS (m/z): 411 (M+H)⁺.

Step H: 7-(N-(5-(tert-butyl)isoxazol-3-yl)sulfamoyl)-2-((R)-1-(6-(2-methoxyethoxy)pyridin-3-yl)ethyl)-1,2,3,4-tetrahydroisoquinolin-2-ium 2,2,2-trifluoroacetate

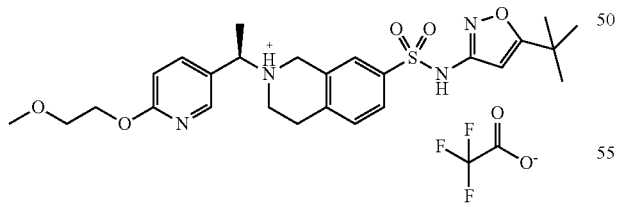

3-amino-5-t-butylisoxazole (44.3 mg, 0.316 mmol) and dry THF (2434 µl) were added, under N₂, to a 40 mL vial containing (R)-2-(1-(6-(2-methoxyethoxy)pyridin-3-yl)ethyl)-1,2,3,4-tetrahydroisoquinoline-7-sulfonyl chloride (100 mg, 0.243 mmol). It was cooled to −78° C. Lithium bis(trimethylsilyl)amide (292 µl, 0.292 mmol) (1M in THF) was added to the above solution dropwise, and it was stirred at −78° C. for 5 min. then warmed up slowly to room temperature and stirred for 1 h. The reaction was quenched with saturated NH₄Cl (5 mL). The two layers were separated. The aqueous layer was extracted with EtOAc (20 mL×2). The combined organic layers were dried over MgSO₄, filtered and concentrated. The residue was purified with prep. TLC plate, 4% MeOH/CH₂Cl₂. Then it was purified with Gilson SunFire™ Prep C18 OBD™ 30×100 mm Column, Part No. 186002572, WATERS, 5-60% ACN/H₂O with 0.1% TFA, 10 min. run, monitored at 220 nm, and collected at 7-11 min. Lyophilization afforded the title compound. ¹H NMR (600 MHz, CDCl₃) δ 8.07 (s, 1H), 7.86 (s, 1H), 7.76 (d, 1H), 7.67 (d, 1H), 7.59 (s, 1H), 7.23 (d, 1H), 6.83 (d, 1H), 4.43 (q, 1H), 4.41 (t, 2H), 4.23 (br, 1H), 3.68 (t, 2H), 3.38 (s, 3H), 3.31 (m, 4H), 3.15 (br, 1H), 1.74 (d, 3H), 1.19 (s, 3H). LC/MS (m/z): 515 (M+H)⁺. MGAT2 Human IC₅₀: 17.2 nM.

Example 32

Preparation of 7-(N-(5-(tert-butyl)-4-(hydroxymethyl)isoxazol-3-yl)sulfamoyl)-2-((R)-1-(6-(2,2,2-trifluoroethoxy)pyridin-3-yl)ethyl)-1,2,3,4-tetrahydroisoquinolin-2-ium 2,2,2-trifluoroacetate

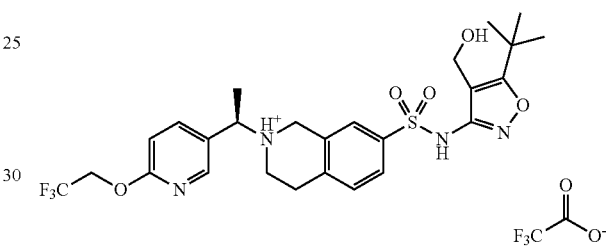

Pyridine (0.8 mL) was added to Intermediate 3 (50 mg, 0.115 mmol) and (3-amino-5-(tert-butyl)isoxazol-4-yl)methanol (60 mg, 0.353 mmol) and the reaction stirred overnight at room temperature. The solvent was removed in vacuo and the product isolated by HPLC purification to give the title compound. ¹H NMR (400 MHz, d₆-DMSO) δ 8.35 (m, 1H), 7.99 (m, 1H), 7.75 (m, 2H), 7.45 (d, 1H), 7.11 (d, 1H), 5.01 (q, 2H), 4.80 (m, 2H), 4.31 (s, 2H), 3.60 (m, 1H), 3.20 (m, 4H), 1.70 (m, 3H), 1.29 (s, 9H). LC/MS (m/z): 569.2 (M+H)⁺. MGAT2 Human IC₅₀: 19.8 nM.

Example 33

Preparation of (R)-ethyl 5-(tert-butyl)-3-(2-(1-(3,5-difluorophenyl)ethyl)-1,2,3,4-tetrahydroisoquinoline-7-sulfonamido)isoxazole-4-carboxylate

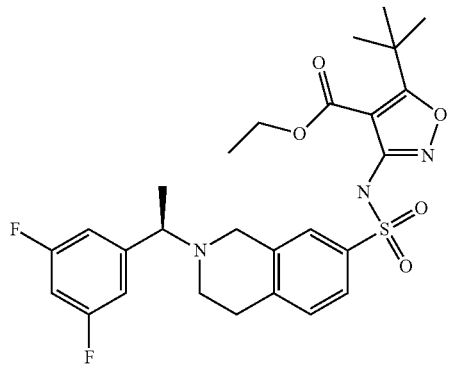 [SMILES: CCOC(=O)c1c(NS(=O)(=O)c2ccc3c(c2)CN([C@H](C)c2cc(F)cc(F)c2)CC3)noc1C(C)(C)C]

Step A: tert-Butyl (5-(tert-butyl)isoxazol-3-yl)carbamate

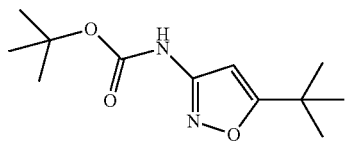 [SMILES: CC(C)(C)OC(=O)Nc1cc(C(C)(C)C)on1]

A mixture of 3-amino-5-tert-butylisoxazole (2.00 g, 14.27 mmol), DMAP (0.174 g, 1.427 mmol) and di-tert-butyl dicarbonate (3.64 ml, 15.69 mmol) in DCM (20 ml) was stirred at room temperature for 30 min. The reaction mixture was concentrated and purified by BIOTAGE (40M, 0-20% ethyl acetate) to give the title compound.

Step B: Ethyl 3-((tert-butoxycarbonyl)amino)-5-(tert-butyl)isoxazole-4-carboxylate

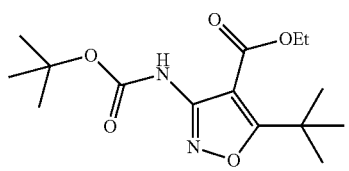 [SMILES: CCOC(=O)c1c(NC(=O)OC(C)(C)C)noc1C(C)(C)C]

A solution of tert-butyl (5-(tert-butyl)isoxazol-3-yl)carbamate (2.9 g, 12.07 mmol) in THF (100 ml) was cooled to −78° C. and n-butyllithium (2.4 M in hexane, 11.10 ml, 27.8 mmol) was added. It was stirred for 10 min and warmed to room temperature stirring for 20 min. The reaction was cooled to −78° C. and ethyl chloroformate (1.265 ml, 13.28 mmol) was added in one portion. It was stirred for 10 min and warmed to 0° C. for 20 min. The reaction was quenched with saturated aqueous ammonium chloride, and extracted with ethyl acetate. The organic layer was dried over sodium sulfate, filtered and concentrated under reduced pressure. The residue was purified by BIOTAGE (40M, 0-40% ethyl acetate in hexane) to give the title compound.

Step C: Ethyl 3-amino-5-(tert-butyl)isoxazole-4-carboxylate

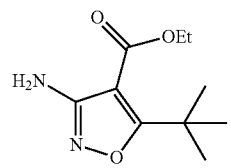

TFA (10 ml, 130 mmol) was added to a solution of ethyl 3-((tert-butoxycarbonyl)amino)-5-(tert-butyl)isoxazole-4-carboxylate (3.7 g, 11.85 mmol) in DCM (30 ml). The mixture was stirred for 1 h at room temperature. It was concentrated under reduced pressure. The residue was dissolved in ethyl acetate and washed with saturated sodium bicarbonate and brine. The organic layer was separated and dried over sodium sulfate, filtered and concentrated under reduced pressure. The residue was purified by BIOTAGE (40 M, 0-20% ethyl acetate in hexane with 1% triethylamine) to give the title compound. LC/MS (m/z): 213 (M+H)$^+$.

Step D: (R)-ethyl 5-(tert-butyl)-3-(2-(1-(3,5-difluorophenyl)ethyl)-1,2,3,4-tetrahydroisoquinoline-7-sulfonamido)isoxazole-4-carboxylate

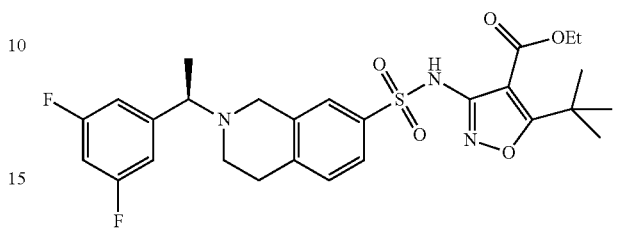

A mixture of ethyl 3-amino-5-(tert-butyl)isoxazole-4-carboxylate (114 mg, 0.538 mmol) and Intermediate 5 (200 mg, 0.538 mmol) in pyridine (2 mL) were stirred at room temperature overnight. It was concentrated and purified by Prep-TLC (1000 um, 25% ethyl acetate in hexane) to give the title compound. $^1$H NMR (500 MHz, CDCl$_3$) δ 8.88 (s, 1H), 7.90 (d, 1H), 7.80 (s, 1H), 6.98 (bs, 1H), 6.76 (bs, 1H), 4.41 (q, 2H), 3.90 (m, 1H), 3.60 (m, 3H), 2.6-3.0 (m, 4H), 1.40 (m, 15H); LC/MS (m/z): 548 (M+H)$^+$. MGAT2 Human IC$_{50}$: 3.7 nM.

Example 34

Preparation of (R)-5-(tert-butyl)-3-(2-(1-(3,5-difluorophenyl)ethyl)-1,2,3,4-tetrahydroisoquinoline-7-sulfonamido)-N-methylisoxazole-4-carboxamide

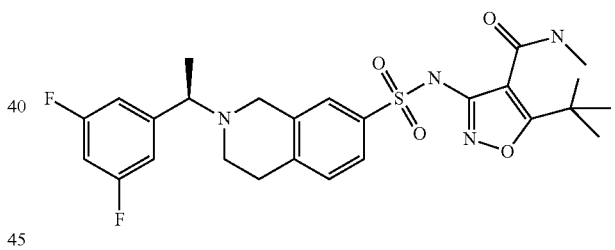

The compound of Example 33 (10 mg, 0.018 mmol) and methylamine (2 M, 0.5 mL, 1 mmol) in THF (0.5 mL) were heated at 80° C. overnight. It was concentrated and diluted with acetonitrile, water, and a few drops of formic acid and then purified by HPLC to give the title compound. LC/MS (m/z): 533 (M+H)$^+$. MGAT2 Human IC$_{50}$: 6.2 nM.

Example 35

Preparation of N-(5-(tert-butyl)-4-propylisoxazol-3-yl)-2-(((6-ethylpyridin-3-yl)methyl)-1,2,3,4-tetrahydroisoquinoline-7-sulfonamide

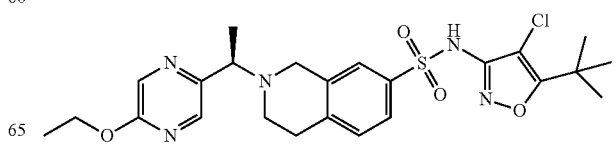

Step A:
5-Chloro-N-methoxy-N-methylpyrazine-2-carboxamide

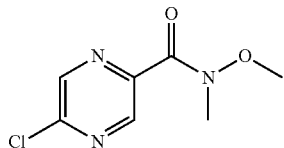

DMF (0.2 mL) was added to the mixture of 5-chloropyrazine-2-carboxylic acid (5 g, 31.5 mmol) in thionyl chloride (30 mL). The mixture was heated to reflux at 85° C. under nitrogen for 3 h. The mixture was evaporated under reduced pressure and dissolved in DCM (100 mL) followed by addition of N, O-dimethylhydroxylamine hydrochloride (4.61 g, 47.3 mmol). The reaction was stirred at 0° C. for 5 min and TEA was added dropwise. Then reaction mixture was warmed to room temperature and stirred overnight. It was diluted with DCM, and the solid (TEA-HCl salt) was filtered off. The solution was, washed with saturated NaHCO$_3$, water and brine in sequence. The organic solution was dried over MgSO$_4$, filtered and concentrated. The crude material was purified by MPLC (0-50% EA: Hex) to afford of the title compound.

Step B: 1-(5-Chloropyrazin-2-yl)ethanone

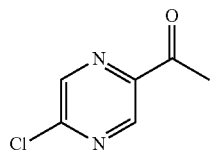

Methylmagnesium bromide (11.5 ml, 34.5 mmol) was added dropwise to a solution of 5-Chloro-N-methoxy-N-methylpyrazine-2-carboxamide (5.8 g, 28.8 mmol) in THF (50 ml) at −10° C. After addition the reaction flask was removed from the cold bath and allowed to warm to room temperature. After it was stirred for 1 h, the reaction was quenched with water and extracted with EtOAc. The organic layer was washed with brine, dried over MgSO$_4$, filtered and concentrated. The residue was purified by column chromatography (0-30% EtOAc/hexanes, RediSep-80 gram) to give the title compound as a white solid.

Step C: 1-(5-Ethoxypyrazin-2-yl)ethanone

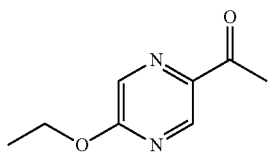

A solution of 1-(5-chloropyrazin-2-yl)ethanone in ethanol (25 mL) was added to a solution of sodium ethoxide in ethanol at 0° C. The reaction mixture turned into a yellowish brown slurry. After it was stirred at 0° C. for 1 h, the reaction was quenched with saturated aqueous NH$_4$Cl. The mixture was extracted with EtOAc. The organic layer was washed with brine, dried over Na$_2$SO$_4$, filtered and concentrated in vacuo. The residue was purified by column chromatography (0-30% EtOAc/hexanes) to give the title compound.

Step D: (R)-1-(5-Ethoxypyrazin-2-yl)ethanamine

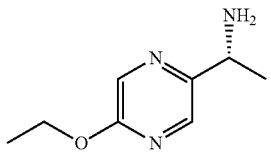

Following the procedure described in Step B of Example 22 and employing 1-(5-ethoxypyrazin-2-yl)ethanone, the chiral amine, (R)-1-(5-ethoxypyrazin-2-yl)ethanamine, was prepared.

Step E: (R)-7-Bromo-2-(1-(5-ethoxypyrazin-2-yl)ethyl)-1,2,3,4-tetrahydroisoquinoline

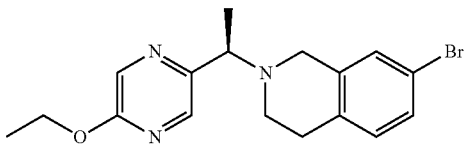 [SMILES: CCOc1cnc([C@@H](C)N2CCc3ccc(Br)cc3C2)cn1]

A solution of (R)-1-(5-ethoxypyrazin-2-yl)ethanamine (2.03 g, 9.22 mmol), 4-bromo-1-(2-bromoethyl)-2-(bromomethyl)benzene (3.49 g, 9.77 mmol) and potassium carbonate (3.82 g, 27.7 mmol) in ethanol (40.6 ml) was refluxed for 3 h under nitrogen. The reaction was cooled to room temperature and the mixture was filtered. The filtrate was concentrated and diluted with ethyl acetate. The solution was washed with water. The aqueous layer was extracted with EtOAc and the combined organic layers were dried over MgSO$_4$, filtered and concentrated under reduced pressure. The crude oil was purified by MPLC (0-20% EtOAc/hexane) to give the title compound. LC/MS (m/z): 363 (M+H)$^+$.

Step F: (R)-7-(Benzylthio)-2-(1-(5-ethoxypyrazin-2-yl)ethyl)-1,2,3,4-tetrahydroisoquinoline

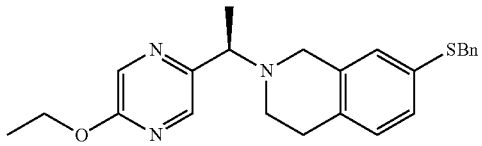

(R)-7-Bromo-2-(1-(5-ethoxypyrazin-2-yl)ethyl)-1,2,3,4-tetrahydroisoquinoline (2.7 g, 7.45 mmol), Pd$_2$(dba)$_3$ (68 mg, 0.074 mmol) and Xantphos (86 mg, 0.149 mmol) in dioxane (20 ml) was bubbled with nitrogen for 20 min. Then DIEA (2.73 ml, 15.65 mmol) and benzyl thiol (0.97 ml, 8.20 mmol) were added. The reaction mixture was heated at 110° C. for 2 h. It was cooled to room temperature, diluted with ethyl acetate and washed with water and brine in sequence.

The organic layer was dried over sodium sulfate and concentrated. The residue was purified by BIOTAGE (40 M, 0-100% ethyl acetate in hexane) to give the title compound. LC/MS (m/z): 406 (M+H)+.

Step G: (R)-2-(1-(5-Ethoxypyrazin-2-yl)ethyl)-1,2,3,4-tetrahydroisoquinoline-7-sulfonyl Chloride

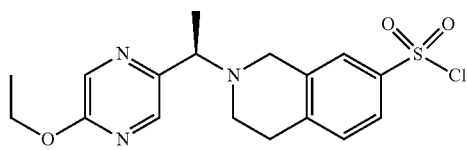 [SMILES: CCOc1cnc([C@@H](C)N2CCc3ccc(S(=O)(=O)Cl)cc3C2)cn1]

Acetic acid (1.5 ml, 26.6 mmol) and water (0.48 ml, 26.6 mmol) were added to a solution of (R)-7-(benzylthio)-2-(1-(5-ethoxypyrazin-2-yl)ethyl)-1,2,3,4-tetrahydroisoquinoline (2.7 g, 6.66 mmol) in DCM (10 ml). The mixture was cooled in an ice-water-bath for 5 min, then sulfuryl chloride (2.2 ml, 26.6 mmol) was added dropwise. The ice bath was removed and the mixture was stirred at room temperature for 3 h. The DCM layer was decanted. To the sticky mass was added saturated aqueous NaHCO₃ and ethyl acetate. After the layers were separated, the aqueous layer was extracted with ethyl acetate and the combined organic layers were washed with brine and dried over Na₂SO₄, filtered and concentrated under reduced pressure to obtain the title compound.

Step H: (R)—N-(5-(tert-Butyl)-4-chloroisoxazol-3-yl)-2-(1-(5-ethoxypyrazin-2-yl)ethyl)-1,2,3,4-tetrahydroisoquinoline-7-sulfonamide

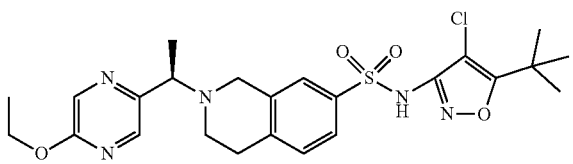 [SMILES: CCOc1cnc([C@@H](C)N2CCc3ccc(S(=O)(=O)Nc4noc(C(C)(C)C)c4Cl)cc3C2)cn1]

LHMDS (0.74 ml, 0.74 mmol) was added dropwise at −78° C. with magnetic stirring under nitrogen to a solution of (R)-2-(1-(5-ethoxypyrazin-2-yl)ethyl)-1,2,3,4-tetrahydroisoquinoline-7-sulfonyl chloride (112 mg, 0.295 mmol) and 5-(tert-butyl)-4-chloroisoxazol-3-amine (64 mg, 0.368 mmol) in THF (1 ml). The reaction mixture was stirred for 1 h and was allowed to warm to room temperature for 1 h. The reaction was quenched with ammonium chloride and extracted with ethyl acetate. The organic layer was washed with brine, dried over sodium sulfate, filtered and concentrated in vacuo. The residue was purified by HPLC to give the title compound. LC/MS (m/z): 520 (M+H)+. MGAT2 Human IC$_{50}$: 8.3 nM.

Example 36

Preparation of (R)—N-(5-(tert-butyl)-4-methylisoxazol-3-yl)-2-(1-(5-ethoxypyrazin-2-yl)ethyl)-1,2,3,4-tetrahydroisoquinoline-7-sulfonamide

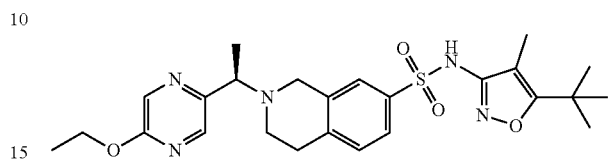

LHMDS (0.74 ml, 0.74 mmol) was added dropwise at −78° C. with magnetic stirring under nitrogen to a solution of (R)-2-(1-(5-ethoxypyrazin-2-yl)ethyl)-1,2,3,4-tetrahydroisoquinoline-7-sulfonyl chloride (from Step G of Example 35; 112 mg, 0.295 mmol) and 5-(tert-butyl)-4-methylisoxazol-3-amine (57 mg, 0.368 mmol) in THF (1 mL). The reaction mixture was stirred for 1 h and was allowed to warm to room temperature for 1 h. Then the reaction was quenched with ammonium chloride and extracted with ethyl acetate. The organic layer was washed with brine, dried over sodium sulfate, filtered and concentrated in vacuo. The residue was purified by HPLC to give the title compound. LC/MS (m/z): 500 (M+H)+. MGAT2 Human IC$_{50}$: 3.5 nM.

Example 37

Preparation of (R)—N-(5-(tert-butyl)-4-methylisoxazol-3-yl)-2-(1-(5-ethoxypyrazin-2-yl)ethyl)-1,2,3,4-tetrahydroisoquinoline-7-sulfonamide

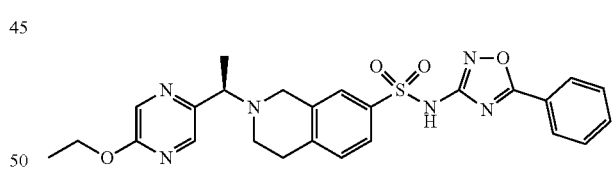

LHMDS (0.74 ml, 0.74 mmol) was added dropwise at −78° C. with magnetic stirring under nitrogen to a solution of (R)-2-(1-(5-ethoxypyrazin-2-yl)ethyl)-1,2,3,4-tetrahydroisoquinoline-7-sulfonyl chloride from Step G of Example 35 (112 mg, 0.295 mmol) and 5-phenyl-1,2,4-oxadiazol-3-amine (57 mg, 0.368 mmol) in THF (1 mL). The reaction mixture was stirred for 1 h and was allowed to warm to room temperature for 1 h. It was quenched with ammonium chloride and extracted with ethyl acetate. The organic layer was washed with brine, dried over sodium sulfate, filtered and concentrated in vacuo. The residue was purified by HPLC to give the title compound. LC/MS (m/z): 507 (M+H)+. MGAT2 Human IC$_{50}$: 11.5 nM.

Example 38

Preparation of (R)-2-(1-(3,5-difluorophenyl)ethyl)-N-(5-propylpyrazin-2-yl)-1,2,3,4-tetrahydroisoquinoline-7-sulfonamide

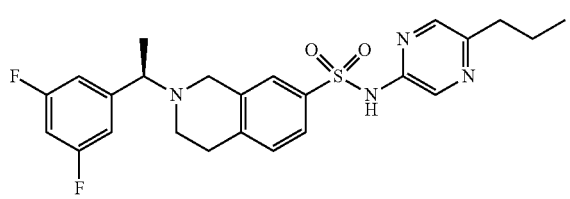 [SMILES: CCCc1cnc(NS(=O)(=O)c2ccc3c(c2)CN([C@H](C)c2cc(F)cc(F)c2)CC3)cn1]

Step A: (R,E)-2-(1-(3,5-difluorophenyl)ethyl)-N-(5-(prop-1-en-1-yl)pyrazin-2-yl)-1,2,3,4-tetrahydroisoquinoline-7-sulfonamide

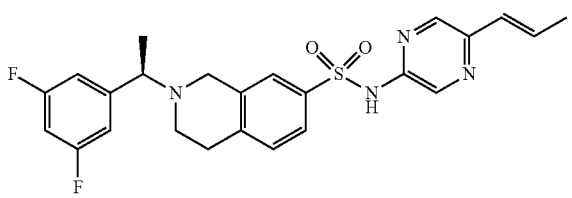 [SMILES: C/C=C/c1cnc(NS(=O)(=O)c2ccc3c(c2)CN([C@H](C)c2cc(F)cc(F)c2)CC3)cn1]

LHMDS (2.353 ml, 2.353 mmol) was added to a stirred solution of (E)-5-(prop-1-en-1-yl)pyrazin-2-amine (0.127 g, 0.941 mmol) in THF (5 mL) that had been cooled to −78° C. under an atmosphere of nitrogen. After 30 min Intermediate 5 (0.350 g, 0.941 mmol) was added to the resultant cooled mixture. This solution was allowed to warm to room temperature with continued stirring overnight. The volatiles were removed under reduced pressure and the resultant residue was diluted with water. The aqueous phase was extracted with EtOAc×3. The combined organic layers were dried over MgSO$_4$, filtered and concentrated under reduced pressure. The resultant residue was purified by reverse phase HPLC (XTERRA, C18, 19×100 mm, gradient elution, 10-100% acetonitrile/water with 0.1% TFA) to yield the title compound. LC/MS (m/z): 471.1 (M+H)$^+$.

Step B: Preparation of (R)-2-(1-(3,5-difluorophenyl)ethyl)-N-(5-propylpyrazin-2-yl)-1,2,3,4-tetrahydroisoquinoline-7-sulfonamide

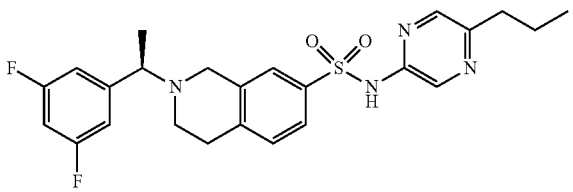 [SMILES: CCCc1cnc(NS(=O)(=O)c2ccc3c(c2)CN([C@H](C)c2cc(F)cc(F)c2)CC3)cn1]

A catalytic amount of Pd/C (0.0028 g, 0.026 mmol) was added to a stirred solution of (R,E)-2-(1-(3,5-difluorophenyl)ethyl)-N-(5-(prop-1-en-1-yl)pyrazin-2-yl)-1,2,3,4-tetrahydroisoquinoline-7-sulfonamide (0.124 g, 0.264 mmol) in MeOH (5 mL), and the resultant solution was degassed with N$_2$ and evacuated. A balloon atmosphere of H$_2$ was applied and the resultant mixture was stirred for 3 h. The solution was filtered over a pad of CELITE, washing with DCM and MeOH. The filtrate was concentrated under reduced pressure and the resultant residue was purified by reverse phase HPLC (XTERRA, C18, 19×100 mm, gradient elution, 10-100% acetonitrile/water with 0.1% TFA) to yield the title compound. $^1$H NMR (500 MHz, CD$_3$OD) δ 8.33 (s, 1H), 8.06 (s, 1H), 7.69 (d, 1H), 7.64 (s, 1H), 7.28 (d, 1H), 7.05 (d, 2H), 6.95-6.75 (m, 1H), 3.86-3.58 (m, 3H), 2.90-2.65 (m, 6H), 1.68-1.67 (m, 2H), 1.45 (d, 3H), 0.92 (t, 3H). LC/MS (m/z): 473.0 (M+H)$^+$. MGAT2 Human IC$_{50}$: 6 nM.

Example 39

Preparation of N-(5-(tert-butyl)-4-propylisoxazol-3-yl)-2-((6-ethylpyridin-3-yl)methyl)-1,2,3,4-tetrahydroisoquinoline-7-sulfonamide

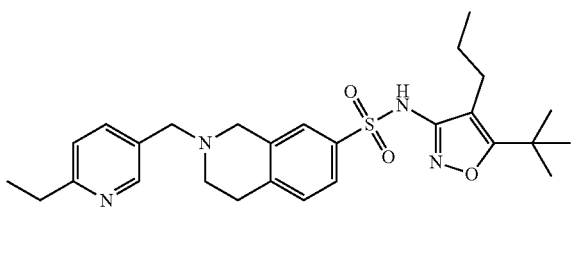 [SMILES: CCCc1c(NS(=O)(=O)c2ccc3c(c2)CN(Cc2ccc(CC)nc2)CC3)noc1C(C)(C)C]

Step A: 6-Chloro-N-methoxy-N-methylnicotinamide

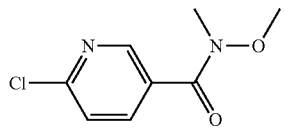

A mixture of N,O-dimethylhydroxylamine hydrochloride (3.13 g, 32.1 mmol) (dried by azetropical distillation with toluene under vacuum) and methyl 6-chloronicotinate (5 g, 29.1 mmol) in THF (100 ml) was cooled in an ice-acetone bath. To the suspension was added isopropylmagnesium chloride (40 ml, 80 mmol) over 5 min. The mixture was stirred for 2 h. It was quenched with 1 N HCl (10 mL) and saturated aqueous KH$_2$PO$_4$ and extracted with ethyl acetate three times. The combined organic layers were washed with brine, dried over sodium sulfate, filtrated, and concentrated in vacuo. The residue was purified by silica gel (BIOTAGE 40M, 0-80% ethyl acetate in hexane) to afford the title compound.

Step B: N-methoxy-N-methyl-6-vinylnicotinamide

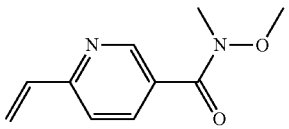

A flask with a refluxing condenser was charged with [1,1'-bis(diphenylphosphino)-ferrocene]dichloropalladium (II) (0.940 g, 1.234 mmol), 6-chloro-N-methoxy-N-methyl-nicotinamide (4.95 g, 24.67 mmol), potassium vinyltrifluoroborate (3.97 g, 29.6 mmol), TEA (5.16 ml, 37.0 mmol) and EtOH (50 ml). The reaction was purged with nitrogen and heated to reflux for 2 h. The reaction mixture was cooled to room temperature and filtered. The solution was concentrated and purified by silica gel (BIOTAGE flash 40M, 0-80% ethyl acetate in hexane) to afford the title compound. $^1$H NMR (500 MHz, CDCl$_3$) δ 8.95 (d, 1H), 8.04 (dd, 1H), 7.40 (d, 1H), 6.86 (dd, 1H), 6.34 (d, 1H), 5.60 (d, 1H), 3.59 (s, 3H), 3.41 (s, 3H); LC/MS (m/z): 193 (M+H)$^+$.

Step C: 6-Ethyl-N-methoxy-N-methylnicotinamide

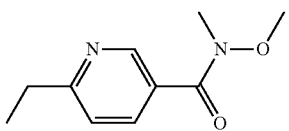

N-Methoxy-N-methyl-6-vinylnicotinamide (2 g, 10.41 mmol) and 10% (w/w) palladium on carbon (0.554 g, 0.520 mmol) in MeOH (30 ml) was shaken under hydrogen (1 atm) for 2 h at room temperature. TLC showed the completion of the reaction. The reaction mixture was filtrated through CELITE and concentrated to give the title compound. LC/MS (m/z): 213 (M+H)$^+$.

Step D: 6-ethylnicotinaldehyde

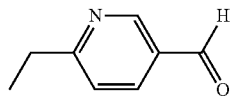

DIBAL-H (11.33 ml, 11.33 mmol) was added dropwise to a solution of 6-ethyl-N-methoxy-N-methylnicotinamide (2 g, 10.30 mmol) in toluene (40 ml) and cooled in a dry-ice-acetone bath. After stirring for 30 min, TLC showed no starting material left. The reaction was quenched by methanol (1 mL) and 1 N HCl (10 mL). The reaction mixture was warmed to room temperature and to which as added saturated aqueous NaHCO$_3$. The mixture was filtered through CELITE and the were separated. The aqueous layer was extracted with ethyl acetate. The combined organic layers were washed with brine and dried over sodium sulfate, filtered and concentrated. The residue was purified by silica gel (BIOTAGE Flash 25M, 0-70% ethyl acetate in hexane) to give the title compound.

Step E: 7-Bromo-2-((6-ethylpyridin-3-yl)methyl)-1,2,3,4-tetrahydroisoquinoline

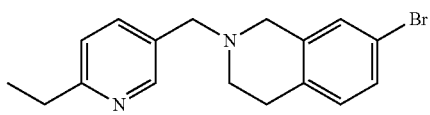 [SMILES: CCc1ccc(CN2CCc3ccc(Br)cc3C2)cn1]

7-bromo-1,2,3,4-tetrahydroisoquinoline (2.354 g, 11.10 mmol) and 4 Å molecular sieves (2 g) were added to a solution of ethylnicotinaldehyde (1 g, 7.40 mmol) in MeOH (15 ml) and acetic acid (5 ml). After it was stirred at room temperature for 1 h, sodium cyanoborohydride (1.395 g, 22.20 mmol) was added to the mixture and stirring continued for 1 h. The reaction was quenched with water, and extracted with ethyl acetate three times. The combined organic layers were washed with brine, dried over sodium sulfate, filtered and concentrated. The residue was purified by BIOTAGE (40 g, 0-100% ethyl acetate in hexane) to give the title compound. $^1$H NMR (500 MHz, CDCl$_3$) δ 8.50 (m, 1H), 7.65 (m, 1H), 7.26 (m, 1H), 7.16 (m, 2H), 6.98 (d, 1H), 3.76 (s, 1H), 3.67 (s, 1H), 3.61 (s, 1H), 3.37 (s, 1H), 2.82-2.90 (m, 4H), 2.75 (t, 1H), 2.65 (s, 1H), 1.34 (m, 3H); LC/MS (m/z): 332 (M+H)$^+$.

Step F: 7-(Benzylthio)-2-((6-ethylpyridin-3-yl)methyl)-1,2,3,4-tetrahydroisoquinoline

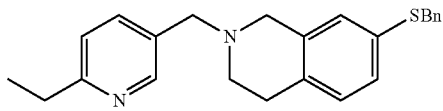

A solution of 7-Bromo-2-((6-ethylpyridin-3-yl)methyl)-1,2,3,4-tetrahydroisoquinoline (900 mg, 2.72 mmol), Pd$_2$(dba)$_3$ (62.2 mg, 0.068 mmol) and Xantphos (118 mg, 0.204 mmol) in dioxane (20 ml) was bubbled nitrogen through for 20 min. TEA (0.946 ml, 5.43 mmol) and benzylthiol (0.351 ml, 2.99 mmol) were added. The reaction mixture was heated at 102° C. for 3 h. After it was cooled to room temperature, the reaction was diluted with ethyl acetate and washed with water and brine in sequence. The organic layer was dried over sodium sulfate and concentrated. The residue was purified by BIOTAGE (40 M, 0-100% ethyl acetate in hexane) to give the title compound. LC/MS (m/z): 375 (M+H)$^+$.

Step G: 7-(Chlorosulfonyl)-2-((6-ethylpyridin-3-yl)methyl)-1,2,3,4-tetrahydroisoquinolin-2-ium Chloride

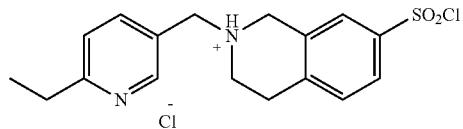

Acetic acid (0.44 ml, 7.69 mmol) and water (0.14 ml, 7.77 mmol) were added to a solution of 7-(benzylthio)-2-((6-ethylpyridin-3-yl)methyl)-1,2,3,4-tetrahydroisoquinoline (710 mg, 1.896 mmol) in DCM (10 ml). The mixture was cooled in an ice-water-bath for 5 min., then sulfuryl chloride (0.62 ml, 7.63 mmol) was added dropwise. The mixture was stirred for 30 min. White solids were precipitated. The bath was removed and the mixture was stirred at room temperature for 1 h. The reaction mixture was concentrated and triturated with diethyl ether. The solids were collected by filtration, dried under reduced pressure and used without further purification.

Step H: N-(5-(tert-butyl)-4-propylisoxazol-3-yl)-2-((6-ethylpyridin-3-yl)methyl)-1,2,3,4-tetrahydroisoquinoline-7-sulfonamide

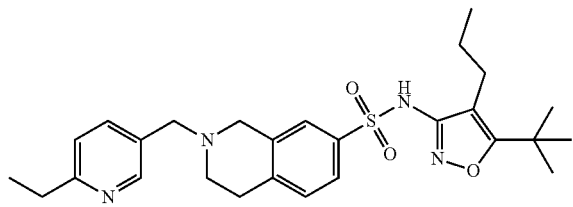 [SMILES: CCCc1c(NS(=O)(=O)c2ccc3c(c2)CN(Cc2ccc(CC)nc2)CC3)noc1C(C)(C)C]

LiHMDS (0.723 ml, 0.723 mmol) was added dropwise at −78° C. with magnetic stirring under nitrogen to a solution of 7-(chlorosulfonyl)-2-((6-ethylpyridin-3-yl)methyl)-1,2,3,4-tetrahydroisoquinolin-2-ium chloride (70 mg, 0.181 mmol) and 5-(tert-butyl)-4-propylisoxazol-3-amine (42.8 mg, 0.235 mmol) in THF (1 ml). The reaction mixture stirred for 1 h and was allowed to warm to room temperature and stirred for 1 h. The reaction was quenched with ammonium chloride and extracted with ethyl acetate. The organic layer was washed with brine, dried over sodium sulfate, filtered and concentrated in vacuo. The residue was purified by TLC (1000 um, ethyl acetate) to give the title compound. $^1$H NMR (500 MHz, CDCl$_3$) δ 8.50 (s, 1H), 7.79 (d, 1H), 7.66 (m, 2H), 7.26 (d, 1H), 7.18 (m, 1H), 3.69 (m, 4H), 2.96 (m, 2H), 2.86 (q, 2H), 2.77 (m, 2H), 2.41 (m, 2H), 1.50 (m, 2H), 1.34 (m, 12H), 0.96 (t, 3H); LC/MS (m/z): 497 (M+H)$^+$. MGAT2 Human IC$_{50}$: 11 nM.

Example 40

Preparation of N-(5-(tert-butyl)-4-ethylisoxazol-3-yl)-2-((6-ethylpyridin-3-yl)methyl)-1,2,3,4-tetrahydroisoquinoline-7-sulfonamide

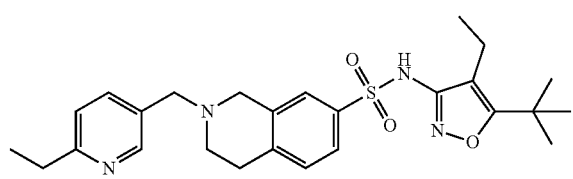 [SMILES: CCc1ccc(CN2CCc3ccc(S(=O)(=O)Nc4noc(C(C)(C)C)c4CC)cc3C2)cn1]

LiHMDS (0.723 ml, 0.723 mmol) was added dropwise at −78° C. with magnetic stirring under nitrogen to a solution of 7-(chlorosulfonyl)-2-((6-ethylpyridin-3-yl)methyl)-1,2,3,4-tetrahydroisoquinolin-2-ium chloride from Example 39, step G (70 mg, 0.181 mmol) and 5-(tert-butyl)-4-ethylisoxazol-3-amine (42.8 mg, 0.235 mmol) in THF (1 ml). The reaction mixture was stirred for 1 h and was allowed to warm to room temperature for 1 h. The reaction was quenched with ammonium chloride and extracted with ethyl acetate. The organic layer was washed with brine, dried over sodium sulfate, filtered and concentrated in vacuo. The residue was purified by reverse phase HPLC to give the title compound. $^1$H NMR (500 MHz, CD3OD) δ 8.76 (s, 1H), 8.25 (d, 1H), 7.87 (d, 1H), 7.82 (s, 1H), 7.72 (d, 1H), 7.47 (d, 1H), 4.56 (s, 2H), 4.49 (s, 2H), 3.61 (m, 2H), 3.31 (m, 2H), 3.00 (q, 2H), 2.51 (q, 2H), 1.39 (t, 3H), 1.33 (s, 9H), 1.09 (t, 3H); LC/MS (m/z): 483 (M+H)$^+$. MGAT2 Human IC$_{50}$: 15 nM.

Example 41

Preparation of N-(4-bromo-5-(tert-butyl)isoxazol-3-yl)-2-((6-propylpyridin-3-yl)methyl)-1,2,3,4-tetrahydroisoquinoline-7-sulfonamide

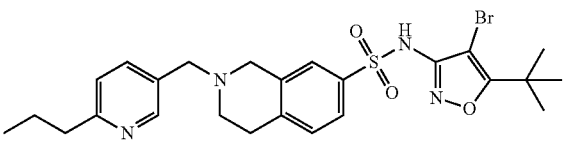 [SMILES: CCCc1ccc(CN2CCc3ccc(S(=O)(=O)Nc4noc(C(C)(C)C)c4Br)cc3C2)cn1]

Step A: (E)-N-Methoxy-N-methyl-6-(prop-1-en-1-yl)nicotinamide

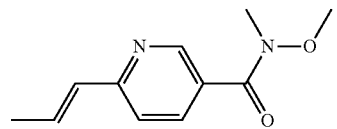

A flask with a refluxing condenser was charged with [1,1′-bis(diphenylphosphino)ferrocene]dichloropalladium (II) (1.519 g, 1.994 mmol), 6-chloro-N-methoxy-N-methylnicotinamide (8 g, 39.9 mmol), potassium phosphate tribasic (16.93 g, 80 mmol), trans-1-propen-1-ylboronic acid (3.77 g, 43.9 mmol) and dioxane (100 ml). The reaction was purged with nitrogen and heated at 80° C. for 12 h. Then it was cooled to room temperature, diluted with water (200 mL) and extracted with ethyl acetate (3×150 mL). The combined organic layers were washed with brine, dried over sodium sulfate, and concentrated in vacuo. The residue was purified by silica gel (BIOTAGE flash 65M, 0-100% ethyl acetate in hexane) to give the title compound. LC/MS (m/z): 207 (M+H)$^+$.

Step B: N-Methoxy-N-methyl-6-propylnicotinamide

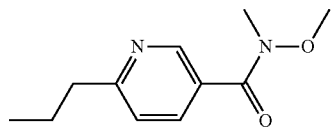

(E)-N-methoxy-N-methyl-6-(prop-1-en-1-yl)nicotinamide (7.2 g, 34.9 mmol) and palladium on carbon (1.115 g, 1.047 mmol) in MeOH (50 ml) was shaken under 20 psi hydrogen for 1.5 h at room temperature. The reaction mixture was filtrated through CELITE and concentrated. The residue was purified by BIOTAGE (65M, 0-100% ethyl acetate in hexane) to give the title compound. $^1$H NMR (500 MHz, CDCl$_3$) δ 9.09 (d, 1H), 8.16 (dd, 1H), 7.27 (d, 1H), 2.85 (dd, 2H), 2.63 (s, 3H), 1.80 (m, 2H), 0.99 (t, 3H); LC/MS (m/z): 209 (M+H)$^+$.

Step C: 6-Propylnicotinaldehyde

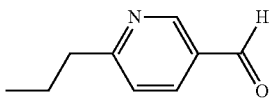

DIBAL-H (14.98 ml, 14.98 mmol) was added dropwise over 2 min. to a solution of N-methoxy-N-methyl-6-propyl-nicotinamide (2.6 g, 12.48 mmol) in toluene (40 ml), cooled to −78° C. After it was stirred for 30 min, the reaction was warmed to −10° C. for 30 min. The reaction was quenched with 1 N HCl (20 mL) and basified by sodium carbonate. The mixture was extracted with ethyl acetate (3×60 mL). The combined organic layers were washed with brine, dried over sodium sulfate, filtrated and concentrated under reduced pressure. The residue was purified by BIOTAGE (40M, 0-100% ethyl acetate in hexane) to give the title compound.

Step D: 7-Bromo-2-((6-propylpyridin-3-yl)methyl)-1,2,3,4-tetrahydroisoquinoline

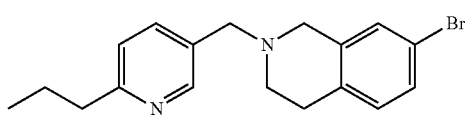 [SMILES: CCCc1ccc(CN2CCc3ccc(Br)cc3C2)cn1]

Sodium cyanoborohydride (1.483 g, 23.59 mmol) was added in one portion to a solution of 6-propylnicotinaldehyde (1.76 g, 11.80 mmol) and 7-bromo-1,2,3,4-tetrahydroisoquinoline (3.00 g, 14.16 mmol) in DMF (36 ml) and acetic acid (4 ml). The reaction mixture became slightly warm after 2 min. The reaction was stirred for 30 min and was diluted with MTBE. The organic solution was washed with saturated aqueous sodium carbonate (10%), water, and brine in sequence. The organic layer was dried over sodium sulfate, filtered and concentrated under reduced pressure. The residue was purified by BIOTAGE (100M, 0-100% ethyl acetate in hexane) to give the title compound. LC/MS (m/z): 345, 347 (M+H)$^+$.

Step E: 7-(Benzylthio)-2-((6-propylpyridin-3-yl)methyl)-1,2,3,4-tetrahydroisoquinoline

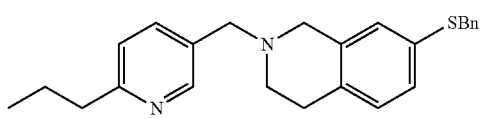

A solution of 7-Bromo-2-((6-propylpyridin-3-yl)methyl)-1,2,3,4-tetrahydroisoquinoline (4 g, 11.58 mmol), Pd$_2$(dba)$_3$ (0.265 g, 0.290 mmol) and Xantphos (0.503 g, 0.869 mmol) in dioxane (100 ml) was bubbled with nitrogen for 20 min, to which were added TEA (4.1 ml, 23.54 mmol) and benzyl thiol (1.8 ml, 15.33 mmol). The reaction mixture was heated at 102° C. for 3 h. The reaction mixture was cooled to room temperature, diluted with ethyl acetate and washed with water and brine in sequence. The organic layer was dried over sodium sulfate and concentrated. The residue was purified by BIOTAGE (100 M, 0-100% ethyl acetate in hexane) to give the title compound. LC/MS (m/z): 389 (M+H)$^+$.

Step F: 7-(Chlorosulfonyl)-2-((6-propylpyridin-3-yl)methyl)-1,2,3,4-tetrahydroisoquinolin-2-ium Chloride

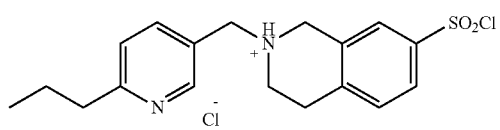

Acetic acid (2.110 ml, 36.9 mmol) and water (0.664 ml, 36.9 mmol) were added to a solution of 7-(benzylthio)-2-((6-propylpyridin-3-yl)methyl)-1,2,3,4-tetrahydroisoquinoline (3.58 g, 9.21 mmol) in DCM (30 ml). The mixture was cooled in an ice-water bath and sulfuryl chloride (3.00 ml, 36.9 mmol) was added dropwise over 2 min. The mixture was stirred for 20 min, then, the bath was removed and the reaction was allowed to warm to room temperature stirring for 2 h. The reaction mixture was filtrated and washed with TBME. The residue was dried under high vacuum to afford the title compound. LC/MS (m/z): 365 (M+H)$^+$.

Step G: N-(4-Bromo-5-(tert-butyl)isoxazol-3-yl)-2-((6-propylpyridin-3-yl)methyl)-1,2,3,4-tetrahydroisoquinoline-7-sulfonamide

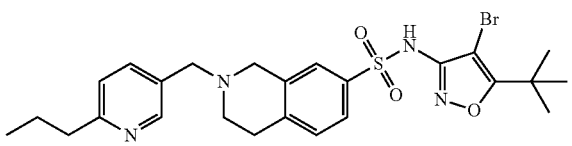 [SMILES: CCCc1ccc(CN2CCc3ccc(S(=O)(=O)Nc4noc(C(C)(C)C)c4Br)cc3C2)cn1]

LiHMDS (19.93 ml, 19.93 mmol) was added dropwise at −78° C. with magnetic stirring under nitrogen to a solution of 7-(chlorosulfonyl)-2-((6-propylpyridin-3-yl)methyl)-1,2,3,4-tetrahydroisoquinolin-2-ium chloride and 4-bromo-5-(tert-butyl)isoxazol-3-amine (1.310 g, 5.98 mmol) in THF (20 ml). The reaction mixture was stirred for 20 min and allowed to warm to room temperature stirring for 30 min. LC-MS showed the completion of the reaction. After it was quenched with ammonium chloride, the mixture was extracted with ethyl acetate. The organic layer was washed with brine, dried over sodium sulfate, filtered and concentrated in vacuo. The residue was purified by BIOTAGE (Flash 40M, 0-10% MeOH in DCM) to give the title compound. LC/MS (m/z): 548 (M+H)$^+$. MGAT2 Human IC$_{50}$: 6.8 nM.

Example 42

Preparation of (R)—N-(5-(tert-butyl)-4-methylisoxazol-3-yl)-2-(1-(6-ethylpyridin-3-yl)ethyl)-1,2,3,4-tetrahydroisoquinoline-7-sulfonamide

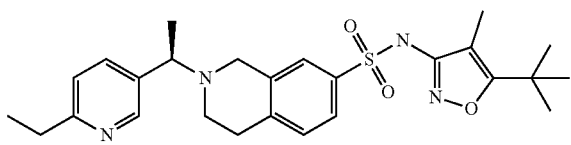 [SMILES: CCc1ccc([C@@H](C)N2CCc3ccc(S(=O)(=O)Nc4noc(C(C)(C)C)c4C)cc3C2)cn1]

Step A: (R)-7-Bromo-2-(1-(6-ethylpyridin-3-yl)ethyl)-1,2,3,4-tetrahydroisoquinoline

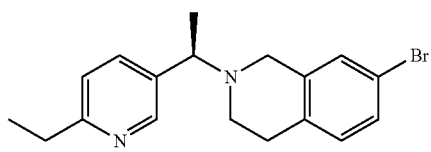 [SMILES: CCc1ccc([C@@H](C)N2CCc3ccc(Br)cc3C2)cn1]

4-bromo-1-(2-bromoethyl)-2-(bromomethyl)benzene (2.11 g, 5.92 mmol) was added to a solution of (R)-1-(6-ethylpyridin-3-yl)ethanamine (890 mg, 5.92 mmol) and potassium carbonate (2.46 g, 17.77 mmol) in ethanol (30 ml), and the reaction mixture was heated at reflux for 2 hours. The reaction was cooled to room temperature, poured into water, extracted with EtOAc×2. The combined organics were washed with brine, dried over MgSO$_4$, filtered and concentrated in vacuo. The residue was purified by column chromatography (0-70% EtOAc/hexanes, BIOTAGE 40 M) to give the title compound. LC/MS (m/z): 346 (M+H)$^+$.

Step B: (R)-7-(Benzylthio)-2-(1-(6-ethylpyridin-3-yl)ethyl)-1,2,3,4-tetrahydroisoquinoline

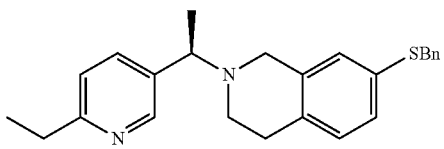

A solution of (R)-7-bromo-2-(1-(6-ethylpyridin-3-yl)ethyl)-1,2,3,4-tetrahydroisoquinoline (550 mg, 1.593 mmol), Pd$_2$(dba)$_3$ (36.5 mg, 0.040 mmol) and Xantphos (69.1 mg, 0.119 mmol) in dioxane (10 ml) was bubbled nitrogen for 20 min. Then TEA (0.555 ml, 3.19 mmol) and benzyl thiol (0.206 ml, 1.752 mmol) were added. The reaction mixture was heated at 102° C. for 3 h. After it was cooled to room temperature, the reaction was diluted with ethyl acetate and washed with water and brine in sequence. The organic layers were dried over sodium sulfate and concentrated. The residue was purified by BIOTAGE (40 M, 0-100% ethyl acetate in hexane) to give the title compound. LC/MS (m/z): 389 (M+H)$^+$.

Step C: (R)-2-(1-(6-Ethylpyridin-3-yl)ethyl)-1,2,3,4-tetrahydroisoquinoline-7-sulfonyl Chloride

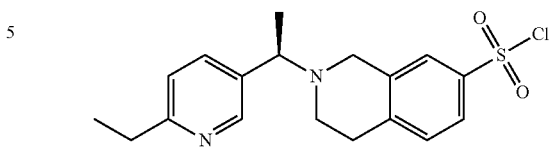

Acetic acid (0.130 ml, 2.265 mmol) and water (0.041 ml, 2.265 mmol) were added to a solution of (R)-7-(benzylthio)-2-(1-(6-ethylpyridin-3-yl)ethyl)-1,2,3,4-tetrahydroisoquinoline (220 mg, 0.566 mmol) in DCM (5 ml). The mixture was cooled in an ice-water bath and to which was added sulfuryl chloride (0.184 ml, 2.265 mmol) dropwise over 2 min. The mixture was stirred for 20 min. The bath was removed and the reaction was allowed to warm to room temperature and stirred for 2 h. The reaction was diluted with ethyl acetate and washed with sodium bicarbonate and brine in sequence. The organic layer was dried over sodium sulfate and purified by BIOTAGE (25M, 0-100% ethyl acetate) to give the title compound. LC/MS (m/z): 365 (M+H)$^+$.

Step D: (R)—N-(5-(tert-Butyl)-4-methylisoxazol-3-yl)-2-(1-(6-ethylpyridin-3-yl)ethyl)-1,2,3,4-tetrahydroisoquinoline-7-sulfonamide

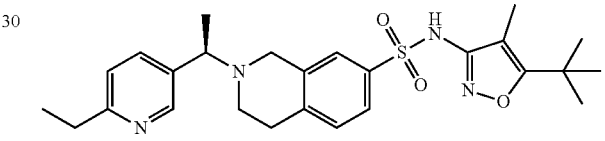

A solution of (R)-2-(1-(6-ethylpyridin-3-yl)ethyl)-1,2,3,4-tetrahydroisoquinoline-7-sulfonyl chloride (50 mg, 0.137 mmol) and 5-(tert-butyl)-4-methylisoxazol-3-amine (31.7 mg, 0.206 mmol) in THF (1 ml) was cooled to −78° C., to which was added LHMDS (1 M in THF, 0.411 ml, 0.411 mmol) dropwise. The reaction was stirred for 30 min and allowed to warm to room temperature. The reaction was stirred at room temperature for another 1 h, then it was quenched with ammonium chloride, extracted with ethyl acetate. The combined organic layers were dried and concentrated. The residue as purified by HPLC to give the desired product as a solid. $^1$H NMR (500 MHz, CD3OD) δ 8.88 (s, 1H), 8.71 (d, 1H), 7.76 (m, 2H), 7.67 (s, 1H), 7.30 (d, 1H), 4.53 (m, 1H), 4.31 (d, 2H), 4.10 (d, 2H), 3.61 (m, 1H), 3.51 (m, 1H), 3.21 (m, 2H), 3.14 (q, 2H), 1.98 (s, 2H), 1.87 (d, 3H), 1.45 (t, 3H), 1.31 (s, 9H); LC/MS (m/z): 483 (M+H)$^+$. MGAT2 Human IC$_{50}$: 8.2 nM.

Example 43

Preparation of (R)—N-(4-bromo-5-(tert-butyl)isoxazol-3-yl)-2-(1-(6-propylpyridin-3-yl)ethyl)-1,2,3,4-tetrahydroisoquinoline-7-sulfonamide

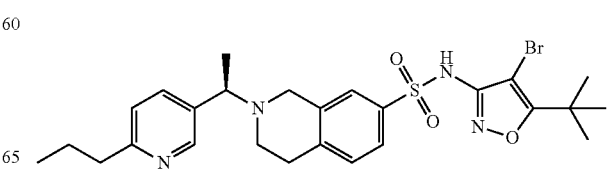

Step A: (E)-2-Methyl-N-(1-(6-propylpyridin-3-yl)ethylidene)propane-2-sulfinamide

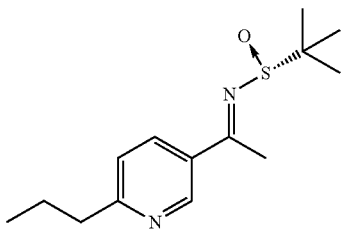 [SMILES: CCCc1ccc(/C(C)=N/[S@](=O)C(C)(C)C)cn1]

Titanium(IV) ethoxide (4.57 ml, 22.06 mmol) was added to a solution of 1-(6-propylpyridin-3-yl)ethanone (1.8 g, 11.03 mmol) and (R)-(+)-2-methyl-2-propanesulfinamide (1.738 g, 14.34 mmol) in THF (50 ml) under nitrogen. The mixture was heated at 60° C. for 3 h. It was cooled overnight, concentrated and purified by ISCO (SNAP 125 g, 0-100% ethyl acetate) to give the title compound. LC/MS (m/z): 267 (M+H)+.

Step B: 2-Methyl-N—((R)-1-(6-propylpyridin-3-yl)ethyl)propane-2-sulfinamide

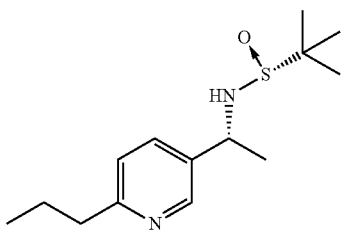 [SMILES: CCCc1ccc([C@@H](C)N[S@](=O)C(C)(C)C)cn1]

To a solution of (E)-2-methyl-N-(1-(6-propylpyridin-3-yl)ethylidene)propane-2-sulfinamide (2.44 g, 9.16 mmol) in THF (30 ml) cooled at 0° C. was added L-Selectride (15 ml, 15.00 mmol) dropwise. It was warmed to room temperature stirring for 15 min. TLC and LC-MS showed the completion of the reaction. The mixture was concentrated and purified by ISCO (5-10% methanol in DCM) to give the title compound (dr>98:2). LC/MS (m/z): 269 (M+H)+.

Step C: (R)-1-(6-Propylpyridin-3-yl)ethanaminium Chloride

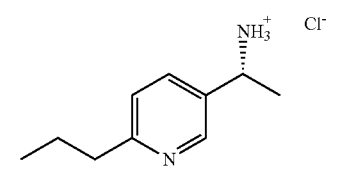

2-methyl-N—((R)-1-(6-propylpyridin-3-yl)ethyl)propane-2-sulfinamide (2.07 g, 7.71 mmol) was treated with 4 M HCl in dioxane (20 ml, 80 mmol) and stirred at room temperature overnight. It was concentrated and diluted with TBME, filtered and dried under reduced pressure to give the title compound. LC/MS (m/z): 165 (M+H)+.

Step D: (R)-7-Bromo-2-(1-(6-propylpyridin-3-yl)ethyl)-1,2,3,4-tetrahydroisoquinoline

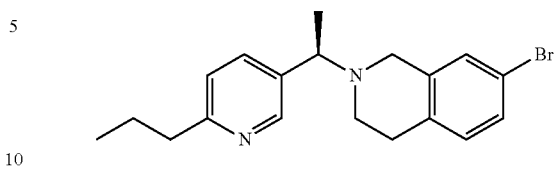

DIEA (5.57 ml, 31.9 mmol) was added at room temperature to a suspension of (R)-1-(6-propylpyridin-3-yl)ethanaminium chloride (1.5 g, 7.47 mmol) in EtOH (80 ml). To the solution was added 4-bromo-1-(2-bromoethyl)-2-(bromomethyl)benzene (2.84 g, 7.97 mmol) in one portion. The reaction was stirred at 80° C. for 3 h. It was cooled to room temperature, and concentrated under vacuum. The residue was partitioned in ethyl acetate and water. The organic layer was washed with brine, dried over sodium sulfate, filtered and concentrated. The residue was purified by ISCO (SNAP 100, 0-100% ethyl acetate) to give the title compound. LC/MS (m/z): 361 (M+H)+.

Step E: (R)-7-Bromo-2-(1-(6-propylpyridin-3-yl)ethyl)-1,2,3,4-tetrahydroisoquinoline

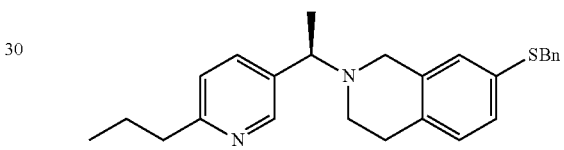

A mixture of (R)-7-bromo-2-(1-(6-propylpyridin-3-yl)ethyl)-1,2,3,4-tetrahydroisoquinoline (1.5 g, 4.17 mmol), Pd$_2$(dba)$_3$ (0.096 g, 0.104 mmol) and 4,5-bis(diphenylphosphino)-9,9-dimethylxanthene (0.181 g, 0.313 mmol) in dioxane (20 ml) was bubbled nitrogen for 20 min. Then TEA (1.164 ml, 8.35 mmol) and benzyl mercaptan (0.570 g, 4.59 mmol) were added. The reaction mixture was heated at 102° C. for 3 h. It was cooled to room temperature, diluted with ethyl acetate and washed with water and brine in sequence. The organic solution was dried over sodium sulfate and concentrated. The residue was purified by ISCO (SNAP 100, 0-100% ethyl acetate in hexane) to give the title compound. LC/MS (m/z): 403 (M+H)+.

Step F: (R)-7-Bromo-2-(1-(6-propylpyridin-3-yl)ethyl)-1,2,3,4-tetrahydroisoquinoline

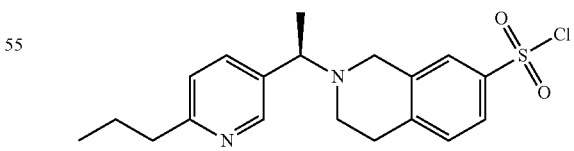

Acetic acid (0.882 ml, 15.40 mmol) and water (0.277 ml, 15.40 mmol) were added to (R)-7-bromo-2-(1-(6-propylpyridin-3-yl)ethyl)-1,2,3,4-tetrahydroisoquinoline (1.55 g, 3.85 mmol) in DCM (20 ml). The mixture was cooled to 0° C. to which was added sulfuryl chloride (1.252 ml, 15.40 mmol) dropwise. After the addition, the reaction mixture was allowed to warm to room temperature and stirred for 3 h. It was concentrated and purified by ISCO (SNAP 25M, 0-100% ethyl acetate in hexane) to give the title compound.

Step G: (R)—N-(4-Bromo-5-(tert-butyl)isoxazol-3-yl)-2-(1-(6-propylpyridin-3-yl)ethyl)-1,2,3,4-tetrahydroisoquinoline-7-sulfonamide

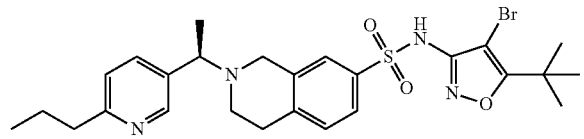 [SMILES: CCCc1ccc([C@@H](C)N2CCc3ccc(S(=O)(=O)Nc4noc(C(C)(C)C)c4Br)cc3C2)cn1]

A solution of (R)-7-bromo-2-(1-(6-propylpyridin-3-yl)ethyl)-1,2,3,4-tetrahydroisoquinoline (660 mg, 1.742 mmol) and 4-bromo-5-(tert-butyl)isoxazol-3-amine (496 mg, 2.264 mmol) in THF (10 ml) was cooled to −78° C. and LHMDS (4.53 ml, 4.53 mmol) was added dropwise. The mixture was stirred for 30 min and allowed to warm to room temperature stirring for 1 h. The reaction was quenched with ammonium chloride and extracted with ethyl acetate. The organic layer was dried over sodium sulfate, filtered and concenrated. The residue was purified by HPLC to give the title compound. LC/MS (m/z): 561, 563 (M+H)$^+$. MGAT2 Human IC$_{50}$: 1.6 nM.

Example 44

Preparation of N-(4-bromo-5-(tert-butyl)isoxazol-3-yl)-6-(3,5-difluorobenzyl)-5,6,7,8-tetrahydro-1,6-naphthyridine-3-sulfonamide Trifluoroacetate

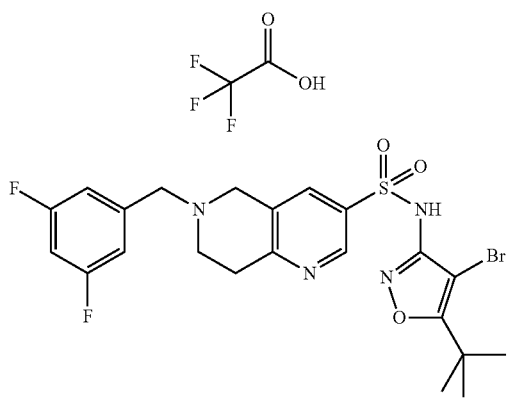

Step A: Benzyl 3-nitro7,8-dihydro-1,6-naphthyridine-6(5H)-carboxylate

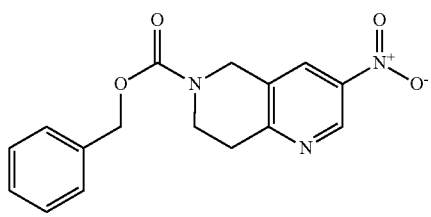 [SMILES: O=C(OCc1ccccc1)N1CCc2ncc([N+](=O)[O-])cc2C1]

A microwave vial was charged with 7M methanolic ammonia (7 ml, 49 mmol), N-benzyloxycarbonyl-4-piperidone (1.43 g, 6.13 mmol), and 1-methyl-3,5-dinitro-1H-pyridin-2-one (1.16 g, 5.83 mmol). The microwave vial was capped and heated at 120° C. for 20 minutes in the microwave. The reaction mixture was cooled to room temperature and filtered through a fritted funnel to yield the crude title compound. LC/MS (m/z): 314 (M+H)$^+$.

The filtrate was concentrated under reduced pressure and recrystallized from methanol to yield an additional amount of the crude title compound. LC/MS 314 (M+H)$^+$.

Step B: Benzyl 3-amino-7,8-dihydro-1,6-naphthyridine-6(5H)-carboxylate

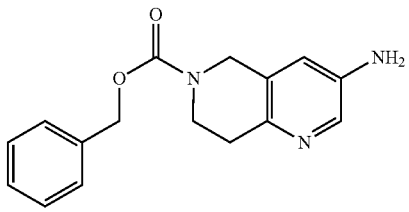 [SMILES: Nc1cnc2c(c1)CN(C(=O)OCc1ccccc1)CC2]

Iron powder (1.67 g, 29.9 mmol) was added to a solution of benzyl 3-nitro7-8-dihydro-1,6-naphthyridine-6(5H)-carboxylate (1.74 g, 5.55 mmol) in 1N hydrochloric acid (69 ml). It was heated at 80° C. for 1 hour. The reaction mixture was cooled to room temperature, basified by addition of 1N sodium hydroxide (73 ml, 73 mmol) and extracted 3 times with EtOAc. The organic extracts were combined, washed with brine, dried over MgSO$_4$, filtered, and concentrated under reduced pressure to afford the crude title compound. LC/MS (m/z): 284 (M+H)$^+$.

Step C: Benzyl 3-bromo-7,8-dihydro-1,6-naphthyridine-6(5H)-carboxylate

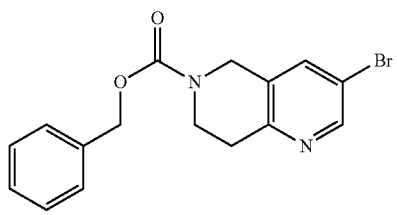 [SMILES: O=C(OCc1ccccc1)N1CCc2ncc(Br)cc2C1]

Benzyl 3-amino-7-8-dihydro-1,6-naphthyridine-6(5H)-carboxylate (1.48 g, 5.22 mmol) was added to an ice cold solution of concentrated hydrobromic acid (15 ml, 276 mmol) and water (15 ml). It was cooled to −10° C. and a solution of sodium nitrite (3.96 g, 5.74 mmol) in water (4 mL) was added slowly. It was stirred at −10 to −5° C. for 30 minutes and copper(I) bromide (547 mg, 3.81 mmol) was added. The reaction was allowed to warm slowly to room temperature and was then poured into saturated aqueous NaHCO$_3$ solution. Saturated aqueous NH$_3$ solution was added to solubilize copper salts. It was extracted 3 times with EtOAc. The organic extracts were combined, washed with brine, dried over MgSO$_4$, filtered, and concentrated under reduced pressure. The residue was purified by flash column chromatography on silica using a gradient 30% EtOAc in hexanes to 100% EtOAc to afford the title compound. LC/MS (m/z): 347, 349 (M+H)$^+$.

Step D: 3-bromo-5,6,7,8-tetrahydro-1,6-naphthyridine Dihydrochloride

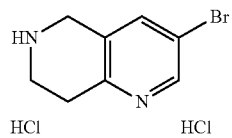

3N Hydrochloric acid (5 ml, 15 mmol) was added to benzyl 3-bromo-7,8-dihydro-1,6-naphthyridine-6(5H)-carboxylate. The reaction was heated at reflux for 2 hours. The mixture was then cooled and concentrated under reduced pressure to yield the crude title compound. 213, 215 (M+H)$^+$.

Step E: 1-(3-bromo-7,8-dihydro-1,6-naphthyridin-6(5H)-yl)-2,2,2-trifluoroethanone

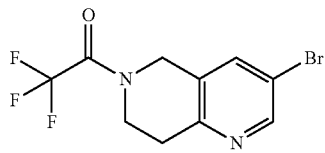 [SMILES: O=C(N1CCc2ncc(Br)cc2C1)C(F)(F)F]

Triethylamine (0.6 ml, 4.3 mmol) was added to a suspension of 3-bromo-5,6,7,8-tetrahydro-1,6-naphthyridine-dihydrochloride (332 mg, 1.61 mmol) in DCM (5 ml) followed by trifluoroacetic anhydride (0.2 ml, 1.41 mmol). The reaction was stirred at room temperature for 20 hours. It was poured into saturated aqueous NaHCO$_3$ solution and extracted 3 times with EtOAc. The organic extracts were combined, washed with brine, dried over MgSO$_4$, filtered, and concentrated under reduced pressure. The residue was purified by flash column chromatography on silica using 30% EtOAc in hexanes to afford the title compound. LC/MS (m/z): 309, 311 (M+H)$^+$.

Step F: 1-(3-(tert-butylthio)-7,8-dihydro-1,6-naphthyridin-6(5H)-yl)-2,2,2-trifluoroethanone

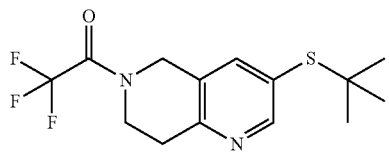 [SMILES: CC(C)(C)Sc1cnc2c(c1)CN(C(=O)C(F)(F)F)CC2]

2-Methyl-2-propanethiol (0.12 ml, 1.07 mmol) was introduced to a solution of 1-(3-bromo-7,8-dihydro-1,6-naphthyridin-6(5H)-yl)-2,2,2-trifluoroethanone (296 mg, 0.958 mmol), palladium(II)acetate (3.6 mg, 0.04 mmol), and lithium bis(trimethylsilyl)amide (1 ml, 1 mmol) in anhydrous DME (3.6 ml) that had been degassed with N$_2$. The vial was capped, evacuated and backfilled with N$_2$×2, and the mixture heated at 110° C. for 20 hrs. Silica was added and the solvent evaporated under reduced pressure. The residue was purified by flash column chromatography on silica using 30% ETOAc in hexanes to afford the title compound (194 mg, 63.6%). LC/MS (m/z): 319 (M+H)$^+$.

Step G: 6-(2,2,2-trifluoroacetyl)-5,6,7,8-tetrahydro-1,6-naphthyridine-3-sulfonyl Chloride

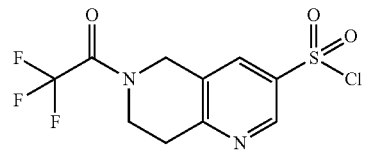 [SMILES: O=C(N1CCc2ncc(S(=O)(=O)Cl)cc2C1)C(F)(F)F]

Acetic acid (0.135 ml, 2.36 mmol) was added to a solution of 1-(3-(tert-butylthio)-7,8-dihydro-1,6-naphthyridin-6(5H)-yl)-2,2,2-trifluoroethanone (194 mg, 0.609 mmol) in DCM (40 ml) followed by water (0.054 ml, 3 mmol) and sulfuryl chloride (0.189 ml, 2.325 mmol). The reaction was stirred at room temperature for 20 minutes. It was diluted with EtOAc and washed with 2% aqueous NaHCO$_3$ solution and extracted 3 times with EtOAc. The organic extracts were combined, washed with brine, dried over MgSO$_4$, filtered, and concentrated under reduced pressure. The residue was determined to be a 6:1 mixture of title compound and disulfide. The residue was dissolved in DCM (40 ml) and acetic acid (0.135 ml, 2.36 mmol) was added followed by water (0.054 ml, 3 mmol) and sulfuryl chloride (0.189 ml, 2.325 mmol). The reaction was stirred at room temperature for 20 minutes. It was diluted with EtOAc and washed with 2% aqueous NaHCO$_3$ solution and extracted 3 times with EtOAc. The organic extracts were combined, washed with brine, dried over MgSO$_4$, filtered, and concentrated under reduced pressure to afford the title compound. LC/MS (m/z): 329, 331 (M+H)$^+$.

Step H: N-(4-bromo-5-(tert-butyl)-3-yl)-5,6,7,8-tetrahydro-1,6-naphthyridine-3-sulfonamide 2,2,2-trifluoroacetate

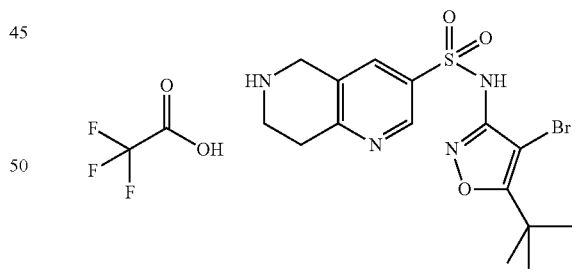

Lithium bis(trimethylsilyl)amide (1.1 ml, 1.1 mmol) was added slowly to a solution of 4-bromo-5-(tert-butyl)isoxazole-3-amine (241 mg, 1.1 mmol) in THF (0.4 ml). The mixture was stirred at room temperature for 5 minutes and a solution of 6-(2,2,2-trifluoroacetyl)-5,6,7,8-tetrahydro-1,6-naphthyridine-3-sulfonyl chloride (81 mg, 0.246 mmol) in THF (0.2 ml) was added. The flask was rinsed with THF (0.2 ml) and was added to the reaction. The mixture was stirred at room temperature for 20 hours. TFA (0.1 ml) in water was added. The mixture was concentrated under reduced pressure. The residue was purified by reverse phase HPLC on a SUNFIRE column using a gradient from 15% acetonitrile with 0.05% TFA in water to 100% acetonitrile to yield the title compound. LC/MS (m/z): 415, 417 (M+H)+.

Step I: N-(4-bromo-5-(tert-butyl)isoxazol-3-yl)-6-(3,5-difluorobenzyl-5,6,7,8-tetrahydro-1,6-naphthyridine-3-sulfonamide 2,2,2-trifluoroacetate

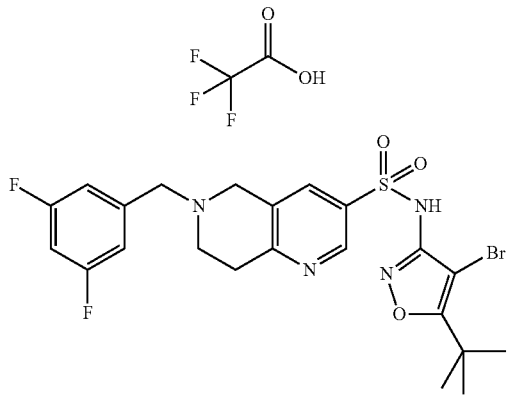

Acetic acid (0.021 ml, 0.367 mmol) was added to a suspension of N-(4-bromo-5-(tert-butyl)-3-yl)-5,6,7,8-tetrahydro-1,6-naphthyridine-3-sulfonamide 2,2,2-trifluoroacetate (39.2 mg, 0.074 mmol) followed by 3,5-difluorobenzaldehyde (31 mg, 0.218 mmol). The mixture was stirred at room temperature for 15 minutes and MP-CNBH$_3$ (2.19 mmol/g) (253 mg, 0.074 mmol) was added. After stirring at room temperature for 20 hours, additional MP-CNBH$_3$ (2.19 mmol/g) (258 mg, 0.074 mmol) was added followed by 3,5-difluorobenzaldehyde (34 mg, 0.239 mmol), THF (0.5 ml) and methanol (0.25 ml). The reaction was heated at 50° C. for 6 hours. The reaction mixture was filtered through a fritted funnel, washed with methanol and concentrated under reduced pressure. The residue was purified by reverse phase HPLC on a SUNFIRE column using a gradient from 15% acetonitrile with 0.05% TFA in water to 100% acetonitrile to yield the title compound. $^1$H NMR (500 MHz, CD$_3$OD) δ 9.02 (br d, 1H), 8.25 (br d, 1H), 7.23 (br dd, 2H), 7.15 (br tt, 1H), 4.49 (s, 2H), 4.48 (s, 2H), 3.67 (br t, 2H), 3.35 (t, 2H), 1.38 (s, 9H). LC/MS (m/z): 541, 543 (M+H)+. MGAT2 Human IC$_{50}$: 118 nM.

Example 45

Preparation of 7-(N-(5-propylpyrazin-2-yl)sulfamoyl)-2-((R)-1-(6-(2,2,2-trifluoroethoxy)pyridin-3-yl)ethyl)-1,2,3,4-tetrahydroisoquinolin-2-ium 2,2,2-trifluoroacetate

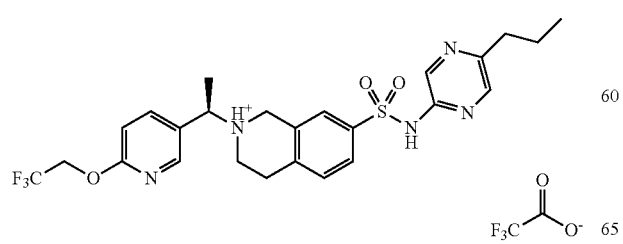

Starting with Intermediate 3 and following the same procedure described in Example 38, the title compound was prepared. $^1$H NMR (400 MHz, d$_6$-DMSO) δ 8.35 (s, 1H), 8.28 (s, 1H), 8.08 (s, 1H), 8.01 (d, 1H), 7.81 (m, 2H), 7.45 (d, 1H), 7.12 (d, 1H), 5.02 (q, 2H), 4.75 (m, 1H), 4.40 (m, 4H), 3.12 (m, 2H), 2.60 (t, 2H), 1.71 (d, 3H), 1.59 (q, 2H), 0.84 (t, 3H). LC/MS (m/z): 536.0 (M+H)+. MGAT2 Human IC$_{50}$: 7.3 nM.

Example 46

Preparation of 2-((R)-1-(6-(2,2-difluoroethoxy)pyridin-3-yl)ethyl)-7-(N-(5-ethylpyrazin-2-yl)sulfamoyl)-1,2,3,4-tetrahydroisoquinolin-2-ium 2,2,2-trifluoroacetate

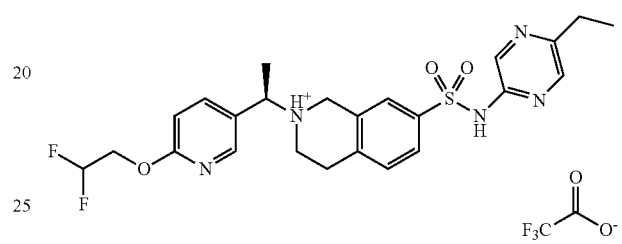

Following the same procedure described in Example 22 and using 5-ethylpyrazin-2-amine, the title compound was prepared. $^1$H NMR (400 MHz, d$_6$-DMSO) δ 8.31 (s, 1H), 8.28 (s, 1H), 8.10 (s, 1H), 7.96 (d, 1H), 7.81 (m, 2H), 7.45 (d, 1H), 7.06 (d, 1H), 6.40 (tt, 1H), 4.72 (m, 1H), 4.60 (td, 2H), 4.40 (m, 1H), 4.17 (m, 1H), 3.88 (m, 1H), 3.57 (m, 1H), 3.10 (m, 2H), 2.65 (q, 2H), 1.71 (d, 3H), 1.16 (t, 3H). LC/MS (m/z): 504.0 (M+H). MGAT2 Human IC$_{50}$: 12.7 nM.

Example 47

Preparation of 7-(N-(5-(isopropylamino)pyrazin-2-yl)sulfamoyl)-2-((R)-1-(6-(2,2,2-trifluoroethoxy)pyridin-3-yl)ethyl)-1,2,3,4-tetrahydroisoquinolin-2-ium 2,2,2-trifluoroacetate

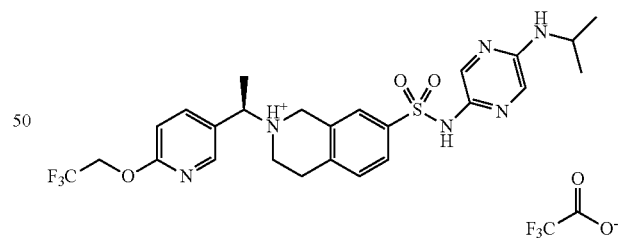

Step A: N-isopropyl-5-nitropyrazin-2-amine

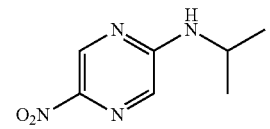

To isopropylamine (0.5 mL, 5.84 mmol), 2-chloro-5-nitropyrazine (100 mg, 0.627 mmol) was added. After 5 minutes of vigorous stirring, the reaction was diluted with EtOAc, washed with water, dried over MgSO$_4$, filtered, concentrated in vacuo and purified by column chromatography (5-50% EtOAc/hexanes, REDI-SEP-4 gram) to give the title compound. LC/MS (m/z): 183.1 (M+H)$^+$.

Step B: N-isopropylpyrazine-2,5-diamine

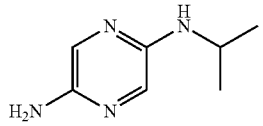

Iron (118 mg, 2.108 mmol) was added to N-isopropyl-5-nitropyrazin-2-amine (96 mg, 0.527 mmol) in THF (2 mL), MeOH (1 mL), water (0.5 mL), and saturated NH$_4$Cl (0.5 mL) and the reaction mixture heated at 60° C. After 1 hour, the mixture was cooled to room temperature, diluted with MeOH, filtered through CELITE, the filter cake washed with MeOH, and the combined filtrates concentrated in vacuo. The residue was partitioned between EtOAc and 50% sat. NaHCO$_3$, and the aqueous extracted with EtOAc. The combined organics were dried over MgSO$_4$, filtered and concentrated in vacuo to give the title compound. LC/MS (m/z): 153.1 (M+H)$^+$.

Step C: 7-(N-(5-(isopropylamino)pyrazin-2-yl)sulfamoyl)-2-((R)-1-(6-(2,2,2-trifluoroethoxy)pyridin-3-yl)ethyl)-1,2,3,4-tetrahydroisoquinolin-2-ium 2,2,2-trifluoroacetate

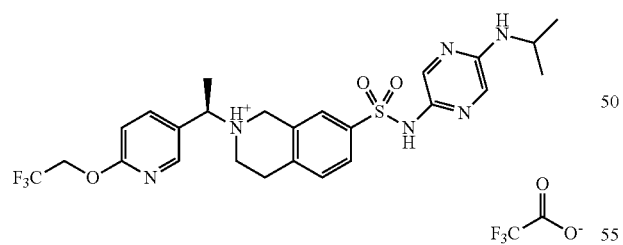

Using Intermediate 3 and the compound of Step B and following the same procedure described in Example 13, the title compound was prepared. $^1$H NMR (400 MHz, d$_6$-DMSO) δ 8.35 (s, 1H), 8.00 (s, 1H), 7.76 (s, 1H), 7.64 (m, 2H), 7.50 (s, 1H), 7.42 (d, 1H), 7.12 (d, 1H), 6.80 (s, 1H), 5.02 (q, 2H), 4.73 (m, 1H), 4.40 (m, 1H), 4.15 (m, 1H), 3.85 (m, 2H), 3.10 (m, 3H), 1.71 (m, 3H), 1.10 (d, 6H). LC/MS (m/z): 551.2 (M+H)$^+$. MGAT2 Human IC$_{50}$: 13.9 nM.

Example 48

Preparation of 7-(N-(5-cyclopropylpyrazin-2-yl)sulfamoyl)-2-((R)-1-(6-(2-methoxyethoxy)pyridin-3-yl)ethyl)-1,2,3,4-tetrahydroisoquinolin-2-ium 2,2,2-trifluoroacetate

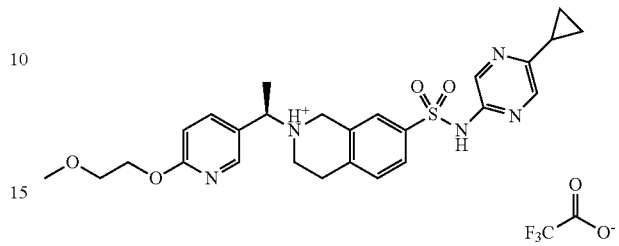

Following the same procedure described in Example 31, and using 5-cyclopropylpyrazin-2-amine the title compound was prepared. $^1$H NMR (400 MHz, d$_6$-DMSO) δ 8.28 (m, 1H), 8.20 (s, 1H), 8.16 (s, 1H), 7.87 (m, 2H), 7.77 (d, 1H), 7.43 (d, 1H), 6.95 (d, 1H), 4.71 (m, 1H), 4.40 (t, 2H), 3.74 (m, 3H), 3.66 (t, 2H), 3.28 (s, 3H), 3.13 (m, 3H), 2.06 (m, 1H), 1.70 (d, 3H), 0.93 (m, 2H), 0.79 (m, 2H). LC/MS (m/z): 510.1 (M+H)$^+$. MGAT2 Human IC$_{50}$: 21.3 nM.

Example 49

Preparation of (R)—N-(6-methoxypyridazin-3-yl)-2-(1-(6-(2,2,2-trifluoroethoxy)pyridin-3-yl)ethyl)-1,2,3,4-tetrahydroisoquinoline-7-sulfonamide

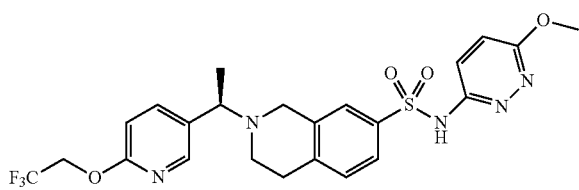 [SMILES: COc1ccc(NS(=O)(=O)c2ccc3c(c2)CN([C@H](C)c2ccc(OCC(F)(F)F)nc2)CC3)nn1]

Using Intermediate 3 and 6-methoxypyridazin-3-amine, and following the same procedure described in Example 13, the title compound was prepared. $^1$H NMR (400 MHz, CDCl$_3$) δ 8.07 (s, 1H), 7.68 (m, 2H), 7.60 (s, 1H), 7.18 (m, 2H), 7.00 (d, 1H), 6.84 (d, 1H), 4.76 (m, 2H), 3.89 (s, 3H), 3.79 (m, 1H), 3.61 (m, 2H), 2.85 (m, 2H), 2.69 (m, 2H), 1.45 (d, 3H). LC/MS (m/z): 524.1 (M+H)$^+$. MGAT2 Human IC$_{50}$: 8.7 nM.

Example 50

Preparation of 7-(N-(6-(tert-butyl)pyridazin-3-yl)sulfamoyl)-2-((R)-1-(6-(2,2,2-trifluoroethoxy)pyridin-3-yl)ethyl)-1,2,3,4-tetrahydroisoquinolin-2-ium 2,2,2-trifluoroacetate

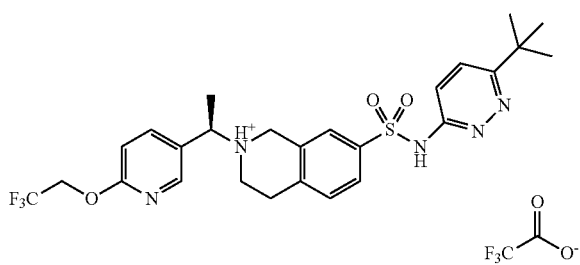

Using Intermediate 3 and 6-ᵗbutylpyridazin-3-amine, and following the same procedure described in Example 13, the title compound was prepared. ¹H NMR (400 MHz, CDCl$_3$) δ 8.34 (m, 1H), 8.00 (m, 1H), 7.91 (d, 1H), 7.80 (m, 1H), 7.70 (m, 2H), 7.37 (d, 1H), 7.13 (d, 1H), 5.02 (q, 2H), 4.73 (m, 2H), 4.38 (m, 1H), 3.13 (m, 4H), 1.71 (d, 3H), 1.22 (s, 9H). LC/MS (m/z): 550.1 (M+H)⁺. MGAT2 Human IC$_{50}$: 3.8 nM.

Example 51

Preparation of (R)-ethyl 5-(2-(1-(3,5-difluorophenyl)ethyl)-1,2,3,4-tetrahydroisoquinoline-7-sulfonamido)-1,2,4-oxadiazole-3-carboxylate

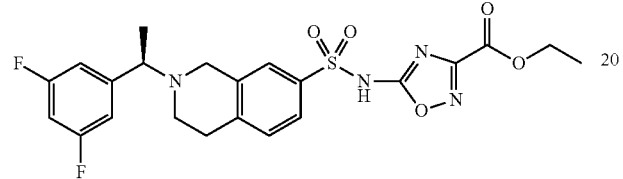

To a solution of Intermediate 5 (1.00 g, 2.69 mmol) and ethyl 5-amino-1,2,4-oxadiazole-3-carboxylate (0.58 mg, 3.36 mmol) in DCM (5 ml), DIEA (2.35 mL, 13.5 mmol) and DMAP (0.164 g, 1.35 mmol) were added. After stirring for 1 h, the reaction was quenched with water, extracted with EtOAc. The organic layer was washed with brine, dried over Na$_2$SO$_4$, filtered and concentrated. The residue was purified by ISCO (10% MeOH in DCM) to afford the title compound. LC/MS (m/z): 493 (M+H)⁺. MGAT2 Human IC$_{50}$: 14 nM.

Example 52

Preparation of (R)-5-(2-(1-(3,5-difluorophenyl)ethyl)-1,2,3,4-tetrahydroisoquinoline-7-sulfonamido)-1,2,4-oxadiazole-3-carboxamide

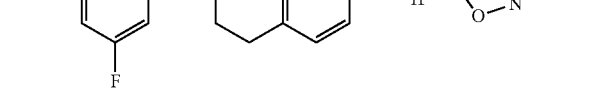

A mixture of (R)-Ethyl 5-(2-(1-(3,5-difluorophenyl)ethyl)-1,2,3,4-tetrahydroisoquinoline-7-sulfonamido)-1,2,4-oxadiazole-3-carboxylate (Example 51 compound, 15 mg, 0.031 mmol) and 7 M solution of ammonia in methanol (0.5 mL) was heated at 50° C. in a sealed vial for 5 h. Most solvent was removed and the residue was purified by HPLC (7-65% MeCN in water with 0.05% TFA) to afford the title compound. LC/MS (m/z): 492 (M+H)⁺. MGAT2 Human IC$_{50}$: 31 nM.

The examples 53-58 in Table 2 were synthesized according to the methods described in Example 52 employing the appropriate amine starting materials.

TABLE 2

| Example # | Chemical Structure | Observed Mass | MGAT2 Human IC$_{50}$ |
|---|---|---|---|
| 53 | ![structure] | 492 [M + H]⁺ | 7.1 nM |
| 54 | ![structure] | 546 [M + H]⁺ | 16 nM |
| 55 | ![structure] | 504 [M + H]⁺ | 3.7 nM |

TABLE 2-continued

| Example # | Chemical Structure | Observed Mass | MGAT2 Human IC$_{50}$ |
|---|---|---|---|
| 56 | 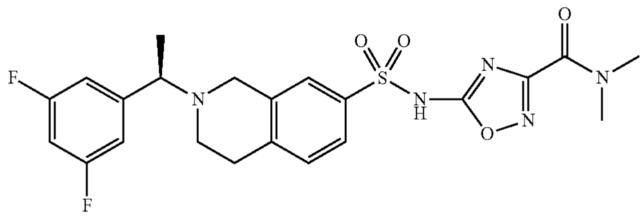 [SMILES: C[C@H](c1cc(F)cc(F)c1)N1CCc2ccc(S(=O)(=O)Nc3nc(C(=O)N(C)C)no3)cc2C1] | 492 [M + H]$^+$ | 5.7 nM |
| 57 | 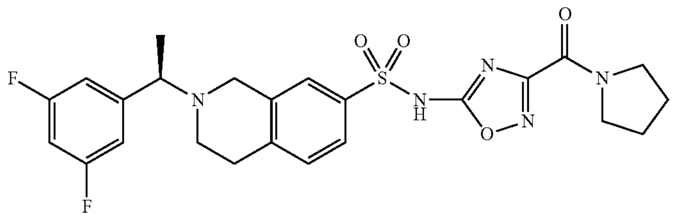 [SMILES: C[C@H](c1cc(F)cc(F)c1)N1CCc2ccc(S(=O)(=O)Nc3nc(C(=O)N4CCCC4)no3)cc2C1] | 518 [M + H]$^+$ | 1.6 nM |
| 58 | 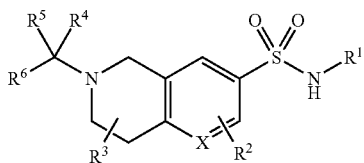 | 582 [M + H]$^+$ | 15 nM |

What is claimed is:

1. A compound of formula (I):

I or pharmaceutically acceptable salts thereof, wherein X is —N— or —CH—;

$R^1$ is a nitrogen containing heterocycle, wherein the nitrogen containing heterocycle is substituted with one or two substituents independently selected from the group consisting of $C_1$-$C_6$alkyl, $C_2$-$C_6$alkene, halogen, halogen-substituted$C_1$-$C_6$alkyl, COOC$_1$-$C_6$alkyl, CONH$_2$, CONHC$_1$-$C_6$alkyl, CON(C$_1$-$C_6$alkyl)$_2$, CONHhalogen-substituted$C_1$-$C_6$alkyl, $C_1$-$C_6$alkoxy, halogen-substituted$C_1$-$C_6$alkoxy, NHC$_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine;

$R^2$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^3$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^4$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;

$R^5$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and —$C_1$-$C_6$alkylOH; and $R^6$ is selected from the group consisting of phenyl or a nitrogen containing heterocycle, wherein the phenyl or nitrogen containing heterocycle is unsubstituted or substituted with one, two or three substituents independently selected from the group consisting of $C_1$-$C_6$alkyl, $C_2$-$C_6$alkene, halogen, halogen-substituted$C_1$-$C_6$alkyl, —COOC$_1$-$C_6$alkyl, CONH$_2$, CONHC$_1$-$C_6$alkyl, CON(C$_1$-$C_6$alkyl)$_2$, CONH-halogen-substituted$C_1$-$C_6$alkyl, $C_1$-$C_6$alkoxy, halogen-substituted$C_1$-$C_6$alkoxy, —NHC$_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, OH, —$C_1$-$C_6$alkylOH, —OC$_1$-$C_6$alkyl-O—$C_1$-$C_6$alkyl, SC$_1$-$C_6$alkyl, —S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

2. The compound of claim 1, or pharmaceutically acceptable salt thereof, wherein X is —N—.

3. The compound of claim 1, or pharmaceutically acceptable salt thereof, wherein X is —CH—.

4. The compound of claim 1, or pharmaceutically acceptable salt thereof, wherein $R^1$ is selected from the group consisting of isoxazole, pyrazine, oxadiazole and pyridazine, wherein the isoxazole, pyrazine, oxadiazole or pyridazine is substituted with one or two substituents independently selected from the group consisting of $C_1$-$C_6$alkyl, $C_2$-$C_6$alkene, halogen, halogen-substituted$C_1$-$C_6$alkyl, COOC$_1$-$C_6$alkyl, CONH$_2$, CONHC$_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NHC$_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine.

5. The compound of claim 1, or pharmaceutically acceptable salt thereof, wherein $R^1$ is isoxazole, wherein the isoxazole is substituted with one or two substituents independently selected from the group consisting of $C_1$-$C_6$alkyl, $C_2$-$C_6$alkene, halogen, halogen-substituted$C_1$-$C_6$alkyl, COOC$_1$-$C_6$alkyl, CONH$_2$, CONHC$_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NHC$_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine.

6. The compound of claim 1, or pharmaceutically acceptable salt thereof, wherein $R^4$ is hydrogen or $C_1$-$C_6$alkyl.

7. The compound of claim 1, or pharmaceutically acceptable salt thereof, wherein $R^5$ is hydrogen.

8. The compound of claim 1, or pharmaceutically acceptable salt thereof, wherein $R^6$ is phenyl, wherein the phenyl is unsubstituted or substituted with one, two or three substituents independently selected from the group consisting of $C_1$-$C_6$alkyl, $C_2$-$C_6$alkene, halogen, halogen-substituted$C_1$-$C_6$alkyl, —COOC$_1$-$C_6$alkyl, CONH$_2$, CONHC$_1$-$C_6$alkyl, CON($C_1$-$C_6$alkyl)$_2$, CONH-halogen-substituted$C_1$-$C_6$alkyl, $C_1$-$C_6$alkoxy, halogen-substituted$C_1$-$C_6$alkoxy, —NHC$_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, OH, —$C_1$-$C_6$alkylOH, —OC$_1$-$C_6$alkyl-O—$C_1$-$C_6$alkyl, SC$_1$-$C_6$alkyl, —S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

9. The compound of claim 1, or pharmaceutically acceptable salt thereof, wherein $R^6$ is selected from the group consisting of pyrimidine, pyridine, thiazole and pyrazine, wherein the pyrimidine, pyridine, thiazole or pyrazine is unsubstituted or substituted with one, two or three substituents independently selected from the group consisting of $C_1$-$C_6$alkyl, $C_2$-$C_6$alkene, halogen, halogen-substituted$C_1$-$C_6$alkyl, —COOC$_1$-$C_6$alkyl, CONH$_2$, CONHC$_1$-$C_6$alkyl, CON($C_1$-$C_6$alkyl)$_2$, CONH-halogen-substituted$C_1$-$C_6$alkyl, $C_1$-$C_6$alkoxy, halogen-substituted$C_1$-$C_6$alkoxy, —NHC$_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, OH, —$C_1$-$C_6$alkylOH, —OC$_1$-$C_6$alkyl-O—$C_1$-$C_6$alkyl, SC$_1$-$C_6$alkyl, —S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

10. The compound of claim 1, or pharmaceutically acceptable salt thereof, wherein $R^6$ is unsubstituted.

11. The compound of claim 1, or pharmaceutically acceptable salt thereof, wherein $R^6$ is substituted with one, two or three substituents independently selected from the group consisting of $C_1$-$C_6$alkyl, $C_2$-$C_6$alkene, halogen, halogen-substituted$C_1$-$C_6$alkyl, —COOC$_1$-$C_6$alkyl, —CONH$_2$, —CONHC$_1$-$C_6$alkyl, —CON($C_1$-$C_6$alkyl)$_2$, —CONHhalogen-substituted$C_1$-$C_6$alkyl, —$C_1$-$C_6$alkoxy, halogen-substituted$C_1$-$C_6$alkoxy, —NHC$_1$-$C_6$alkyl, $C_3$-$C_6$cycloalkyl, halogen-substituted$C_3$-$C_6$cycloalkyl, O—$C_1$-$C_6$alkyl-$C_3$-$C_6$cycloalkyl, O—$C_1$-$C_6$alkyl-halogen-substituted$C_3$-$C_6$cycloalkyl, —OH, —$C_1$-$C_6$alkylOH, —O—$C_1$-$C_6$alkyl-O—$C_1$-$C_6$alkyl, SC$_1$-$C_6$alkyl, S-halogen-substituted$C_1$-$C_6$alkyl, pyrrole, phenyl, halogen-substituted phenyl, pyrazole, N-methyl pyrazole, pyrroline, CO-pyrrolidine, azetidine and CO-azetidine.

12. A compound, or pharmaceutically acceptable salt thereof, selected from the group consisting of:

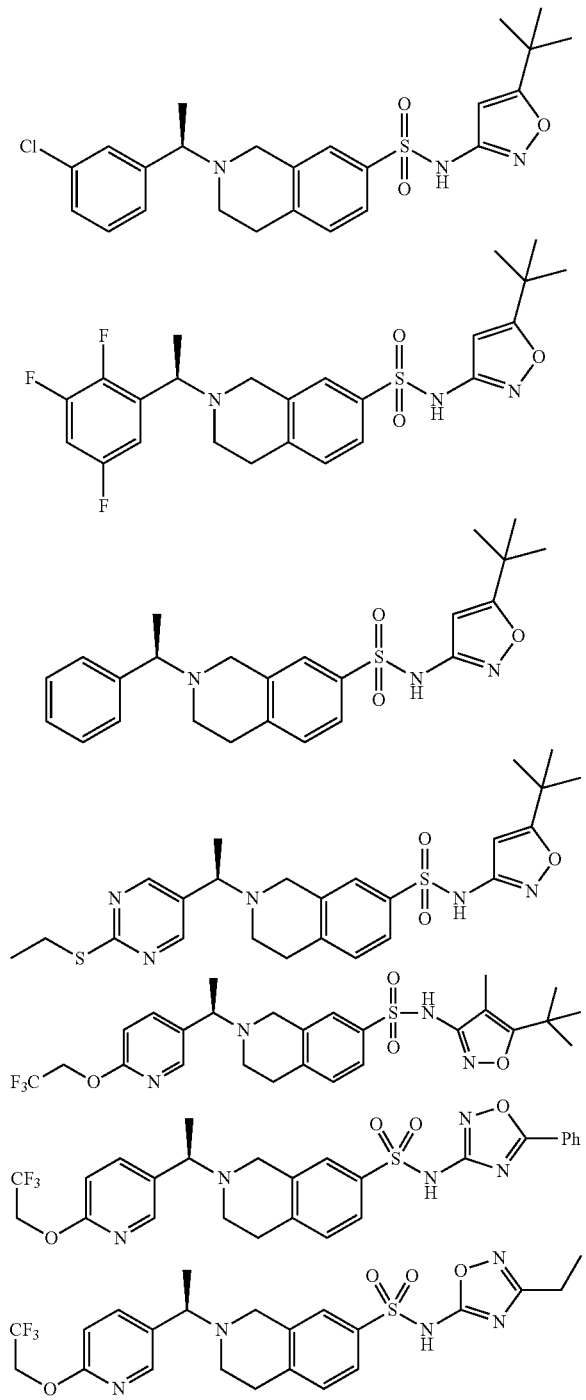

113
-continued
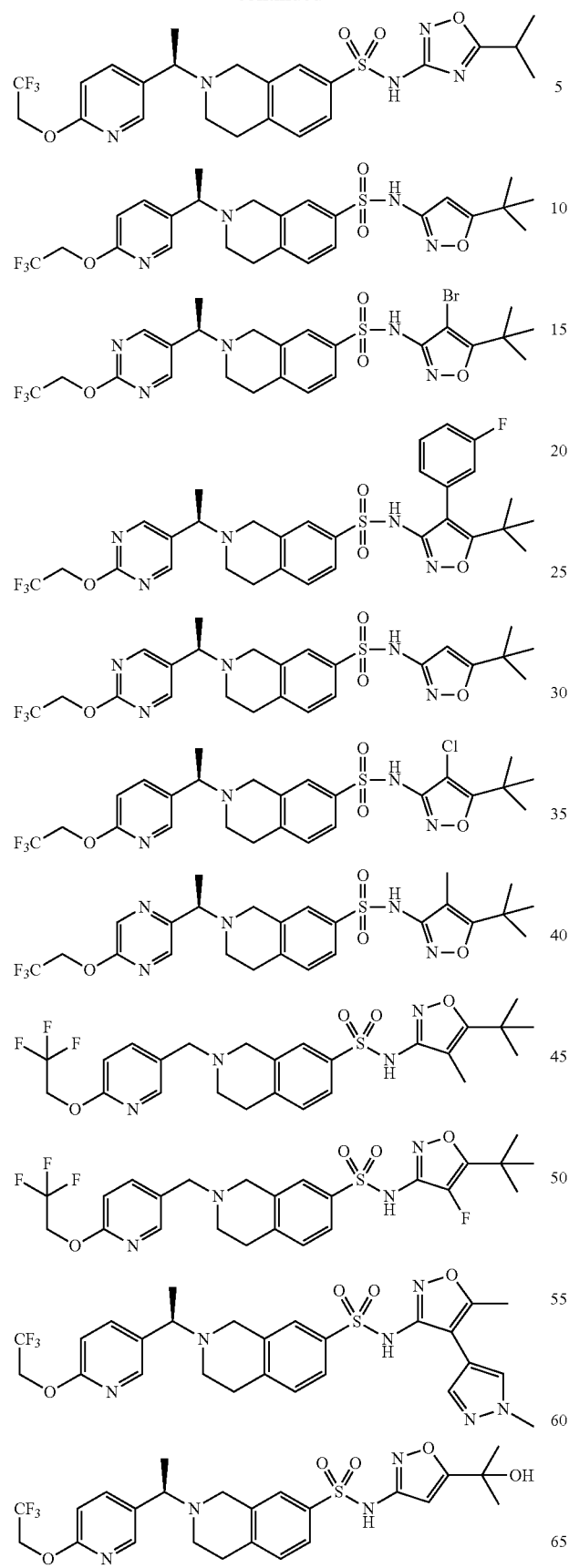
114
-continued
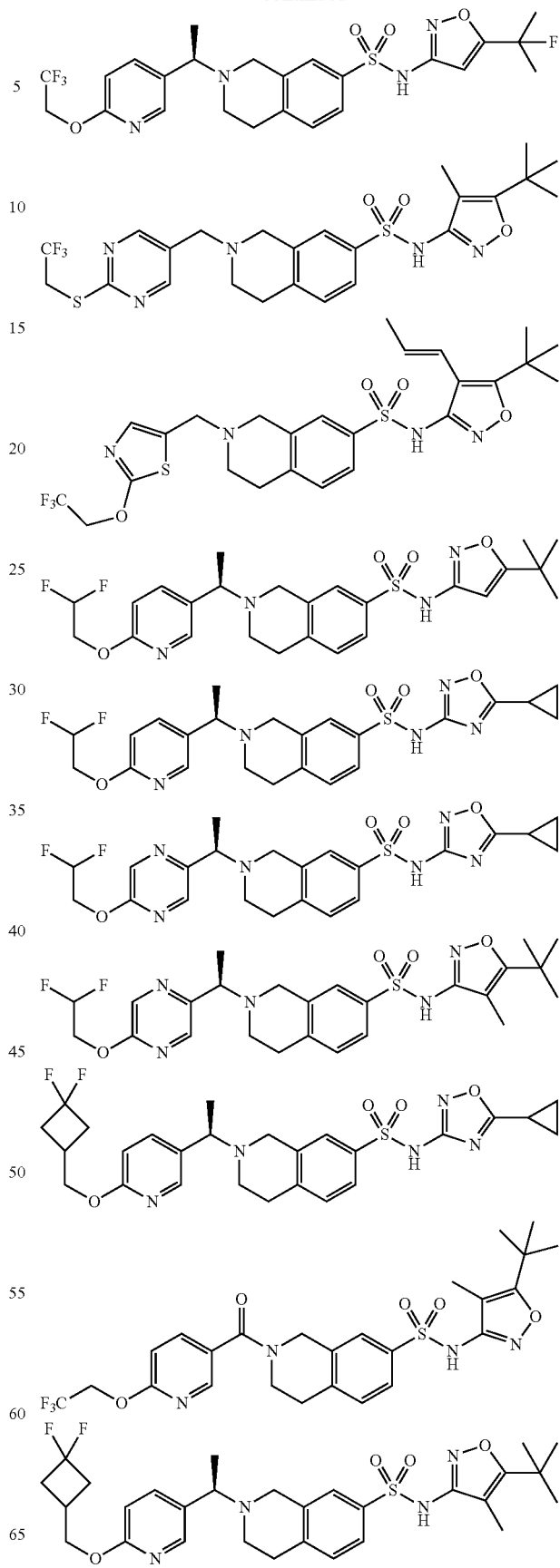

115
-continued
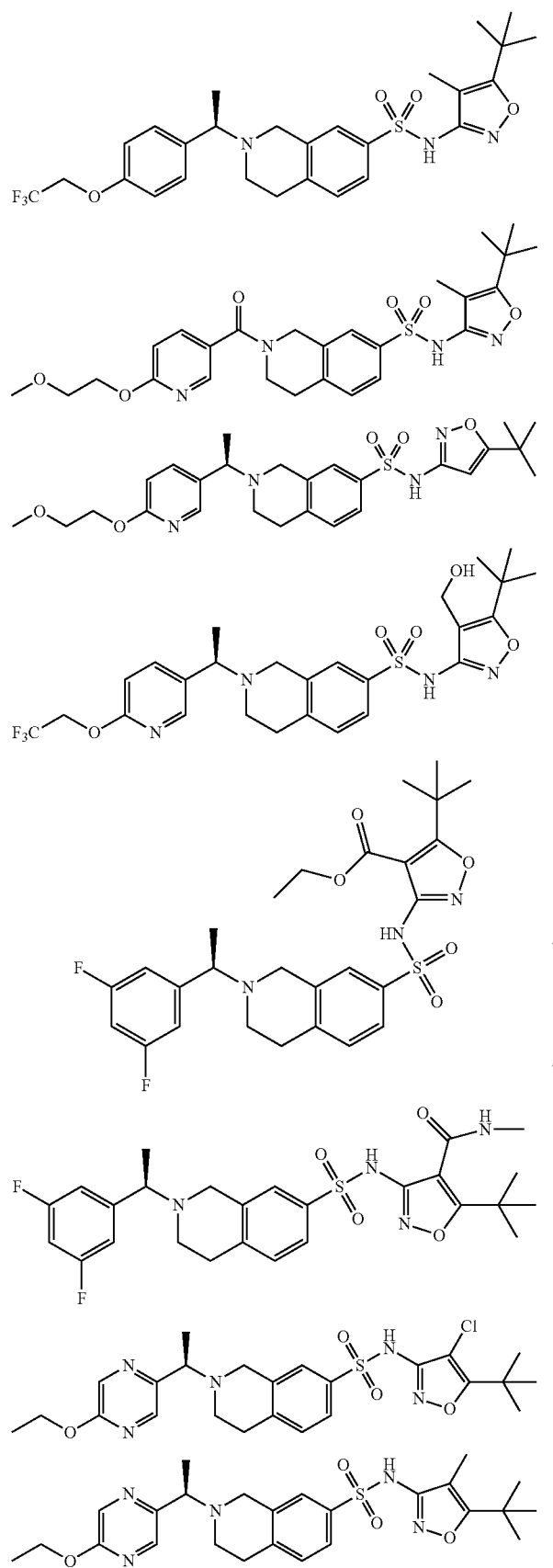
116
-continued
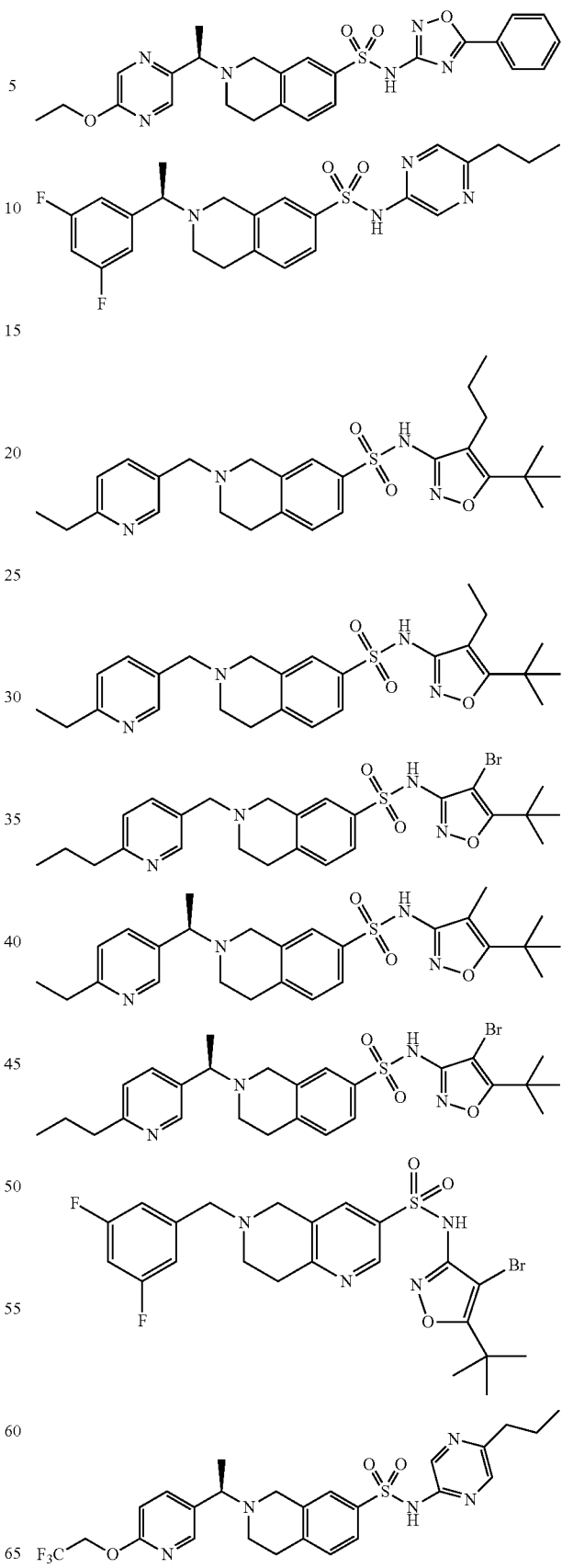

-continued

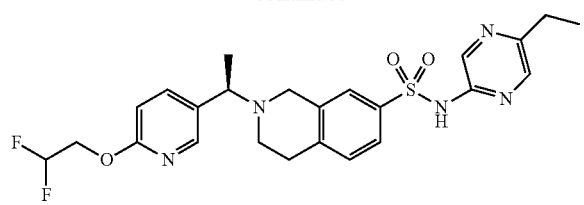

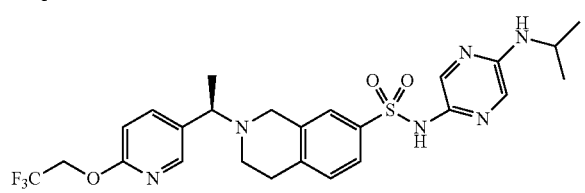

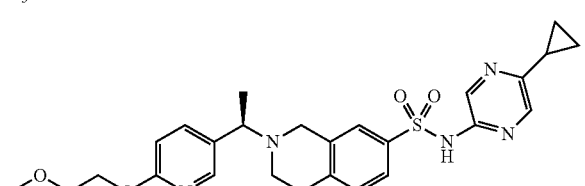

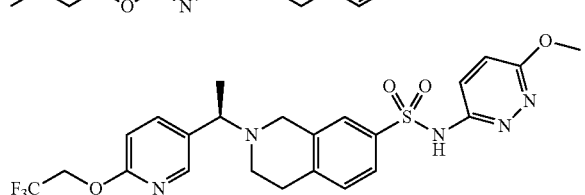

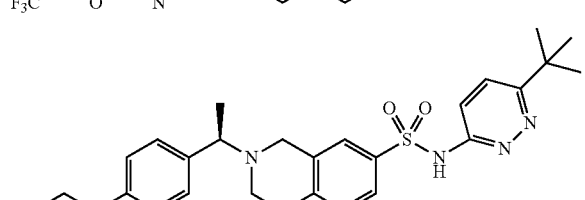

-continued

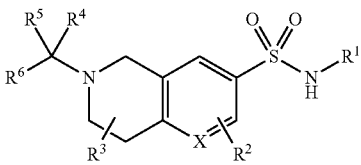

13. A pharmaceutical composition comprising a compound of claim 1, or a pharmaceutically acceptable salt thereof, and a pharmaceutically acceptable carrier.

14. A method for the treatment of a condition selected from the group consisting of obesity and diabetes comprising administering to an individual a pharmaceutical composition comprising a compound of formula (I):

I or pharmaceutically acceptable salts thereof, wherein X is
—N— or —CH—;
$R^1$ is a nitrogen containing heterocycle, wherein the nitrogen containing heterocycle is substituted with one or two substituents independently selected from the group consisting of $C_1$-$C_6$alkyl, $C_2$-$C_6$alkene, halogen, halogen-substituted$C_1$-$C_6$alkyl, COOC$_1$-$C_6$alkyl, CONH$_2$, CONHC$_1$-$C_6$alkyl, CON($C_1$-$C_6$alkyl)$_2$, CONHhalogen-substituted$C_1$-$C_6$alkyl, $C_1$-$C_6$alkoxy, halogen-substituted$C_1$-$C_6$alkoxy, NHC$_1$-$C_6$alkyl, $C_3$-$C_6$cycloalkyl, halogen-substituted$C_3$-$C_6$cycloalkyl, —OH, $C_1$-$C_6$alkylOH, pyrrole, phenyl, halogen-substituted phenyl, pyrazole, N-methyl pyrazole, pyrroline, CO-pyrrolidine, azetidine and CO-azetidine;
$R^2$ is selected from the group consisting of hydrogen, halogen, $C_1$-$C_6$alkyl, $C_1$-$C_6$alkoxy, halogen-substituted$C_1$-$C_6$alkyl, halogen-substituted$C_1$-$C_6$alkoxy, —OH and $C_1$-$C_6$alkylOH;
$R^3$ is selected from the group consisting of hydrogen, halogen, $C_1$-$C_6$alkyl, $C_1$-$C_6$alkoxy, halogen-substitutedC$_1$-C$_6$alkyl, halogen-substitutedC$_1$-C$_6$alkoxy, —OH and C$_1$-C$_6$alkylOH;

R$^4$ is selected from the group consisting of hydrogen, halogen, C$_1$-C$_6$alkyl, C$_1$-C$_6$alkoxy, halogen-substitutedC$_1$-C$_6$alkyl, halogen-substitutedC$_1$-C$_6$alkoxy, —OH and C$_1$-C$_6$alkylOH, or when combined with R$^5$ is an oxo group;

R$^5$ is selected from the group consisting of hydrogen, halogen, C$_1$-C$_6$alkyl, C$_1$-C$_6$alkoxy, halogen-substitutedC$_1$-C$_6$alkyl, halogen-substitutedC$_1$-C$_6$alkoxy, —OH and —C$_1$-C$_6$alkylOH, or when combined with R$^4$ is an oxo group; and R$^6$ is selected from the group consisting of phenyl or a nitrogen containing heterocycle, wherein the phenyl or nitrogen containing heterocycle is unsubstituted or substituted with one, two or three substituents independently selected from the group consisting of C$_1$-C$_6$alkyl, C$_2$-C$_6$alkene, halogen, halogen-substitutedC$_1$-C$_6$alkyl, —COOC$_1$-C$_6$alkyl, CONH$_2$, CONHC$_1$-C$_6$alkyl, CON(C$_1$-C$_6$alkyl)$_2$, CONH-halogen-substitutedC$_1$-C$_6$alkyl, C$_1$-C$_6$alkoxy, halogen-substitutedC$_1$-C$_6$alkoxy, —NHC$_1$-C$_6$alkyl, C$_3$-C$_6$cycloalkyl, halogen-substitutedC$_3$-C$_6$cycloalkyl, O—C$_1$-C$_6$alkyl-C$_3$-C$_6$cycloalkyl, O—C$_1$-C$_6$alkyl-halogen-substitutedC$_3$-C$_6$cycloalkyl, OH, —C$_1$-C$_6$alkylOH, —OC$_1$-C$_6$alkyl-O—C$_1$-C$_6$alkyl, SC$_1$-C$_6$alkyl, —S-halogen-substitutedC$_1$-C$_6$alkyl, pyrrole, phenyl, halogen-substituted phenyl, pyrazole, N-methyl pyrazole, pyrroline, CO-pyrrolidine, azetidine and CO-azetidine.

* * * * *